(12) United States Patent
Young et al.

(10) Patent No.: US 7,947,496 B2
(45) Date of Patent: May 24, 2011

(54) CYTOTOXICITY MEDIATION OF CELLS EVIDENCING SURFACE EXPRESSION OF CD44

(75) Inventors: David S. F. Young, Toronto (CA); Helen P. Findlay, Toronto (CA); Susan E. Hahn, Toronto (CA); Lisa M. Cechetto, Ancaster (CA); Fortunata McConkey, Shelburne (CA)

(73) Assignee: Hoffmann-La Roche Inc., Nutley, NJ (US)

( * ) Notice: Subject to any disclaimer, the term of this patent is extended or adjusted under 35 U.S.C. 154(b) by 197 days.

(21) Appl. No.: 11/364,013

(22) Filed: Feb. 28, 2006

(65) Prior Publication Data
US 2006/0216233 A1 Sep. 28, 2006

Related U.S. Application Data

(63) Continuation-in-part of application No. 10/810,165, filed on Mar. 26, 2004, now abandoned, which is a continuation-in-part of application No. 10/647,818, filed on Aug. 22, 2003, now Pat. No. 7,189,397, which is a continuation-in-part of application No. 10/603,000, filed on Jun. 23, 2003, now Pat. No. 7,252,821, which is a continuation-in-part of application No. 09/727,361, filed on Nov. 29, 2000, now Pat. No. 6,657,048, which is a continuation-in-part of application No. 09/415,278, filed on Oct. 8, 1999, now Pat. No. 6,180,357.

(51) Int. Cl.
C12N 5/16 (2006.01)
C12N 15/00 (2006.01)
A61K 39/395 (2006.01)
A61K 30/00 (2006.01)
C12P 21/08 (2006.01)
C07K 16/00 (2006.01)

(52) U.S. Cl. .................. 435/334; 424/144.1; 424/178.1; 530/388.22; 530/391.1; 435/440

(58) Field of Classification Search .................. 435/334, 435/440; 530/388.22, 391.1; 424/144.1, 424/178.1
See application file for complete search history.

(56) References Cited

U.S. PATENT DOCUMENTS

| | | | |
|---|---|---|---|
| 4,172,124 A | 10/1979 | Koprowski et al. | |
| 4,861,581 A | 8/1989 | Epstein et al. | |
| 5,171,665 A | 12/1992 | Hellstrom et al. | |
| 5,484,596 A | 1/1996 | Hanna, Jr. et al. | |
| 5,530,101 A * | 6/1996 | Queen et al. ............... | 530/387.3 |
| 5,616,468 A | 4/1997 | Salmi et al. | |
| 5,693,322 A | 12/1997 | Creekmore et al. | |
| 5,693,763 A | 12/1997 | Codington et al. | |
| 5,750,102 A | 5/1998 | Eisenbach et al. | |
| 5,780,033 A | 7/1998 | Torchillin et al. | |
| 5,783,186 A | 7/1998 | Arakawa et al. | |
| 5,849,876 A | 12/1998 | Linsley et al. | |
| 5,869,045 A | 2/1999 | Hellstrom et al. | |
| 5,869,268 A | 2/1999 | Kudo et al. | |
| 5,879,898 A * | 3/1999 | Tarin et al. .................. | 435/7.21 |
| 5,885,575 A | 3/1999 | Herrlich et al. | |
| 5,916,561 A | 6/1999 | Adolf et al. | |
| 5,942,417 A | 8/1999 | Ni et al. | |
| 5,980,896 A * | 11/1999 | Hellstrom et al. ......... | 424/183.1 |
| 6,180,357 B1 | 1/2001 | Young et al. | |
| 6,372,441 B1 | 4/2002 | Heider et al. | |
| 6,657,048 B2 | 12/2003 | Young et al. | |
| 2001/0003777 A1 | 6/2001 | Young et al. | |
| 2001/0009665 A1 | 7/2001 | Young et al. | |
| 2002/0041877 A1 | 4/2002 | Young et al. | |
| 2002/0051780 A1* | 5/2002 | Lindhofer et al. ......... | 424/130.1 |
| 2002/0160010 A1 | 10/2002 | Herrlich et al. | |
| 2003/0103985 A1 | 6/2003 | Adolf et al. | |
| 2004/0001789 A1 | 1/2004 | Young et al. | |
| 2004/0101530 A1 | 5/2004 | Young et al. | |
| 2004/0105815 A1 | 6/2004 | Young et al. | |
| 2005/0008646 A1 | 1/2005 | Young et al. | |
| 2005/0018667 A1 | 1/2005 | Chandra et al. | |
| 2006/0216233 A1 | 9/2006 | Young et al. | |
| 2008/0274049 A1* | 11/2008 | Young et al. .................. | 424/1.49 |

FOREIGN PATENT DOCUMENTS

| | | |
|---|---|---|
| WO | WO 94/12631 | 6/1994 |
| WO | WO 95/20401 | 8/1995 |
| WO | WO 02/082076 | 10/2002 |
| WO | WO 02/094879 | 11/2002 |
| WO | WO2005/018667 | 3/2003 |
| WO | WO 03/055515 | 7/2003 |
| WO | WO2004087205 | 10/2004 |
| WO | WO2004/112834 | 12/2004 |

OTHER PUBLICATIONS

Campbell et al, Biology, 5th ed. p. 856, 1999.*
M. Allouche et al, "Ligation of the CD44 adhesion molecule inhibits drug-induced apoptosis in human myeloid leukemia cells", Blood, 96(3):1187-1190 (Aug. 2000).
C. Badger et al., "Prospects for monoclonal antibody therapy of leukemia and lymphoma", Cancer, 58:584-589 (1986).
I. Barshack et al, "CD44 expression in normal adrenal tissue and adrenal tumors", J. Clin. Pathol., 51:52-54 (1998).
A. Begg et al, "Rapid fluorescence-based assay for radiosensitivity and chemosensitivity testing in mammalian cells in vitro", Cancer Research, 49:565-569 (Feb. 1989).

(Continued)

Primary Examiner — Larry R. Helms
Assistant Examiner — Lynn Bristol
(74) Attorney, Agent, or Firm — Fish & Richardson P.C.

(57) ABSTRACT

This invention relates to the diagnosis and treatment of cancerous diseases, particularly to the mediation of cytotoxicity of tumor cells; and most particularly to the use of cancerous disease modifying antibodies (CDMAB), optionally in combination with one or more chemotherapeutic agents, as a means for initiating the cytotoxic response. The invention further relates to binding assays which utilize the CDMAB of the instant invention.

5 Claims, 54 Drawing Sheets
(35 of 54 Drawing Sheet(s) Filed in Color)

OTHER PUBLICATIONS

Becton Dickinson Technical Data Sheet for L178 Clone (published Nov. 5, 2003).

E. Boven et al, "Monoclonal antibodies in cancer treatment: where do we stand after 40 years?", Radiotherapy and Oncology, 5:109-117 (1986).

R. Breyer et al, "Disruption of intracerebral progression of C6 rat glioblastoma by in vivo treatment with anti-CD44 monoclonal antibody", J. Neurosurg., 92:140-149 (Jan. 2000).

M. Chatterjee et al, "Idiotypic antibody immunotherapy of cancer", Cancer Immunol. Immunother, 38:75-82 (1994).

M. Co et al, "Chimeric and humanized antibodies with specificity for the CD33 antigen", J. Immunol., 148:1149-1154 (Feb. 1992).

D. Colnot et al, "Reinfusion of unprocessed, granulocyte colony-stimulating factor-stimulated whole blood allows dose escalation of 186relabeled chimeric monoclonal antibody U36 radioimmunotherapy in a phase I dose escalation study", Clin. Cancer Res., 8:3401-3406 (Nov. 2002).

D. Colnot et al, "Radioimmunotherapy in patients with head and neck squamous cells carcinoma:initial experience", Head & Neck, 23:559-565 (Jul. 2001).

D. Colnot et al, "Phase I therapy study of 186Re-labeled chimeric monoclonal antibody U36 in patients with squamous cell carcinoma of the head and neck", J. Nucl. Med., 41:1999-2010 (Dec. 2000).

D. Colnot et al, "Evaluation of limited blood sampling in a preceding 99mTC-labeled diagnostic study to predict the pharmacokinetics and myelotoxicity of 186Re-cMAb U36 radioimmunotherapy", J. Nucl. Med., 42(9):1364-1367 (Sep. 2001).

A. Costa et al, "Implications of disaggregation procedures on biological representation of human solid tumours", Cell Tisue Kinet., 20:171-180 (1987).

J. Cruse et al, Illustrated Dictionary of Immunology, CRC Press, p. 280 (1995).

B. Curti, "Physical barriers to drug delivery in tumors", Critical Reviews in Oncology/Hematology, 14:29-39 (1993).

A. Daar et al, "The membrane antigens of human colorectal cancer cells: demonstration with monoclonal antibodies of heterogeneity within and between tumours and of anomalous expression of HLA-DR", Eur. J. Cancer Clin. Oncol., 19(2):209-220 (1983).

S. Dairkee et al, "Partial enzymatic degradation of stroma allows enrichment and expansion of primary breast tumor cells", Cancer Research, 57:1590-1596 (Apr. 1997).

R. De Bree et al, "Selection of monoclonal antibody E48 IgG or U36 IgG for adjuvant radioimmunotherapy in head and neck cancer patients", British J. Cancer, 75(7):1049-1060 (1997).

R. De Bree et al, "Radioimmunoscintigraphy and biodistribution of technetium-99m-labeled monoclonal antibody U36 in patients with head and neck cancer", Clin. Can. Res., 1:591-598 (Jun. 1995).

S. Denning et al, "Antibodies against the CD44 p80, lymphocyte homing receptor molecule augment human peripheral blood T cell activation", J. Immunol., 144:7-15 (Jan. 1990).

G. Dermer, "Another anniversary for the war on cancer", Bio/Technology, 12:320 (Mar. 1994).

R. Dillman, "Antibodies as cytotoxic therapy", J. Clin. Oncol., 12(7):1497-1515 (Jul. 1994).

R. Dillman, "Monoclonal antibodies for treating cancer", Annals of Internal Medicine, 111:592-603 (1989).

M. Disis et al, "HER-2/neu protein: a target for antigen-specific immunotherapy of human cancer", Advances in Cancer Research, 71:343-371 (1997).

H. Drexler, "Recent results on the biology of Hodgkin and Reed-Sternberg cells", Leukemia and Lymphoma, 9:1-25 (1993).

Eckhardt et al., "Developmental Therapeutics: Successes and Failures of Clinical Trial Designs of Targeted Compounds"; ASCO Educational Book, 39th Annual Meeting, 2003, pp. 209-219.

M. Embleton, "Monoclonal antibodies to osteogenic sarcoma antigens", Immunol. Ser., 23:181-207 (1984).

S. Engelholm et al, "Disaggregation of human solid tumours by combined mechanical and enzymatic methods", Br. J. Cancer, 51:93-98 (1985).

A. Epstein et al, "Two new monoclonal antibodies, Lym-1 and Lym-2, reactive with human B-lymphocytes and derived tumors, with immunodiagnostic and immunotherapeutic potential", Cancer Research, 47:830-840 (1987).

B. Flanagan et al, "Chemical composition and tissue distribution of the human CDw44 glycoprotein", Immunol., 67:167-17.

K. Foon, "Biological therapy of cancer", Breast Cancer Research & Treatment, 7:5-14 (1986).

S. Fox et al, "Normal human tissues, in addition to some tumors, express multiple different CD44 isoforms", Cancer Res., 54:4539-4546 (Aug. 1994).

R. Freshney, "Culture of animal cells", a Manual of Basic Technique, Alan R. Liss, Inc., New York, p. 3 (1983).

H. Dvorak et al, "Structure of solid tumors and their vasculature: implications for therapy with monoclonal antibodies", Cancer Cells, 3(3):77-85 (Mar. 1991).

B. Franzen et al, "Nonenzymatic extraction of cells from clinical tumor material for analysis of gene expression by two-dimensional polyacrylamide gel electrophoresis", Electrophoresis, 14:1045-1053 (1993).

J. Berzoksky et al, "Chapter 8: Immunology and antigen structure", In Fundamental Immunology, p. 242, ed. William E. Paul M.D., 3d ed. Raven Press, NY (1993).

R. Galandrini et al, CD44 Triggering enhances human NK cell cytotoxic functions, Journal of Immunology, 153:4399-4407 (1994).

U. Gunthert et al, "A new variant of glycoprotein CD44 confers metastatic potential to rat carcinoma cells", Cell, 65:13-24 (Apr. 1991).

Y. Guo et al, "Inhibition of human melanoma growth and metastasis in vivo by anti-CD44 monoclonal antibody", Cancer Res., 54:1561-1565 (Mar. 1994).

T. Gura, "Systems for identifiying new drugs are often faulty", Science, 278:1041-1042 (Nov. 1997).

L. Hartwell et al, "Integrating genetic approaches into the discovery of anticancer drugs", Science, 278:1064-1068 (Nov. 1997).

D. Harris et al, "Serotherapy of cancer", Seminars in Oncology, 16(3):180-198 (Jun. 1989).

K. Heider et al, "Differential expression of CD44 splice variants in intestinal- and diffuse-type human gastric carcinomas and normal gastric mucosa", Cancer Res., 53:4197-4203 (Sep. 1993).

K. Heider et al, "A human homologue of the rat metastasis-associated variant of CD44 is expressed in colorectal carcinomas and adenomatous polyps", J. Cell Biol., 120:27-233 (Jan. 1993).

K. Heider et al, "Splice variants of the cell surface glycoprotein CD44 associated with metastatic tumour cells are expressed in normal tissues of humans and cynomolgus monkeys", Eur. J. Cancer, 31A(13/14):2385-2391 (1995).

K. Heider et al, "Characterization of a high-affinity monoclonal antibody specific for CD44v6 as candidate for immunotherapy of squamous cell carcinomas", Cancer Immunol. Immunother., 43:245-253 (1996).

D. Herlyn et al, "Monoclonal anticolon carcinoma antibodies in complement-dependent cytotoxicity", Int. J. Cancer, 27:769-774 (1981).

S. Hirschfeld et al, "Oncology drug development: United States Food and Drug Administration perspective", Critical Reviews in Oncology/Hematology 42:137-143 (2002).

J. Horoszewicz et al, "Monoclonal antibodies to a new antigenic marker in epithelial prostatic cells and serum of prostatic cancer patients", Anticancer Research, 7:927-936 (1987).

E. Holz et al, "Antibody-based immunotherapeutic strategies in colorectal cancer", Recent Results in Cancer Research, 142:381-400 (1996).

T. Hsu, "Karyology of cells in culture—a preparation and analysis of karyotypes and idiograms", in Tissue Culture Methods and Applications, eds. Kruse and Patterson, Academic Press, New York, pp. 764-737 (1973).

R. Jain, "Barriers to drug delivery in solid tumors", Scientific American, 271(1):58-65 (Jul. 1994).

R. Johnson et al, "The clinical impact of screening and other experimental tumor studies", Cancer Treatment Review, 2:1-31 (1975).

S. Jalkanen et al, "Biochemical properties of glycoproteins involved in lymphocyte recognition of high endothelial venules in man", J. Immunol., 141:1615-1623 (Sep. 1988).

S. Kayastha et al, "Expression of the hyaluronan receptor, CD44S, in epithelial ovarian cancer is an independent predictor of survival", Clin. Cancer Res., 5:1073-1076 (May 1999).

S. Kennel et al, "CD44 expression on murine tissues", J. Cell Science, 104:373-382 (1993).

M. Khoursheed et al, "Expression of CD44s in human colorectal cancer", Pathology Oncology Research, 8(3):170-174 (2002).

A. Knuth et al, "ADCC reactivity of human melanoma cels with mouse monoclonal antibodies", Proc. Am. Assoc. Cancer Res., 25:1005 (Mar. 1984) Abstract only.

G. Kohler et al, "Continuous cultures of fused cells secreting antibody of predefined specificity", Nature, 256:495-497 (Aug. 1975).

G. Koopman et al, "Activated human lymphocytes and aggressive non-hodgkin's lymphomas express a homologue of the rat metastasis-associated variant of CD44", J. Exp. Med., 177:897-904 (Apr. 1993).

V. Kravtsov et al, "Automated monitoring of apoptosis in suspension cell cultures", Laboratory Investigation, 74(2):557-570 (1996).

M. Kuppner et al, "Differential expression of the CD44 molecule in human brain tumours", Int. J. Cancer, 50:572-577 (1992).

C. Mackay et al, "Expression and modulation of CD44 variant isoforms in humans", J. Cell Biol., 124:71-82 (Jan. 1994).

D. Naor et al, "CD44 in cancer", Critical Reviews in Clinical Laboratory Science, 39(6):527-579 (2002).

H. Ponta et al, "CD44: from adhesion molecules to signaling regulators", Nature Reviews, Molecular Cell Biology, 4:33-45 (Jan. 2003).

J. Ross et al, "Expression of the CD44 cell adhesion molecule in urinary bladder transitional cell carcinoma", Mod. Pathol., 9(8):854-860 (1996).

S. Rudikoff et al, "Single amino acid substitution altering antigen-binding specificity", Proc Natl Acad Sci USA, 79:1979-1983 (Mar. 1982).

M. Sami et al, "Regulated expression of exon v6 containing isoforms of CD44 in man: downregulating during malignant transformation of tumors of squamocellular origin", J. Cell Biol., 122(2):431-442 (Jul. 1993).

A. Schrijvers et al, "MAb U36, a novel monoclonal antibody successful in immunotargeting of squamous cell carcinoma of the head and neck", Cancer Res., 53:4383-4390 (Sep. 1993).

S. Seaver, "Monoclonal antibodies in industry: more difficult that originally thought", Genetic Engineering News, 14(14):10 and 21 (1994).

S. Seiter et al, "Prevention of tumor metastasis formation by anti-variant CD44", J. Exp. Med., 177:443-455 (Feb. 1993).

A. Seth et al, "T-cell-receptor-independent activation of cytolytic activity of cytotoxic T lymphocytes mediated through CD44 and pg90MEL-14", Proc. Nat'l Acad Sci. USA, 88:7877-7881 (Sep. 1991).

Y. Shimizu et al, "Dual role of the CD44 molecule in T cell adhesion and activation", J. Immunol., 143:2457-2463 (Oct. 1989).

T. Strobel et al, "In vivo inhibition of CD44 limits intra-abdominal spread of a human ovarian cancer xenograft in nude mice: a novel role for CD44 in the process of peritoneal implantation", Cancer Res., 57:1228-1232 (Apr. 1997).

J. Stroomer et al, "Safety and biodistribution of 99m Technetium-labeled andti-CD44v6 monoclonal antibody BIWA 1 in head and neck cancer patients", Clin. Can. Res., 6:3046-3055 (Aug. 2000).

P. Therasse et al, New guidelines to evaluate the response to treatment in solid tumors, Journal of the National Cancer Institute, 92(3):205-216 (Feb. 2000).

N. Van Hal et al, "Monoclonal antibody U36, a suitable candidate for clinical immunotherapy of squamous-cell carcinoma, recognizes a CD44 isoform", Int. J. Cancer, 68:520-527 (1996).

S. Wallach-Dayan et al, "CD44-dependent lymphoma cell dissemination: a cell surface CD44 variant, rather than standard CD44, supports in vitro lymphoma cell rolling on hyaluronic acid substrate and its in vivo accumulation in the peripheral lymph nodes", J. Cell Science, 114:3463-3477 (2001).

M. Zahalka et al, "Lymph node (but not spleen) invasion by murine lymphoma is both CD44- and hyaluronate-dependent", J. Immunol., 154:5345-5355 (1995).

D. Young et al., "ARH460-16-2: A Therapeutic Monoclonal Antibody Targeting CD44 In Her2/neu Negative Breast cancer", Journal of Clinical Oncology, 22: 193s (Jul. 2004) Abstract 2622.

V. Zawadzki et al, "blockade of metastasis formation by CD44-receptor globulin", Int. J. Cancer, 75:919-924 (1998).

Oostendorp et al., "Evidence for Differences in the Mechanisms by which Antibodies Against CD44 Promote Adhesion of Erythroid and Granulopoietic Progenitors to Marrow Stromal Cells", British Journal of Haematology (1998), vol. 101, pp. 436-445.

Naor et al., "CD44: Structure, Function, and Association with the Malignant Process", Advances in Cancer Research (1997), vol. 71, pp. 241-319.

Co et al., "Humanized Antibodies for Therapy", Nature (1991), vol. 341, pp. 501-502.

Examination report dated Jan. 13, 2010 for corresponding U.S. Appl. No. 12/017,827.

Examination report dated Jan. 14, 2010 for corresponding U.S. Appl. No. 12/114,090.

Examination report dated Jan. 14, 2010 for corresponding U.S. Appl No. 11/807,887.

Examination report dated Feb. 19, 2010 for corresponding U.S. Appl. No. 12/055,014.

Examination report dated Feb. 25, 2010 for corresponding U.S. Appl. No. 11/938,832.

Examination report dated Apr. 5, 2010 for corresponding U.S. Appl. No. 12/017,886.

Examination report dated Apr. 8, 2010 for corresponding U.S. Appl. No. 11/786,165.

Examination report dated Apr. 12, 2010 for corresponding U.S. Appl. No. 11/938,846.

Examination report dated Jun. 16, 2009 for corresponding U.S. Appl. No. 12/055,014.

Examination report dated Jul. 1, 2009 for corresponding U.S. Appl. No. 11/938,841.

Examination report dated Jul. 15, 2009 for corresponding U.S. Appl. No. 12/017,827.

Examination report dated Jul. 24, 2009 for corresponding U.S. Appl. No. 11/975,896.

Examination report dated Jul. 27, 2009 for corresponding U.S. Appl. No. 12/102,662.

Examination report dated Jul. 29, 2009 for corresponding U.S. Appl. No. 11/807,887.

Examination report dated Jul. 30, 2009 for corresponding U.S. Appl. No. 11/807,837.

Examination report dated Aug. 10, 2009 for corresponding U.S. Appl. No. 12/017,855.

Examination report dated Aug. 13, 2009 for corresponding U.S. Appl. No. 11/807,681.

Examination report dated Oct. 13, 2009 for corresponding U.S. Appl. No. 11/786,165.

Examination report dated Oct. 16, 2009 for corresponding U.S. Appl. No. 12/102,953.

Examination report dated Nov. 10, 2009 for corresponding U.S. Appl. No. 12/172,645.

Examination report dated Nov. 19, 2009 for corresponding U.S. Appl. No. 11/938,846.

Examination report dated Nov. 30, 2009 for corresponding U.S. Appl. No. 12/220,362.

Examination report dated Dec. 1, 2008 for corresponding U.S. Appl. No. 11/786,165.

Examination report dated Dec. 10, 2009 for corresponding U.S. Appl. No. 12/229,187.

Examination report dated Dec. 14, 2009 for corresponding U.S. Appl. No. 12/229,203.

Examination report dated Oct. 15, 2009 for corresponding U.S. Appl. No. 12/313,298.

Examination report dated Jul. 17, 2009 for corresponding U.S. Appl. No. 11/938,832.

Examination report dated Jun. 17, 2008 for U.S. Appl. No. 11/774,293.

Examination report dated Mar. 20, 2009 for U.S. Appl. No. 11/777,551.
Examination report dated Apr. 10, 2009 for U.S. Appl. No. 11/774,293.
Examination report dated Apr. 22, 2009 for U.S. Appl. No. 11/879,676.
Examination report dated Jun. 4, 2009 for U.S. Appl. No. 11/880,619.
Examination report dated Jun. 12, 2009 for U.S. Appl. No. 12/284,137.
Examination report dated Mar. 11, 2010 for U.S. Appl. No. 12/102,983.
Examination report dated Apr. 21, 2010 for U.S. Appl. No. 11/807,887.
Examination report dated May 3, 2010 for U.S. Appl. No. 12/356,980.
Examination report dated May 3, 2010 for U.S. Appl. No. 12/357,031.
Examination report dated May 4, 2010 for U.S. Appl. No. 11/807,681.
Examination report dated May 24, 2010 for U.S. Appl. No. 12/217,279.
Examination report dated May 28, 2010 for U.S. Appl. No. 11/938,841.
Examination report dated Jun. 24, 2010 for U.S. Appl. No. 12/017,855.
Examination report dated Jul. 21, 2010 for U.S. Appl. No. 12/229,187.
Examination report dated Jul. 23, 2010 for U.S. Appl. No. 12/229,203.
Examination report dated Jul. 29, 2010 for U.S. Appl. No. 12/378,332.
Examination report dated Aug. 25, 2010 for U.S. Appl. No. 12/313,298.
Beckman et al "Can." 109:170-179 2007.
Cespdes et al "Clin. Trans. Oncol." 8(5)318-329 2006.
Dennis "Nature" 442:739-741 2006.
Fujimori et al "J. Nuc. Med." 31:1191-1198 1990.
Rudnick et al "Can. Biotherp. & Radiopharm." 24:155-162 2009.
Talmadge et al "Am. J. Pathol" 170(3)793-804 2007.
Thurber et al "Adv. Drug Deliv. Rev." 60:1421-1434 2008.
Voskoglou-Nomikos Clin. Can. Res. 9:4227-4239 2003.
Search Report from corresponding application PCT/CA2007/000281.
Written Opinion from corresponding application PCT/CA2007/000281.
EP supplemental search report from corresponding EP application 07701821.6.
Paul "Fundamental Immunology" $3^{rd}$ Ed., 1993, pp. 242.

\* cited by examiner

FIGURE 1

| | Table 1 | Isotype ELISA Fold | | Percentage Cytotoxicity | | | | | | Binding | | |
|---|---|---|---|---|---|---|---|---|---|---|---|---|
| | | | | PC-3 | | LnCap | | CCD-27sk | | PC-3 | LnCap | CCD-27sk |
| | | IgG | IgM | Average | CV | Average | CV | Average | CV | Fold | Fold | Fold |
| | AR37A335.8 | 6.2 | 1.7 | 3 | 6 | 16 | 6 | 3 | 12 | 9.3 | 0.8 | 16.6 |
| Controls | Cycloheximide | | | 57 | 6 | 53 | 23 | 29 | 34 | | | |
| | NaN$_3$ | | | 36 | 14 | 75 | 7 | 22 | 36 | | | |

FIGURE 2

|  | Cell Line | Colon | | OVARY | Normal |
|---|---|---|---|---|---|
|  |  | DLD-1 | Lovo | OVCAR-3 | Hs888.Lu |
|  | AR37A335.8 | 80 | 55 | 0 | 0 |
| Negative Controls | MPC-11 | 0 | 0 | 0 | 0 |
| | IgG Buffer | 0 | 0 | 0 | 0 |
| Positive Controls | Anti-EGFR | 125 | 150 | 125 | 0 |
| | CHX | 150 | 150 | 150 | 150 |

FIGURE 3

|  |  | Colon | | OVARY | Normal |
|---|---|---|---|---|---|
|  | Cell Line | DLD-1 | Lovo | OVCAR-3 | Hs888.Lu |
|  | AR37A335.8 | 14.0 | 5.0 | 6.0 | 18.0 |
| Positive Control | Anti-EGFR | 6.0 | 3.0 | 8.0 | 9.0 |

FIGURE 11

| | | | | Binding Score | | | | % of positive |
|---|---|---|---|---|---|---|---|---|
| | | | | H460-16-2 | | | | |
| | | Total # | - | +/- | + | ++ | +++ | Total positive | of total |
| Patients' Sample | Tumors | 53 | 34 | 7 | 2 | 5 | 5 | 19 | 36% |
| | Normal | 3 | 0 | 1 | 0 | 0 | 2 | 3 | 100% |
| Tumor Stage | I | 1 | 0 | 1 | 0 | 0 | 0 | 1 | 100% |
| | II | 12 | 8 | 1 | 0 | 2 | 1 | 4 | 33% |
| | III | 2 | 2 | 0 | 0 | 0 | 0 | 0 | 0% |
| | IV | 33 | 22 | 3 | 2 | 3 | 3 | 11 | 33% |
| | Unknown | 5 | 2 | 2 | 0 | 0 | 1 | 3 | 60% |
| Gleason | Gx(unknown) | 1 | 0 | 0 | 1 | 0 | 0 | 1 | 100% |
| | G1-2 (2-6) | 8 | 6 | 1 | 0 | 0 | 1 | 2 | 25% |
| | G3-4 (7-10) | 44 | 28 | 6 | 1 | 5 | 4 | 16 | 36% |

FIGURE 12
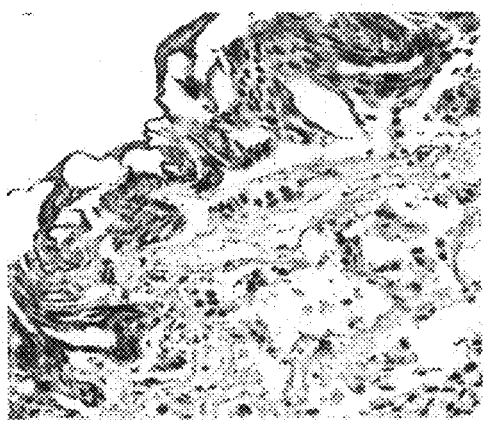
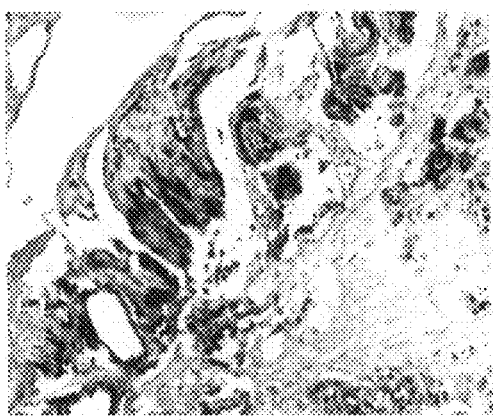
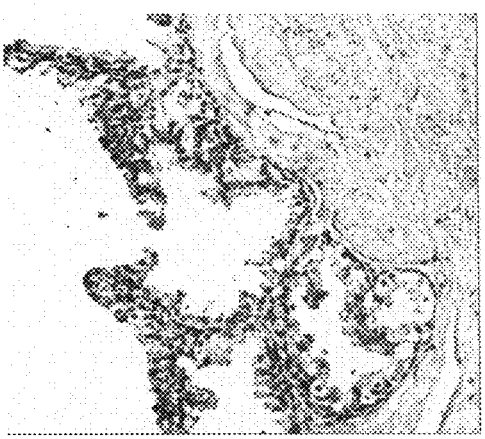
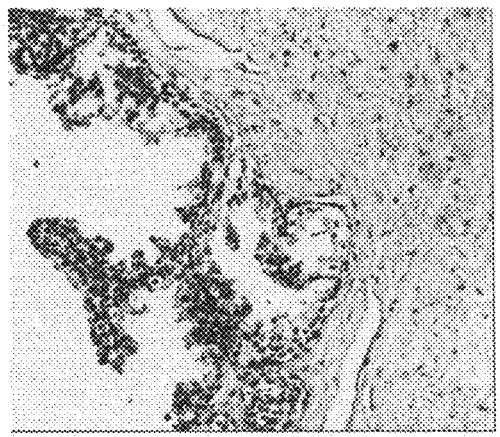

FIGURE 13

| H460-16-2 | | | | | | | | | |
|---|---|---|---|---|---|---|---|---|---|
| Diagnosis | | Total | - | +/- | + | ++ | +++ | Total Positive | % of Positive |
| Tumor | | 49 | 28 | 7 | 8 | 3 | 3 | 21 | 43% |
| Primary Hepatocellular Carcinoma | | 37 | 26 | 4 | 5 | 1 | 1 | 11 | 30% |
| Metastatic Hepatocellular Carcinoma | | 8 | 1 | 3 | 3 | 1 | 0 | 7 | 88% |
| Primary Cholangiocarcinoma | | 2 | 1 | 0 | 0 | 0 | 1 | 1 | 50% |
| Metastatic Cholangiocarcinoma | | 2 | 0 | 0 | 0 | 1 | 1 | 2 | 100% |
| Tumor Stages (AJCC) | I | 2 | 2 | 0 | 0 | 0 | 0 | 0 | 0% |
| | II | 17 | 15 | 0 | 1 | 1 | 0 | 2 | 12% |
| | III | 16 | 8 | 4 | 3 | 0 | 1 | 8 | 50% |
| | IV | 8 | 2 | 2 | 3 | 0 | 1 | 6 | 75% |
| Normal | | 9 | 0 | 0 | 1 | 3 | 5 | 9 | 100% |

FIGURE 15

| Treatment | TUNEL | H & E |
|---|---|---|
| H460-16-2 | 38 | 27 |
| H460-16-2 | 43 | 20 |
| H460-16-2 | 42 | 18 |
| H460-16-2 | 47 | 25 |
| AVERAGE | 42.5 | 22.5 |
| St. Dev. | 3.70 | 4.20 |
| Buffer | 49 | 22 |
| Buffer | 38 | 16 |
| Buffer | 18 | 10 |
| Buffer | 21 | 20 |
| AVERAGE | 31.5 | 17 |
| St. Dev. | 14.62 | 5.29 |

FIGURE 19A pCR2.1 ARH460-16-2 Vκ(M)1-1
GAATTGTAATACGACTCACTATAGGGCGAATTGGGCCCTCTAGATGCATGCTCGAGCGGCCGC
CAGTGTGATGGATATCTGCAGAATTCGCCCTTGATATGGTATCCTCACCTCAGTTCCTTGGTCT
CCTGTTGCTCTGTTTTCAAGGTACCAGATGTGATATCCAGATGACACAGACTACATCCTCCCTG
TCTGTCTCTCTGGGAGACAGAGTCACCATCAATTGCAGGGCAAGTCAGGACATTAACAATTAT
TTAAACTGGTATCAGCAGAAACCAGATGGAACTGTTAAACTCCTGATCTACTACACATCAAGA
TTACACTCAGGAGTCCCATCAAGGTTCAGTGGCAGTGGGTCTGGAACAGATTTTTCTCTCACC
ATTAGCAACCTGGAGAAAGAAGATGTTGCCACTTACTTTTGCCAACAGGGTAGTACGCTTCCA
TTCACGTTCGGCTCGGGGACAAAGTTGGAAATAAAACGGGCTGATGCTGCACCAACTGTATCC
ATCTTCCCACCATCCAGTAAGCTTGGGAAGGGCGAATTCCAGCACACTGGCGGCCGTTACTAG
TGGATCCGAGCTCGGTACCAAGCTTGGCGTAATCATGGTCATAGCTGTTTCCTGTGTGAAATT
GTTATCCGCTCACAATTCCACACAACATACGAGCCGGAAGCATAAAGTGTAAAGCCTGGGGT
GCCTAATGAGTGAGCTAACTCACATTAATTGCGTTGCGCTCACTGGCCGCTTTCCAGTCGGGA
AACCTGTCGTGCCAGCTGCATTAATGAATCGGCCAACGCGCGGGGAGAGGCGG pCR2.1 ARH460-16-2 Vκ(M)1-2
GCAATTGTAATACGACTCACTATAGGGCGAATTGGGCCCTCTAGATGCATGCTCGAGCGGCCG
CCAGTGTGATGGATATCTGCAGAATTCGCCCTTCCCAAGCTACTGGATGGTGGGAAGATGGAT
ACAGTTGGTGCAGCATCAGCCCGTTTTATTTCCAACTTTGTCCCCGAGCCGAACGTGAATGGA
AGCGTACTACCCTGTTGGCAAAAGTAAGTGGCAACATCTTCTTTCTCCAGGTTGCTAATGGTG
AGAGAAAAATCTGTTCCAGACCCACTGCCACTGAACCTTGATGGGACTCCTGAGTGTAATCTT
GATGTGTAGTAGATCAGGAGTTTAACAGTTCCATCTGGTTTCTGCTGATACCAGTTTAAATAAT
TGTTAATGTCCTGACTTGCCCTGCAATTGATGGTGACTCTGTCTCCCAGAGAGACAGACAGGG
AGGATGTAGTCTGTGTCATCTGGATATCACATCTGGTACCTTGAAAACAGAGCAACAGGAGAC
CAAGGAACTGAGCTGTGGATACCATGTCGACTAGTAAGGGCGAATTCCAGCACACTGGCGGC
CGTTACTAGTGGATCCGAGCTCGGTACCAAGCTTGGCGTAATCATGGTCATAGCTGTTTCCTGT
GTGAAATTGTTATCCGCTCACAATTCCACACAACATACGAGCCGGAAGCATAAAGTGTAAAG
CCTGGGGTGCCTAATGAGTGAGCTAACTCACATTAATTGCGTTGCGCTCACTGCCCGCTTTCCA
GTCGGGAAACCTGTCGTGCCAGCTGCATTAATGAATCGGCCACGCGCGGGGAGAGGCGGGTT
T pCR2.1 ARH460-16-2 Vκ(M)1-3
GAATTGTAATACGACTCACTATAGGGCGAATTGGGCCCTCTAGATGCATGCTCGAGCGGCCGC
CAGTGTGATGGATATCTGCAGAATTCGCCCTTGGTATCCTCAGCTCAGTTCCTTGGTCTCCTG
TTGCTCTGTTTTCAAGGTACCAGATGTGATATCCAGATGACACAGACTACATCCTCCCTGTCTG
TCTCTCTGGGAGACAGAGTCACCATCAATTGCAGGGCAAGTCAGGACATTAACAATTATTTAA
ACTGGTATCAGCAGAAACCAGATGGAACTGTTAAACTCCTGATCTACTACACATCAAGATTAC
ACTCAGGAGTCCCATCAAGGTTCAGTGGCAGTGGGTCTGGAACAGATTTTTCTCTCACCATTA
GCAACCTGGAGAAAGAAGATGTTGCCACTTACTTTTGCCAACAGGGTAGTACGCTTCCATTCA
CGTTCGGCTCGGGGACAAAGTTGGAAATAAAACGGGCTGATGCTGCACCAACTGTATCCATCT
TCCCACCATCCAGTAAGCTTGGGAAGGGCGAATTCCAGCACACTGGCGGCCGTTACTAGTGGA
TCCGAGCTCGGTACCAAGCTTGGCGTAATCATGGTCATAGCTGTTTCCTGTGTGAAATTGTTAT
CCGCTCACAATTCCACACAACATACGAGCCGGAAGCATAAAGTGTAAAGCCTGGGGTGCCTA
ATGAGTGAGCTAACTCACATTAATTGCGTTGCGCTCACTGCCCGCTTTCCAGTCGGGGAAACC
TGTCGTGCCAGCTGCATTAATGAATCGGCCAACGCGCGGGGAGAGGCGGTTTGCGTATTGGGC
GCTCTTCCGCTTCCTCGCTCACTGACTCGCTGCGCTCGG pCR2.1 ARH460-16-2 Vκ(M)2-1
GTAATACGACTCACTATAGGGCGAATTGGGCCCTCTAGATGCATGCTCGAGCGGCCGCCAGTG
TGATGGATATCTGCAGAATTCGCCCTTGACATGGAGTCAGACACACTCCTGCTATGGGTACTG
CTGCTCTGGGTTCCAGGTTCCACTGGTGACATTGTGCTGACACAGTCTCCTGCTTCCTTAGCTG
TATCTCTGGGGCAGAGGGCCACCATCTCATACAGGGCCAGCAAAAGTGTCAGTACATCTGGCT
ATAGTTATATGCACTGGAACCAACAGAAACCAGGACAGCCACCCAGACTCCTCATCTATCTTG

FIGURE 19B

TATCCAACCTAGAATCTGGGGTCCCTGCCAGGTTCAGTGGCAGTGGGTCTGGGACAGACTTCA
CCCTCAACATCCATCCTGTGGAGGAGGAGGATGCTGCAACCTATTACTGTCAGCACATTAGGG
AGCTTACACGTTCGGAGGGGGGACCAAGCTGGAAATAAAACGGGCTGATGCTGCACCAACTG
TATCCATCTTCCCACCATCCAGTAAGCTTGGGAAGGGCGAATTCCAGCACACTGGCGGCCGTT
ACTAGTGGATCCGAGCTCGGTACCAAGCTTGGCGTAATCATGGTCATAGCTGTTTCCTGTGTG
AAATTGTTATCCGCTCACAATTCCACACAACATACGAGCCGGAAGCATAAAGTGTAAAGCCTG
GGGTGCCTAATGAGTGAGCTAACTCACATTAATTGCGTTGCGCTCACTGCCCGCTTTCCAGTC
GGGAAACCTGTCGTGCCAGCTGCATTAATGAATCGGCCAACGCGCGGGGGAGAGGCGGTTTG
CGTATTGGGCGC pCR2.1 ARH460-16-2 Vκ(M)2-2
GTAATACGACTCACTATAGGGCGAATTGGGCCCTCTAGATGCATGCTCGAGCGGCCGCCAGTG
TGATGGATATCTGCAGAATTCGCCCTTGTCGACATGGAGACAGACACACTGCTGTTATGGGTA
CTGCTGCTCTGGGTTCCAGGTTCCACTGGTGACATTGTGCTGACACAGTCTCCTGCTTCCTTAG
CTGTATCTCTGGGGCAGAGGGCCACCATCTCATACAGGGCCAGCAAAAGTGTCAGTACATCTG
GCTATAGTTATATGCACTGGAACCAACAGAAACCAGGACAGCCACCCAGACTCCTCATCTATC
TTGTATCCAACCTAGAATCTGGGGTCCCTGCCAGGTTCAGTGGCAGTGGGTCTGGGACAGACT
TCACCCTCAACATCCATCCTGTGGAGGAGGAGGATGCTGCAACCTATTACTGTCAGCACATTA
GGGAGCTTACACGTTCGGAGGGGGGACCAAGCTGGAAATAAAACGGGCTGATGCTGCACCAA
CTGTATCCATCTTCCCACCATCCAGTAAGCTTGGGAAGGGCGAATTCCAGCACACTGGCGGCC
GTTACTAGTGGATCCGAGCTCGGTACCAAGCTTGGCGTAATCATGGTCATAGCTGTTTCCTGT
GTGAAATTGTTATCCGCTCACAATTCCACACAACATACGAGCCGGAAGCATAAAGTGTAAAG
CCTGGGGTGCCTAATGAGTGAGCTAACTCACATTAATTGCGTTGCGCTCACTGCCCGCTTTCCA
GTCGGGAAACCTGTCGTGCCAACTGCATTAATGAATCGGCCAACGCGCGGGGAGAGGCGGTT
TGCGTATTGGGCGCTTCTTCCGCTTCCTCGCT pCR2.1 (H460-16-2 V<sub>H</sub>) #1
CCCAAGCTTCCAGGGGCCAGGGGATAGACAGGTGGGGGTGTCGTTTTGGCTGAGGAaTGGTG
ACTGAGGTTCCTTGACCCCAGTAGTCCATAGCATAGTAGTGGTACCTACTACCGTAGTAATTA
GGCCTTGTACAGTAATAAAGGGCTGTGTCTTCAGAGCTCACTTTGCTCATTTGCAGGTCCAGC
GTATTTTTGGCGTTGTCTCTGGAGATGATGAATTGATCCTTTAGAGATGGCGTATAGTTTATCG
AAGTGCTATCTGGATTAACTTCTCCAATCCATTCTAGCCCTTTCCCTGGAGCCTGCCGGACCCA
ACTCATCCAGTATCTACTAAAATCGAATCCTGAGGTTGCACAGGAGAGTTTCAGGGATCCTCC
AGGCTGCACCAGGCCACCTCCAGACTCGAGAAGCTTCACCTCACACTGGACCCCTTTTAAAAG
AGCAACAATAAAAAAAATCAGCCCAAAATCCATGTCAACTAGTA pCR2.1 (H460-16-2 V<sub>H</sub>) #4
ATGGATTTTGGGCTGATTTTTTTTTATTGTTGCTCTTTTAAAAGGGGTCCAGTGTGAGGTGAAGC
TTCTCGAGTCTGGAGGTGGCCTGGTGCAGCCTGGAGGATCCCTGAAACTCTCCTGTGCAACCT
CAGGATTCGATTTTAGTAGATACTGGATGAGTTGGGTCCGGCAGGCTCCAGGGAAAGAGCTA
GAATGGATTGGAGAAGTTAATCCAGATAGCACTTCGATAAACTATACGCCATCTCTAAAGGAT
CAATTCATCATCTCCAGAGACAACGCCAAAAATACGCTGGACCTGCAAATGAGCAAAGTGAG
CTCTGAAGACACAGCCCTTTATTACTGTACAAGGCCTAATTACTACGGTAGTAGGTACCACTA
CTATGCTATGGACTACTGGGGTCAAGGAACCTCAGTCACCGTTTCCTCAGCCAAAACGACACC
CCCATCCGTTTATCCATTGGCCCCTGGAAGCTTGGGA pCR2.1 (H460-16-2 V<sub>H</sub>) #5
CCCAAGCTTCCAGGGGCCAAGGGATAAACGGGTGGGGGTGTCGTTTTGGCTGAGGAAAYGGT
GACTGAGGTTCCTTGACCCCAGTAGTCCATAGCATAGTAGTGGTACCTACTACCGTAGTAATT
AGGCCTTGTACAGTAATAAAGGGCTGTGTCTTCAGAGCTCACTTTGCTCATTTGCAGGTCCAG
CGTATTTTTGGCGTTGTCTCTGGAGATGATGAATTGATCCTTTAGAGATGGCGTATAGTTTATC
GAAGTGCTATCTGGATTAACTTCTCCAATCCATTCTAGCCCTTTCCCTGGAGCCTGCCGGACCC
AACTCATCCAGTATCTACTAAAATCGAATCCTGAGGTTGCACAGGAGAGTTTCAGGGATCCTC
CAGGCTGCACCAGGCCACCTCCAGACTCGAGAAGCTTCACTTCACACTGGACCCCTTTTAAAA
GAGCAACAATAAAAAAAATCAGCCCAAAATCCATGTCGACTAGTA

FIGURE 21 pCR2.1 (ARH460-16-2 V$_H$) # 1
ATCGTAATACGACTCACTATAGGGCGAATTGGGCCCTCTAGATGCATGCTCGAGCGGCCGCCA
GTGTGATGGATATCTGCAGAATTCGCCCTTGGGAATTCATGAAGTTGGGGCTCAGCTGGGTTT
CATGTCGACTAGTCACAAAAGAATCAGCACTCTCATGTCGAAGGGCGAATTCCAGCACACTG
GCGGCCGTTACTAGTGGATCCGAGCTCGGTACCAAGCTTGGCGTAATCATGGTCATAGCTGTT
TCCTGTGTGAAATTGTTATCCGCTCACAATTCCACACAACATACGAGCCGGAAGCATAAAGTG
TAAAGCCTGGGGTGCCTAATGAGTGAGCTAACTCACATTAATTGCGTTGCGCTCACTGCCCGC
TTTCCAGTCGGGAAACCTGTCGTGCCAGCTGCATTAATGAATCGGCCAACGCGCGGGGAGAG
GCGGTTTGCGTATTGGGCGCTCTTCCGCTTCCTCGCTCACTGACTCGCTGCGCTCGGTCGTTCG
GCTGCGGCGAGCGGTATCAGCTCACTCAAAGGCGGTAATACGGTTATCCACAGAATCAGGGG
ATAACGCAGGAAAGAACATGTGAGCAAAAGGCCAGCAAAAGGCCAGGAACCGTAAAAAGGC
CGCGTTTT pCR2.1 (ARH460-16-2 V$_H$) # 3
GAATTGTAATACGACTCACTATAGGGCGAATTGGGCCCTCTAGATGCATGCTCGAGCGGCCGC
CAGTGTGGATGGATATCTGCAGAATTCGCCCTTCCCAAGCTTCCAGGGGCCAAGGGATAGACG
GGTGGGGGTGTCGTTTTGGCTGAGGAAACGGTGACTGAGGTTCCTTGACCCCAGTAGTCCATA
GCATAGTAGTGGTACCTACTACCGTAGTAATTAGGCCTTGTACAGTAATAAAGGGCTGTGTCT
TCAGAGCTCACTTTGCTCATTTGCAGGTCCAGCGTATTTTTGGCGTTGTCTCTGGAGATGATGA
ATTGATCCTTTAGAGATGGCGTATAGTTTATCGAAGTGCTATCTGGATTAACTTCTCCAATCCA
TTCTAGCCCTTTCCCTGGAGCCTGCCGGACCCAACTCATCCAGTATCTACTAAAATCGAATCCT
GAGGTTGCACAGGGAGAGTTTCAGGGATCCTCCAGGCTGCACCAGGCCACCTCCAGACTCGA
GAAGCTTCACCTCACACTGGACCCCTTTTAAAAGAGCAACAATAAAAAAAATCAGCCCAAAA
TCCATGTCGACTAGTAAGGGCGAATTCCAGCACACTGGCGGCCGTTACTAGTGGATCCGAGCT
CGGTACCAAGCTTGGCGTAATCATGGTCATAGCTGTTTCCTGTGTGAAATTGTTATCCGCTCAC
AATTCCACACAACATACGAGCCGGAAGCATAAAGTGTAAAGCCTGGGGTGCCTAATGAGTGA pCR2.1 (ARH460-16-2 V$_H$) # 17
GATTGAATACGACTCACTATAGGGCGAATTGGGCCCTCTAGATGCATGCTCGAGCGGCCGCCA
GTGTGATGGATATCTGCAGAATTCGCCCTTCCCAAGCTTCCAGGGACCAGGGGATAAACGGAT
GGGGGTGTCGTTTTGGCTGAGGAAACGGTGACTGAGGTTCCTTGACCCCAGTAGTCCATAGCA
TAGTAGTGGTACCTACTACCGTAGTAATTAGGCCTTGTACAGTAATAAAGGGCTGTGTCTTCA
GAGCTCACTTTGCTCATTTGCAGGTCCAGCGTATTTTTGGCGTTGTCTCTGGAGATGATGAATT
GATCCTTTAGAGATGGCGTATAGTTTATCGAAGTGCTATCTGGATTAACTTCTCCAATCCATTC
TAGCCCTTTCCCTGGAGCCTGCCGGACCCAACTCATCCAGTATCTACTAAAATCGAATCCTGA
GGTTGCACAGGAGAGTTTCAGGGATCCTCCAGGCTGCACCAGGCCACCTCCAGACTCGAGAA
GCTTCACCTCACACTGGACCCCTTTTAAAAGAGCAACAATAAAAAAAATCAGCCCAAAATCC
ATGTAAGGGCGAATTCCAGCACACTGGCGGCCGTTACTAGTGGATCCGAGCTCGGTACCAAG
CTTGGCGTAATCATGGTCATAGCTGTTTCCTGTGTGAAATTGTTATCCGCTCACAATTCCACAC
AACATACGAGCCGGAAGCATAAAGT

FIGURE 23

| Primer Name | Sequence |
|---|---|
| pCH-huBsiWI | 5' CGT GGA AGC TTC GTA CGG CCC ATC GGT CTT CCC CCT GGC A 3' |
| BGH | 5' TAG AAG GCA CAG TCG AGG 3' |
| H460-16-2 Vk 5' | 5' GCG CCA AGA TCT GAT ATC CAG ATG ACA 3' |
| Vk 3' NotI | 5' GGA GGT TGC GGC CGC AGT CCG TTA TAT TTC 3' |
| H460-16-2 Vh 5' NheI | 5' GCGGAGGCTAGCGGGGATATCCACCATGGATTTTGGGCTG 3' |
| Vh 3' BsiWI | 5' GAG TGC CGT ACG TGG AGG CTG AGG AAA CGG TGA C 3' |
| pCL-HuCK 5' MluI | 5' GCT GGC TAG CAC GCG TTA AAC ATG AAG TTT CCT TCT 3' |
| Vh 5' NheI/MluI | 5' CGC GAG GCT AGC ACG CGT ATC CAC CAT G 3' |

FIGURE 36A pNEF38 (ARH460-16-2 Vκ) # 1
ATGAAGTTTCCTTCTCAACTTCTGCTCTTACTGCTGTTTGGAATCCCAGGCATGAGATCTGATATCCAGAT
GACACAGACTACATCCTCCCTGTCTGTCTCTCTGGGAGACAGAGTCACCATCAATTGCAGGGCAAGTCAG
GACATTAACAATTATTTAAACTGGTATCAGCAGAAACCAGATGGAACTGTTAAACTCCTGATCTACTACA
CATCAAGATTACACTCAGGAGTCCCATCAAGGTTCAGTGGCAGTGGGTCTGGAACAGATTTTTCTCTCAC
CATTAGCAACCTGGAGAAAGAAGATGTTGCCACTTACTTTTGCCAACAGGGTAGTACGCTTCCATTCACG
TTCGGCTCGGGGACAAAGTTGGAAATAAAACGGACTGCGGCCGCACCATCTGTCTTCATCTTCCCGCCAT
CTGATGAGCAGTTGAA_TCTGGAACTGCCTCTGTTGTGTGCCTGCTGAATAACTTCTATCCCAGAGAGGCC
AAAGTACAGTGGAAGGTGGATAACGCCCTCCAATCGGGTAACTCCCAGGAGAGTGTCACAGAGCAGGAC
AGCAAGGACAGCACCTACAGCCTCAGCAGCACCCTGACGCTGAGCAAAGCAGACTACGAGAAACACAA
AGTCTACGCCTGCGAAGTCACCCATCAGGGCCTGAGCTCGCCCGTCACAAAGAGCTTCAACAGGGGAGA
GTGTTGA pNEF38 (ARH460-16-2 Vκ) # 2
ATGAAGTTTCCTTCTCAACTTCTGCTCTTACTGCTGTTTGGAATCCCAGGCATGAGATCTGATATCCAGAT
GACACAGACTACATCCTCCCTGTCTGTCTCTCTGGGAGACAGAGTCACCATCAATTGCAGGGCAAGTCAG
GACATTAACAATTATTTAAACTGGTATCAGCAGAAACCAGATGGAACTGTTAAACTCCTGATCTACTACA
CATCAAGATTACACTCAGGAGTCCCATCAAGGTTCAGTGGCAGTGGGTCTGGAACAGATTTTTCTCTCAC
CATTAGCAACCTGGAGAAAGAAGATGTTGCCACTTACTTTTGCCAACAGGGTAGTACGCTTCCATTCACG
TTCGGCTCGGGGACAAAGTTGGAAATAAAACGGACTGCGGCCGCACCATCTGTCTTCATCTTCCCGCCAT
CTGATGAGCAGTTGAA_TCTGGAACTGCCTCTGTTGTGTGCCTGCTGAATAACTTCTATCCCAGAGAGGCC
AAAGTACAGTGGAAGGTGGATAACGCCCTCCAATCGGGTAACTCCCAGGAGAGTGTCACAGAGCAGGAC
AGCAAGGACAGCACCTACAGCCTCAGCAGCACCCTGACGCTGAGCAAAGCAGACTACGAGAAACACAA
AGTCTACGCCTGCGAAGTCACCCATCAGGGCCTGAGCTCGCCCGTCACAAAGAGCTTCAACAGGGGAGA
GTGTTGA pNEF38 (ARH460-16-2 Vκ) # 4
ATGAAGTTTCCTTCTCAACTTCTGCTCTTACTGCTGTTTGGAATCCCAGGCATGAGATCTGATATCCAGAT
GACACAGACTACATCCTCCCTGTCTGTCTCTCTGGGAGACAGAGTCACCATCAATTGCAGGGCAAGTCAG
GACATTAACAATTATTTAAACTGGTATCAGCAGAAACCAGATGGAACTGTTAAACTCCTGATCTACTACA
CATCAAGATTACACTCAGGAGTCCCATCAAGGTTCAGTGGCAGTGGGTCTGGAACAGATTTTTCTCTCAC
CATTAGCAACCTGGAGAAAGAAGATGTTGCCACTTACTTTTGCCAACAGGGTAGTACGCTTCCATTCACG
TTCGGCTCGGGGACAAAGTTGGAAATAAAACGGACTGCGGCCGCACCATCTGTCTTCATCTTCCCGCCAT
CTGATGAGCAGTTGAAATCTGGAACTGCCTCTGTTGTGTGCCTGCTGAATAACTTCTATCCCAGAGAGGC
CAAAGTACAGTGGAAGGTGGATAACGCCCTCCAATCGGGTAACTCCCAGGAGAGTGTCACAGAGCAGGA
CAGCAAGGACAGCACCTACAGCCTCAGCAGCACCCTGACGCTGAGCAAAGCAGACTACGAGAAACACA
AAGTCTACGCCTGCGAAGTCACCCATCAGGGCCTGAGCTCGCCCGTCACAAAGAGCTTCAACAGGGGAG
AGTGTTGA pDEF38 (ARH460-16-2 V$_H$) # 1
CCATTTGGTGTCCGGCGACGGTAGCCAGGCCAGCCTGGCCATGGAAGTAATTCTTGGAATTTGCCCATTT
TGAGTTTGGAGCGAAGCTGATTGACAAAGCTGCTTAGCCGTTCAAAGGTATTCTTCGAACTTTTTTTTTAA
GGTGTTGTGAAAACCAAGCTTCTCGAGCGTACGTATTAATTAACTCACGCGTATCCACCATGGATTTTGG
GCTGATTTTTTTTATTGTTGCTCTTTTAAAAGGGGTCCAGTGTGAGGTGAAGCTTCTCGAGTCTGGAGGTG
GCCTGGTGCAGCCTGGAGGATCCCTGAAACTCTCCTGTGCAACCTCAGGATTCGATTTTAGTAGATACTG
GATGAGTTGGGTCCGGCAGGCTCCAGGGAAAGGGCTAGAATGGATTGGAGAAGTTAATCCAGATAGCAC
TTCGATAAACTATACGCCATCTCTAAAGGATCAATTCATCATCTCCAGAGACAACGCCAAAAATACGCTG
GACCTGCAAATGAGCAAAGTGAGCTCTGAAGACACAGCCCTTTATTACTGTACAAGGCCTAATTACTACG
GTAGTAGGTACCACTACTATGCTATGGACTACTGGGGTCAAGGAACCTCAGTCACCGTTTCCTCAGCCTC
CACGTACGGCCCATCGGTCTTCCCCCTGGCACCCTCCTCCAAGAGCACCTCTGGGGGCACAGCGGCCCTG
GGCTGCCTGGTCAAGGACTACTTCCCCGAACCGGTGACGGTGTCGTGGAACTCAGGCGCCCTGACCAGCG
GCGTGCACACCTTCCCGGCTGTCCTACAGTCCTCAGGACTCTACTCCCTCAGCAGCGTGGTGACCGTGCC
CTCCAGCAGCTTGGGCACCCAGACCTACATCTGCAACGTGAATCACAAGCCCAGCAACACCAAGGTGGA
CAAGAAAGTTGAGCCCAAATCTTGTGACAAAACTCACACATGCCCACCGTGCCCAGCACCTGAACTCCTG
GGGGG_ACCGTCAGTCTTCCTCTTCCCCCCAAAACCCAGGACACCCTCATGATCTCCCGGACCCCTGAGG
GCACAT pDEF38 (ARH460-16-2 V$_H$) # 2

FIGURE 36B

ATGGATTTTGGGCTGATTTTTTTTATTGTTGCTCTTTTAAAAGGGGTCCAGTGTGAGGTGAAGCTTCTCGA
GTCTGGAGGTGGCCTGGTGCAGCCTGGAGGATCCCTGAAACTCTCCTGTGCAACCTCAGGATTCGATTTT
AGTAGATACTGGATGAGTTGGGTCCGGCAGGCTCCAGGGAAAGGGCTAGAATGGATTGGAGAAGTTAAT
CCAGATAGCACTTCGATAAACTATACGCCATCTCTAAAGGATCAATTCATCATCTCCAGAGACAACGCCA
AAAATACGCTGGACCTGCAAATGAGCAAAGTGAGCTCTGAAGACACAGCCCTTTATTACTGTACAAGGC
CTAATTACTACGGTAGTAGGTACCACTACTATGCTATGGACTACTGGGGTCAAGGAACCTCAGTCACCGT
TTCCTCAGCCTCCACGTACGGCCCATCGGTCTTCCCCCTGGCACCCTCCTCCAAGAGCACCTCTGGGGGCA
CAGCGGCCCTGGGCTGCCTGGTCAAGGACTACTTCCCCGAACCGGTGACGGTGTCGTGGAACTCAGGCGC
CCTGACCAGCGGCGTGCACACCTTCCCGGCTGTCCTACAGTCCTCAGGACTCTACTCCCTCAGCAGCGTG
GTGACCGTGCCCTCCAGCAGCTTGGGCACCCAGACCTACATCTGCAACGTGAATCACAAGCCCAGCAAC
ACCAAGGTGGACAAGAAAGTTGAGCCCAAATCTTGTGACAAAACTCACACATGCCCACCGTGCCCAGCA
CCTGAACTCCTGGGGGGACCGTCAGTCTTCCTCTTCCCCCCAAAACCCAAGGACACCCTCATGATCTCCC
GGACCCCTGAGGTCACATGCGTGGTGGTGGACGTGAGCCACGAAGACCCTGAGGTCAAGTTCAACTGGT
ACGTGGACGGCGTGGAGGTGCATAATGCCAAGACAAAGCCGCGGGAGGAGCAGTACAACAGCACGTAC
CGTGTGGTCAGCGTCCTCACCGTCCTGCACCAGGACTGGCTGAATGGCAAGGAGTACAAGTGCAAGGTCT
CCAACAAAGCCCTCCCAGCCCCCATCGAGAAAACCATCTCCAAAGCCAAAGGGCAGCCCCGAGAACCAC
AGGTGTACACCCTGCCCCCATCCCGGGATGAGCTGACCAAGAACCAGGTCAGCCTGACCTGCCTGGTCAA
AGGCTTCTATCCCAGCGACATCGCCGTGGAGTGGGAGAGCAATGGGCAGCCGGAGAACAACTACAAGAC
CACGCCTCCCGTGCTGGACTCCGACGGCTCCTTCTTCCTCTACAGCAAGCTCACCGTGGACAAGAGCAGG
TGGCAGCAGGGGAACGTCTTCTCATGCTCCGTGATGCATGAGGCTCTGCACAACCACTACACGCAGAAG
AGCCTCCCCCTGTCTCCGGGTAAATGACTCGAGCATGCATCTAGAATATTACCCCTAACACCTGCCACCC
AGTCTTAATCAGTGGTGGAAGAACGGTCTCAGAACTGTTTGTCTCAATTGGCCATTTAAGTTTATAGTGA
AGACTGGTTAATGATAACAATGCATCGGAAACCTTCAGGAGGAAAGGAGAATGTTTGTGGAACAAT pDEF38 (ARH460-16-2 V_H) #6

CACATTTGGTGGGCTGGAGACTGTAGCCAGGCCAGCCTGGCCATGGAAGTAATTCTTGGAATTTGCCCAT
TTTGAGTTTGGAGCGAAGCTGATTGACAAAGCTGCTTAGCCGTTCAAAGGTATTCTTCGAACTTTTTTTTT
AAGGTGTTGTGAAAACCAAGCTTCTCGAGCGTACGTATTAATTAACTCACGCGTATCCACCATGGATTTT
GGGCTGATTTTTTTTATTGTTGCTCTTTTAAAAGGGGTCCAGTGTGAGGTGAAGCTTCTCGAGTCTGGAGG
TGGCCTGGTGCAGCCTGGAGGATCCCTGAAACTCTCCTGTGCAACCTCAGGATTCGATTTTAGTAGATAC
TGGATGAGTTGGGTCCGGCAGGCTCCAGGGAAAGGGCTAGAATGGATTGGAGAAGTTAATCCAGATAGC
ACTTCGATAAACTATACGCCATCTCTAAAGGATCAATTCATCATCTCCAGAGACAACGCCAAAAATACGC
TGGACCTGCAAATGAGCAAAGTGAGCTCTGAAGACACAGCCCTTTATTACTGTACAAGGCCTAATTACTA
CGGTAGTAGGTACCACTACTATGCTATGGACTACTGGGGTCAAGGAACCTCAGTCACCGTTTCCTCAGCC
TCCACGTACGGCCCATCGGTCTTCCCCCTGGCACCCTCCTCCAAGAGCACCTCTGGGGGCACAGCGGCCC
TGGGCTGCCTGGTCAAGGACTACTTCCCCGAACCGGTGACGGTGTCGTGGAACTCAGGCGCCCTGACCAG
CGGCGTGCACACCTTCCCGGCTGTCCTACAGTCCTCAGGACTCTACTCCCTCAGCAGCGTGGTGACCGTG
CCCTCCAGCAGCTTGGGCACCCAGACCTACATCTGCAACGTGAATCACAAGCCCAGCAACACCAAGGTG
GACAAGAAGTTGAGCCCAAATCTTGTGACAAAACTCACACATGCCCACCGTGCCAGCACCTGAACTCCTG
GGGGGAC

FIGURE 39

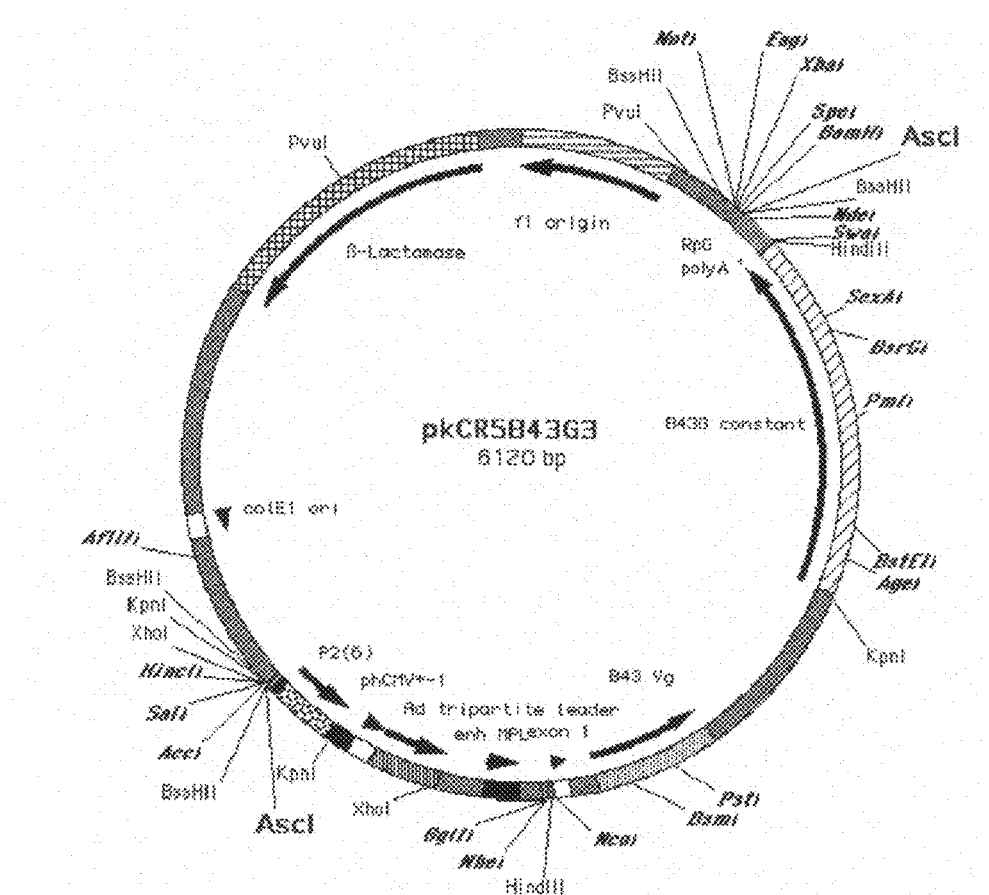

PkP2(6)B43G3: 6120bp
Constructed by: Penny Harakidas
in the laboratory of Bernard Massie
The chimeric B43 Gamma Heavy Chain is under the control of the inducible cumate
promoter P2(6) and is followed by the Rabbit Beta-Globin polyadenylation signal. Contains
β-lactamase gene for ampicillin resistance in E. coli.

f1 origin: 458-1
Rabbit β-Globin Poly A signal: 809-708
Human Gamma 3 Heavy Chain constant domain: 2466 and 1909-822
Human Kappa Gene Intron: 2465-1910
B43 Gamma variable domain: 2820-2467
Leader Exon 2: 2831-2821
Leader Intron: 2913-2832
Leader Exon 1: 2959-2914
Kozak's Leader: 1518-1463
Enhancer MLP: 1706-1606
Adenovirus Tripartite Leader: 2047-1843
pH CMV*-1: 2122-2056
P2(6): 2388-2197
ColE1 origin of replication: 4440-4368
β-lactamase gene: 5992-5132

H: heavy chain
L: light chain

H: heavy chain
L: light chain

FIGURE 43

Arvarlc
5'-cgg ggg atc cgc cgc cac cat ggt atc ctc acc tca g-3' jctvar-k#3
5'-gac aga tgg tgc agc cac agt ccg ttt tat ttc caa ctt tg-3'

Arkappa
5'-cgg ggg atc cct aac act ctc ccc tgt tga agc-3' jctk-var#3
5'-caa agt tgg aaa taa aac gga ctg tgg ctg cac cat ctg tc-3'

Arjctvar-k
5'-gac aga tgg tgc agc cac agt tgc ggc cgc agt ccg ttt ta-3'

Arjctk-var
5'-taa aac gga ctg cgg ccg caa ctg tgg ctg cac cat ctg tc-3'

Arigg2
5'-cat ggg ggc cct tgg tgg agc cgt acg tgg agg ctg a-3'

Arhvarswa
5'-cta ggg ggc cca ttt aaa tcg ccg cca cca tgg att ttg ggc tg

ApaICR5
5'-gga aca aaa gct ggg tac cgg gcc ccc cct cga ggt c-3'

IgG2TVSSASTK
5'-ccg atg ggc cct tgg tgg aag ctg agg aaa cgg tga c-3'

FIGURE 48
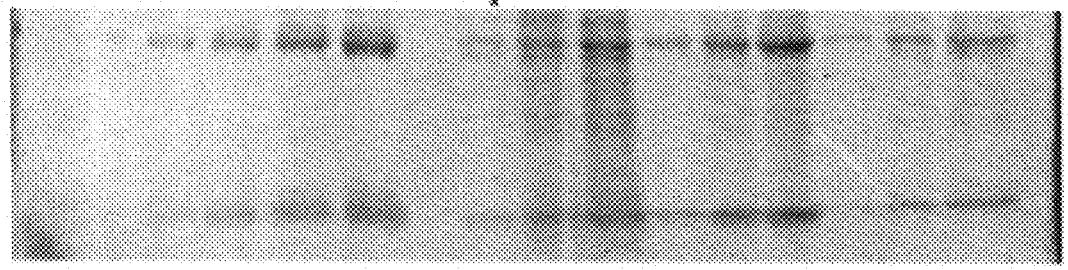
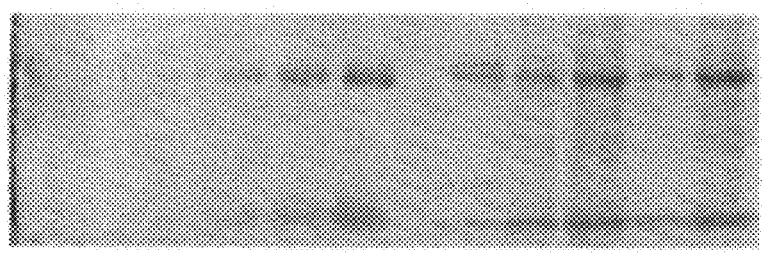

FIGURE 52

| | Untreated | Murine H460-16-2 Concentration in µg/mL | | | Chimerized Antibody | | | | | | | Positive Control Camptothecin |
|---|---|---|---|---|---|---|---|---|---|---|---|---|
| | | | | | (ch)ARH460-16-2-IgG1 Concentration in µg/mL | | | (ch)ARH460-16-2-IgG2 Concentration in µg/mL | | | | |
| | | 0.25 | 2.5 | 20 | 0.25 | 2.5 | 20 | 0.25 | 2.5 | 20 | | 2 µM |
| Experiment 1 | 7.63 | 24.05 | 38.95 | 41.37 | 34.10 | 45.86 | 58.43 | 50.74 | 57.81 | 68.72 | | 37.53 |
| Experiment 2 | 9.44 | 12.21 | 18.19 | 22.15 | 25.43 | 37.79 | 20.58 | 33.46 | 31.99 | 43.69 | | 36.82 |
| Average Total Apoptosis | 8.54 | 18.13 | 28.57 | 31.76 | 29.76 | 41.83 | 39.51 | 42.10 | 44.90 | 56.20 | | 37.17 |
| Average Standard Deviation | 1.28 | 8.38 | 14.68 | 13.59 | 6.13 | 5.71 | 26.76 | 12.22 | 18.26 | 17.70 | | 0.50 |

| | 1B7.11 Concentration in µg/mL | | | Isotyp Control Antibodies | | | | | | |
|---|---|---|---|---|---|---|---|---|---|---|
| | | | | anti-hu IgG1 Concentration in µg/mL | | | anti-hu IgG2 Concentration in µg/mL | | | |
| | 0.25 | 2.5 | 20 | 0.25 | 2.5 | 20 | 0.25 | 2.5 | 20 | |
| Experiment 1 | 10.37 | 11.75 | 13.79 | 13.77 | 11.64 | 12.19 | 14.32 | 12.67 | 11.24 | |
| Experiment 2 | 9.33 | 10.23 | 5.22 | 12.06 | 10.29 | 10.71 | 10.53 | 10.72 | 12.57 | |
| Average Total Apoptosis | 9.85 | 10.99 | 9.51 | 12.92 | 10.97 | 11.45 | 12.43 | 11.70 | 11.91 | |
| Average Standard Deviation | 0.74 | 1.08 | 6.06 | 1.21 | 0.95 | 1.05 | 2.68 | 1.38 | 0.95 | |

CYTOTOXICITY MEDIATION OF CELLS EVIDENCING SURFACE EXPRESSION OF CD44

REFERENCE TO RELATED APPLICATIONS

This application is a continuation-in-part to U.S. patent application Ser. No. 10/810,165 filed Mar. 26, 2004, now abandoned, which is a continuation-in-part to U.S. patent application Ser. No. 10/647,818 filed Aug. 22, 2003, now U.S. Pat. No. 7,189,397, which is a continuation-in-part to U.S. patent application Ser. No. 10/603,000, filed Jun. 23, 2003, now U.S. Pat. No. 7,252,821, which is a continuation-in-part to U.S. patent application Ser. No. 09/727,361, filed Nov. 29, 2000, now U.S. Pat. No. 6,657,048, which is a continuation-in-part to U.S. patent application Ser. No. 09/415,278, filed Oct. 8, 1999, now U.S. Pat. No. 6,180,357 B1, the contents of each of which are herein incorporated by reference.

FIELD OF THE INVENTION

This invention relates to the diagnosis and treatment of cancerous diseases, particularly to the mediation of cytotoxicity of tumor cells; and most particularly to the use of cancerous disease modifying antibodies (CDMAB), optionally in combination with one or more chemotherapeutic agents, as a means for initiating the cytotoxic response. The invention further relates to binding assays, which utilize the CDMAB of the instant invention

BACKGROUND OF THE INVENTION

CD44 in Cancer: Raising monoclonal antibodies against human white blood cells led to the discovery of the CD44 antigen; a single chain hyaluronic acid (HA) binding glycoprotein expressed on a wide variety of normal tissue and on all types of hematopoietic cells. It was originally associated with lymphocyte activation and homing. Currently, its putative physiological role also includes activation of inflammatory genes, modulation of cell cycle, induction of cell proliferation, induction of differentiation and development, induction of cytoskeletal reorganization and cell migration and cell survival/resistance to apoptosis.

In humans, the single gene copy of CD44 is located on the short arm of chromosome 11, 11p13. The gene contains 19 exons; the first 5 are constant, the next 9 are variant, the following 3 are constant and the final 2 are variant. Differential splicing can lead to over 1000 different isoforms. However, currently only several dozen naturally occurring variants have been identified.

The CD44 standard glycoprotein consists of a N-terminal extracellular (including a 20 a.a. leader sequence, and a membrane proximal region (85 a.a.)) domain (270 a.a.), a transmembrane region (21 a.a.) and a cytoplasmic tail (72 a.a.). The extracellular region also contains a link module at the N-terminus. This region is 92 a.a. in length and shows homology to other HA binding link proteins. There is high homology between the mouse and human forms of CD44. The variant forms of the protein are inserted to the carboxy terminus of exon 5 and are located extracellularly when expressed.

A serum soluble form of CD44 also occurs naturally and can arise from either a stop codon (within the variable region) or from proteolytic activity. Activation of cells from a variety of stimuli including TNF-α results in shedding of the CD44 receptor. Shedding of the receptor has also been seen with tumor cells and can result in an increase in the human serum concentration of CD44 by up to 10-fold. High CD44 serum concentration suggests malignancy (ovarian cancer being the exception).

The standard form of CD44 exists with a molecular weight of approximately 37 kD. Post-translational modifications increase the molecular weight to 80-90 kD. These modifications include amino terminus extracellular domain N-linked glycosylations at asparagine residues, O-linked glycosylations at serine/threonine residues at the carboxy terminus of the extracellular domain and glycosaminoglycan additions. Splice variants can range in size from 80-250 kD.

HA, a polysaccharide located on the extracellular matrix (ECM) in mammals, is thought to be the primary CD44 ligand. However, CD44 has also been found to bind such proteins as collagen, fibronectin, laminin etc. There appears to be a correlation between HA binding and glycosylation. Inactive CD44 (does not bind HA) has the highest levels of glycosylation, active CD44 (binding HA) the lowest while inducible CD44 (does not or weakly binds HA unless activated by cytokines, monoclonal antibodies, growth factors, etc.) has glycoslyation levels somewhere in between the active and inactive forms.

CD44 can mediate some of its functions through signal transduction pathways that depend on the interaction of the cell, stimulus and the environment. Some of these pathways include the NFκB signaling cascade (involved in the inflammatory response), the Ras-MAPK signal transduction pathway (involved with activating cell cycling and proliferation), the Rho family of proteins (involved with cytoskeleton reorganization and cell migration) and the P13-K-related signaling pathway (related to cell survival). All of the above-mentioned functions are closely associated with tumor disease initiation and progression. CD44 has also been implicated in playing a role in cancer through a variety of additional mechanisms. These include the presentation of growth factors, chemokines and cytokines by cell surface proteoglycans present on the cell surface of CD44 to receptors involved in malignancy. Also, the intracellular degradation of HA by lysosomal hyaluronidases after internalization of the CD44-HA complex can potentially increase the likelihood of tumor invasiveness and induction of angiogenesis through the ECM. In addition, the transmission of survival or apoptotic signals has been shown to occur through either the standard or variable CD44 receptor. CD44 has also been suggested to be involved in cell differentiation and migration. Many, if not all, of these mechanisms are environment and cell dependent and several give rise to variable findings. Therefore, more research is required before any conclusions can be drawn.

In order to validate a potential functional role of CD44 in cancer, expression studies of CD44 were undertaken to determine if differential expression of the receptor correlates with disease progression. However, inconsistent findings were observed in a majority of tumor types and this is probably due to a combination of reagents, technique, pathological scoring and cell type differences between researchers. Renal cell carcinoma and non-Hodgkin's lymphoma appear to be the exception in that patients with high CD44 expressing tumors consistently had shorter survival times than their low or non-CD44 expressing counterparts.

Due to its association with cancer, CD44 has been the target of the development of anti-cancer therapeutics. There is still controversy as to whether the standard or the variant forms of CD44 are required for tumor progression. There is in vivo animal data to support both views and again it may be tumor type and even cell type dependent. Different therapeutic approaches have included injection of soluble CD44 proteins, hyaluronan synthase cDNA, hyaluronidase, the use of CD44 anti sense and CD44 specific antibodies. Each approach has led to some degree of success thereby providing support for anti-CD44 cancer therapeutics.

Both variant and standard CD44 specific monoclonal antibodies have been generated experimentally but for the most part these antibodies have no intrinsic biological activity, rather they bind specifically to the type of CD44 they recognize. However, there are some that are either active in vitro or in vivo but generally not both. Several anti-CD44 antibodies have been shown to mediate cellular events. For example the murine antibody A3D8, directed against human erythrocyte Lutheran antigen CD44 standard form, was shown to enhance CD2 (9-1 antibody) and CD3 (OKT3 antibody) mediated T cell activation; another anti-CD44 antibody had similar effects. A3D8 also induced IL-1 release from monocytes and IL-2 release from T lymphocytes. Interestingly, the use of A3D8 in conjunction with drugs such as daunorubicin, mitoxantrone and etoposide inhibited apoptosis induction in HL60 and NB4 AML cells by abrogating the generation of the second messenger ceramide. The J173 antibody, which does not have intrinsic activity and is directed against a similar epitope of CD44s, did not inhibit drug-induced apoptosis. The NIH44-1 antibody, directed against an 85-110 kD and 200 kD form of CD44, augmented T-cell proliferation through a pathway the authors speculated as either cross-linking or aggregation of CD44. Taken together, there is no evidence that antibodies such as these are suitable for use as cancer therapeutics since they either are not directed against cancer (e.g. activate lymphocytes), induce cell proliferation, or when used with cytotoxic agents inhibited drug-induced death of cancer cells.

Several anti-CD44 antibodies have been described which demonstrate anti-tumor effects in vivo. The antibody 1.1ASML, a mouse IgG1 directed to the v6 variant of CD44, has been shown to decrease the lymph node and lung metastases of the rat pancreatic adenocarcinoma BSp73ASML. Survival of the treated animals was concomitantly increased. The antibody was only effective if administered before lymph node colonization, and was postulated to interfere with cell proliferation in the lymph node. There was no direct cytototoxicity of the antibody on the tumor cells in vitro, and the antibody did not enhance complement-mediated cytotoxicity, or immune effector cell function. Utility of the antibody against human cells was not described.

Breyer et al. described the use of a commercially-available antibody to CD44s to disrupt the progression of an orthotopically-implanted rat glioblastoma. The rat glioblastoma cell line C6 was implanted in the frontal lobe, and after 1 week, the rats were given 3 treatments with antibody by intracerebral injection. Treated rats demonstrated decreased tumor growth, and higher body weight than buffer or isotype control treated rats. The antibody was able to inhibit adhesion of cells in vitro to coverslips coated with extracellular matrix components, but did not have any direct cytotoxic effects on cells. This antibody was not tested against human cells.

A study was carried out which compared the efficacy of an antibody to CD44s (IM-7.8.1) to an antibody to CD44v 10 (K926). The highly metastatic murine melanoma line B16F10, which expresses both CD44 isoforms, was implanted intravenously into mice. After 2 days, antibodies were given every third day for the duration of the study. Both antibodies caused a significant reduction of greater than 50% in the number of lung metastases; there was no significant difference in efficacy between the two antibodies. The antibody did not affect proliferation in vitro, and the authors, Zawadzki et al., speculated that the inhibition of tumor growth was due to the antibody blocking the interaction of CD44 with its ligand. In another study using IM-7.8.1, Zahalka et al. demonstrated that the antibody and its F(ab')$_2$ fragment were able to block the lymph node infiltration by the murine T-cell lymphoma LB. This conferred a significant survival benefit to the mice. Wallach-Dayan et al. showed that transfection of LB-TRs murine lymphoma, which does not spontaneously form tumors, with CD44v4-v10 conferred the ability to form tumors. IM-7.8.1 administration decreased tumor size of the implanted transfected cells in comparison to the isotype control antibody. None of these studies demonstrated human utility for this antibody.

GKW.A3, a mouse IgG2a, is specific for human CD44 and prevents the formation and metastases of a human melanoma xenograft in SCID mice. The antibody was mixed with the metastastic human cell line SMMU-2, and then injected subcutaneously. Treatments were continued for the following 3 weeks. After 4 weeks, only 1 of 10 mice developed a tumor at the injection site, compared to 100 percent of untreated animals. F(ab')$_2$ fragments of the antibody demonstrated the same inhibition of tumor formation, suggesting that the mechanism of action was not dependent on complement or antibody-dependent cellular cytotoxicity. If the tumor cells were injected one week prior to the first antibody injection, 80 percent of the animals developed tumors at the primary site. However, it was noted that the survival time was still significantly increased. Although the delayed antibody administration had no effect on the primary tumor formation, it completely prevented the metastases to the lung, kidney, adrenal gland, liver and peritoneum that were present in the untreated animals. This antibody does not have any direct cytotoxicity on the cell line in vitro nor does it interfere with proliferation of SMMU-2 cells, and appears to have its major effect on tumor formation by affecting metastasis or growth. One notable feature of this antibody was that it recognized all isoforms of CD44, which suggests limited possibilities for therapeutic use.

Strobel et al. describe the use of an anti-CD44 antibody (clone 515) to inhibit the peritoneal implantation of human ovarian cancer cells in a mouse xenograft model. The human ovarian cell line 36M2 was implanted intraperitoneally into mice in the presence of the anti-CD44 antibody or control antibody, and then treatments were administered over the next 20 days. After 5 weeks, there were significantly fewer nodules in the peritoneal cavity in the antibody treated group. The nodules from both the anti-CD44 and control treated groups were the same size, suggesting that once the cells had implanted, the antibody had no effect on tumor growth. When cells were implanted subcutaneously, there was also no effect on tumor growth, indicating that the antibody itself did not have an anti-proliferative or cytotoxic effect. In addition, there was no effect of the antibody on cell growth in vitro.

VFF-18, also designated as BIWA 1, is a high-affinity antibody to the v6 variant of CD44 specific for the 360-370 region of the polypeptide. This antibody has been used as a $^{99m}$Technetium-labelled conjugate in a Phase 1 clinical trial in 12 patients. The antibody was tested for safety and targeting potential in patients with squamous cell carcinoma of the head and neck. Forty hours after injection, 14 percent of the injected dose was taken up by the tumor, with minimal accumulation in other organs including the kidney, spleen and bone marrow. The highly selective tumor binding suggests a role for this antibody in radioimmunotherapy, although the exceptionally high affinity of this antibody prevented penetration into the deeper layers of the tumor. Further limiting the application of BIWA 1 is the immunogenicity of the murine antibody (11 of 12 patients developed human anti-mouse antibodies (HAMA)), heterogenous accumulation throughout the tumor and formation of antibody-soluble CD44 complexes. WO 02/094879 discloses a humanized version of VFF-18 designed to overcome the HAMA response, designated BIWA 4. BIWA 4 was found to have a significantly lower antigen binding affinity than the parent VFF 18 antibody. Surprisingly, the lower affinity BIWA 4 antibody had superior tumor uptake characteristics than the higher affinity BIWA 8 humanized VFF-18 antibody. Both $^{99m}$Technetium-labelled and $^{186}$Rhenium-labelled BIWA 4 antibodies were assessed in a 33 patient Phase 1 clinical trial to determine safety, tolerability, tumor accumulation and maximum tolerated dose, in the case of $^{186}$Re-labelled BIWA 4. There appeared to be tumor related uptake of $^{99m}$Tc-labelled BIWA 4. There were no tumor responses seen with all doses of $^{186}$Re-labelled BIWA 4, although a number had stable disease; the dose limiting toxicity occurred at 60 mCi/m$^2$. There was a 50-65 percent rate of adverse events with 12 of 33 patients deemed to have serious adverse events (thrombocytopenia, leucopenia and fever) and of those 6, all treated with $^{186}$Re-labelled BIWA 4, died in the course of treatment or follow-up due to disease progression. Two patients developed human anti-human antibodies (HAHA). A Phase 1 dose escalation trial of $^{186}$Re-labelled BIWA 4 was carried out in 20 patients. Oral mucositis and dose-limiting thrombocytopenia and leucocytopenia were observed; one patient developed a HAHA response. Stable disease was seen in 5 patients treated at the highest dose of 60 mCi/m$^2$. Although deemed to be acceptable in both safety and tolerablility for the efficacy achieved, these studies have higher rates of adverse events compared to other non-radioisotope conjugated biological therapies in clinical studies. U.S. Patent Application US 2003/0103985 discloses a humanized version of VFF-18 conjugated to a maytansinoid, designated BIWI 1, for use in tumor therapy. A humanized VFF 18 antibody, BIWA 4, when conjugated to a toxin, i.e. BIWI 1, was found to have significant anti-tumor effects in mouse models of human epidermoid carcinoma of the vulva, squamous cell carcinoma of the pharynx or breast carcinoma. The unconjugated version, BIWA 4, did not have anti-tumor effects and the conjugated version, BIWI 1, has no evidence of safety or efficacy in humans.

Mab U36 is a murine monoclonal IgG1 antibody generated by UM-SCC-22B human hypopharyngeal carcinoma cell immunization and selection for cancer and tissue specificity. Antigen characterization through cDNA cloning and sequence analysis identified the v6 domain of keratinocyte-specific CD44 splice variant epican as the target of Mab U36. Immunohistochemistry studies show the epitope to be restricted to the cell membrane. Furthermore, Mab U36 labeled 94 percent of the head and neck squamous cell carcinomas (HNSCC) strongly, and within these tumors there was uniformity in cell staining. A 10 patient $^{99m}$Tc-labelled Mab U36 study showed selective accumulation of the antibody to HNSCC cancers (20.4±12.4 percent injected dose/kg at 2 days); no adverse effects were reported but two patients developed HAMA. In a study of radio-iodinated murine Mab U36 there were 3 cases of HAMA in 18 patients and selective homogenous uptake in HNSCC. In order to decrease the antigenicity of Mab U36 and decrease the rate of HAMA a chimeric antibody was constructed. Neither the chimeric nor the original murine Mab U36 has ADCC activity. There is no evidence of native functional activity of Mab U36. $^{186}$Re-labelled chimeric Mab U36 was used to determine the utility of Mab U36 as a therapeutic agent. In this Phase 1 escalating dose trial 13 patients received a scouting dose of $^{99m}$Tc-labelled chimeric Mab U36 followed by $^{186}$Re-labelled chimeric Mab U36. There were no acute adverse events reported but following treatment dose limiting myelotoxcity (1.5 GBq/m$^2$) in 2 of 3 patients, and thrombocytopenia in one patient treated with the maximum tolerated dose (1.0 GBq/m$^2$) were observed. Although there were some effects on tumor size these effects did not fulfill the criteria for objective responses to treatment. A further study of $^{186}$Re-labelled chimeric Mab U36 employed a strategy of using granulocyte colony-stimulating factor stimulated whole blood reinfusion to double the maximum-tolerated activity to 2.8 Gy. In this study of nine patients with various tumors of the head and neck, 3 required transfusions for drug related anemia. Other toxicity includes grade 3 myelotoxicity, and grade 2 mucositis. No objective tumor responses were reported although stable disease was achieved for 3-5 months in 5 patients. Thus, it can be seen that although Mab U36 is a highly specific antibody the disadvantage of requiring a radioimmunoconjugate to achieve anti-cancer effects limits its usefulness because of the toxicity associated with the therapy in relation to the clinical effects achieved.

To summarize, a CD44v6 (1.1ASML) and CD44v10 (K926) monoclonal antibody have been shown to reduce metastatic activity in rats injected with a metastatic pancreatic adenocarcinoma or mice injected with a malignant melanoma respectively. Another anti-CD44v6 antibody (VFF-18 and its derivatives), only when conjugated to a maytansinoid or a radioisotope, has been shown to have anti-tumor effects. Anti-standard CD44 monoclonal antibodies have also been shown to suppress intracerebral progression by rat glioblastoma (anti-CD44s), lymph node invasion by mouse T cell lymphoma (IM-7.8.1) as well as inhibit implantation of a human ovarian cancer cell line in nude mice (clone 515), lung metastasis of a mouse melanoma cell line (IM-7.8.1) and metastasis of a human melanoma cell line in SCID mice (GKW.A3). The radioisotope conjugated Mab U36 anti-CD44v6 antibody and its derivatives had anti-tumor activity in clinical trials that were accompanied by significant toxicity. These results, though they are encouraging and support the development of anti-CD44 monoclonal antibodies as potential cancer therapeutics, demonstrate limited effectiveness, safety, or applicability to human cancers.

Thus, if an antibody composition were isolated which mediated cancerous cell cytotoxicity, as a function of its attraction to cell surface expression of CD44 on said cells, a valuable diagnostic and therapeutic procedure would be realized.

Monoclonal Antibodies as Cancer Therapy: Each individual who presents with cancer is unique and has a cancer that is as different from other cancers as that person's identity. Despite this, current therapy treats all patients with the same type of cancer, at the same stage, in the same way. At least 30% of these patients will fail the first line therapy, thus leading to further rounds of treatment and the increased probability of treatment failure, metastases, and ultimately, death. A superior approach to treatment would be the customization of therapy for the particular individual. The only current therapy which lends itself to customization is surgery. Chemotherapy and radiation treatment cannot be tailored to the patient, and surgery by itself, in most cases is inadequate for producing cures.

With the advent of monoclonal antibodies, the possibility of developing methods for customized therapy became more realistic since each antibody can be directed to a single epitope. Furthermore, it is possible to produce a combination of antibodies that are directed to the constellation of epitopes that uniquely define a particular individual's tumor.

Having recognized that a significant difference between cancerous and normal cells is that cancerous cells contain antigens that are specific to transformed cells, the scientific community has long held that monoclonal antibodies can be designed to specifically target transformed cells by binding specifically to these cancer antigens; thus giving rise to the belief that monoclonal antibodies can serve as "Magic Bullets" to eliminate cancer cells. However, it is now widely recognized that no single monoclonal antibody can serve in all instances of cancer, and that monoclonal antibodies can be deployed, as a class, as targeted cancer treatments. Monoclonal antibodies isolated in accordance with the teachings of the instantly disclosed invention have been shown to modify the cancerous disease process in a manner which is beneficial to the patient, for example by reducing the tumor burden, and will variously be referred to herein as cancerous disease modifying antibodies (CDMAB) or "anti-cancer" antibodies.

At the present time, the cancer patient usually has few options of treatment. The regimented approach to cancer therapy has produced improvements in global survival and morbidity rates. However, to the particular individual, these improved statistics do not necessarily correlate with an improvement in their personal situation.

Thus, if a methodology was put forth which enabled the practitioner to treat each tumor independently of other patients in the same cohort, this would permit the unique approach of tailoring therapy to just that one person. Such a course of therapy would, ideally, increase the rate of cures, and produce better outcomes, thereby satisfying a long-felt need.

Historically, the use of polyclonal antibodies has been used with limited success in the treatment of human cancers. Lymphomas and leukemias have been treated with human plasma, but there were few prolonged remission or responses. Furthermore, there was a lack of reproducibility and there was no additional benefit compared to chemotherapy. Solid tumors such as breast cancers, melanomas and renal cell carcinomas have also been treated with human blood, chimpanzee serum, human plasma and horse serum with correspondingly unpredictable and ineffective results.

There have been many clinical trials of monoclonal antibodies for solid tumors. In the 1980s there were at least four clinical trials for human breast cancer which produced only one responder from at least 47 patients using antibodies against specific antigens or based on tissue selectivity. It was not until 1998 that there was a successful clinical trial using a humanized anti-Her2/neu antibody (HERCEPTIN®) in combination with Cisplatin. In this trial 37 patients were assessed for responses of which about a quarter had a partial response rate and an additional quarter had minor or stable disease progression. The median time to progression among the responders was 8.4 months with median response duration of 5.3 months.

HERCEPTIN® was approved in 1998 for first line use in combination with TAXOL®. Clinical study results showed an increase in the median time to disease progression for those who received antibody therapy plus TAXOL® (6.9 months) in comparison to the group that received TAXOL® alone (3.0 months). There was also a slight increase in median survival; 22 versus 18 months for the HERCEPTIN® plus TAXOL® treatment arm versus the TAXOL® treatment alone arm. In addition, there was an increase in the number of both complete (8 versus 2 percent) and partial responders (34 versus 15 percent) in the antibody plus TAXOL® combination group in comparison to TAXOL® alone. However, treatment with HERCEPTIN® and TAXOL® led to a higher incidence of cardiotoxicity in comparison to TAXOL® treatment alone (13 versus 1 percent respectively). Also, HERCEPTIN® therapy was only effective for patients who over express (as determined through immunohistochemistry (IHC) analysis) the human epidermal growth factor receptor 2 (Her2/neu), a receptor, which currently has no known function or biologically important ligand; approximately 25 percent of patients who have metastatic breast cancer. Therefore, there is still a large unmet need for patients with breast cancer. Even those who can benefit from HERCEPTIN® treatment would still require chemotherapy and consequently would still have to deal with, at least to some degree, the side effects of this kind of treatment.

The clinical trials investigating colorectal cancer involve antibodies against both glycoprotein and glycolipid targets. Antibodies such as 17-1A, which has some specificity for adenocarcinomas, has undergone Phase 2 clinical trials in over 60 patients with only 1 patient having a partial response. In other trials, use of 17-1A produced only 1 complete response and 2 minutesor responses among 52 patients in protocols using additional cyclophosphamide. To date, Phase III clinical trials of 17-1A have not demonstrated improved efficacy as adjuvant therapy for stage III colon cancer. The use of a humanized murine monoclonal antibody initially approved for imaging also did not produce tumor regression.

Only recently have there been any positive results from colorectal cancer clinical studies with the use of monoclonal antibodies. In 2004, ERBITUX® was approved for the second line treatment of patients with EGFR-expressing metastatic colorectal cancer who are refractory to irinotecan-based chemotherapy. Results from both a two-arm Phase II clinical study and a single arm study showed that ERBITUX® in combination with irinotecan had a response rate of 23 and 15 percent respectively with a median time to disease progression of 4.1 and 6.5 months respectively. Results from the same two-arm Phase II clinical study and another single arm study showed that treatment with ERBITUX® alone resulted in an 11 and 9 percent response rate respectively with a median time to disease progression of 1.5 and 4.2 months respectively.

Consequently in both Switzerland and the United States, ERBITUX® treatment in combination with irinotecan, and in the United States, ERBITUX® treatment alone, has been approved as a second line treatment of colon cancer patients who have failed first line irinotecan therapy. Therefore, like HERCEPTIN®, treatment in Switzerland is only approved as a combination of monoclonal antibody and chemotherapy. In addition, treatment in both Switzerland and the US is only approved for patients as a second line therapy. Also, in 2004, AVASTIN® was approved for use in combination with intravenous 5-fluorouracil-based chemotherapy as a first line treatment of metastatic colorectal cancer. Phase III clinical study results demonstrated a prolongation in the median survival of patients treated with AVASTIN® plus 5-fluorouracil compared to patients treated with 5-fluourouracil alone (20 months versus 16 months respectively). However, again like HERCEPTIN® and ERBITUX®, treatment is only approved as a combination of monoclonal antibody and chemotherapy.

There also continues to be poor results for lung, brain, ovarian, pancreatic, prostate, and stomach cancer. The most promising recent results for non-small cell lung cancer came from a Phase II clinical trial where treatment involved a monoclonal antibody (SGN-15; dox-BR96, anti-Sialyl-LeX) conjugated to the cell-killing drug doxorubicin in combination with the chemotherapeutic agent TAXOTERE®. TAXOTERE® is the only FDA approved chemotherapy for the second line treatment of lung cancer. Initial data indicate an improved overall survival compared to TAXOTERE® alone. Out of the 62 patients who were recruited for the study, two-thirds received SGN-15 in combination with TAXO- TERE® while the remaining one-third received TAXOTERE® alone. For the patients receiving SGN-15 in combination with TAXOTERE®, median overall survival was 7.3 months in comparison to 5.9 months for patients receiving TAXOTERE® alone. Overall survival at 1 year and 18 months was 29 and 18 percent respectively for patients receiving SNG-15 plus TAXOTERE® compared to 24 and 8 percent respectively for patients receiving TAXOTERE® alone. Further clinical trials are planned.

Preclinically, there has been some limited success in the use of monoclonal antibodies for melanoma. Very few of these antibodies have reached clinical trials and to date none have been approved or demonstrated favorable results in Phase III clinical trials.

The discovery of new drugs to treat disease is hindered by the lack of identification of relevant targets among the products of 30,000 known genes that unambiguously contribute to disease pathogenesis. In oncology research, potential drug targets are often selected simply due to the fact that they are over-expressed in tumor cells. Targets thus identified are then screened for interaction with a multitude of compounds. In the case of potential antibody therapies, these candidate compounds are usually derived from traditional methods of monoclonal antibody generation according to the fundamental principles laid down by Kohler and Milstein (1975, Nature, 256, 495-497, Kohler and Milstein). Spleen cells are collected from mice immunized with antigen (e.g. whole cells, cell fractions, purified antigen) and fused with immortalized hybridoma partners. The resulting hybridomas are screened and selected for secretion of antibodies which bind most avidly to the target. Many therapeutic and diagnostic antibodies directed against cancer cells, including HERCEPTIN® and RITUXIMAB, have been produced using these methods and selected on the basis of their affinity. The flaws in this strategy are twofold. Firstly, the choice of appropriate targets for therapeutic or diagnostic antibody binding is limited by the paucity of knowledge surrounding tissue specific carcinogenic processes and the resulting simplistic methods, such as selection by overexpression, by which these targets are identified. Secondly, the assumption that the drug molecule that binds to the receptor with the greatest affinity usually has the highest probability for initiating or inhibiting a signal may not always be the case.

Despite some progress with the treatment of breast and colon cancer, the identification and development of efficacious antibody therapies, either as single agents or co-treatments, has been inadequate for all types of cancer.

Prior Patents

U.S. Pat. No. 5,750,102 discloses a process wherein cells from a patient's tumor are transfected with MHC genes, which may be cloned from cells or tissue from the patient. These transfected cells are then used to vaccinate the patient.

U.S. Pat. No. 4,861,581 discloses a process comprising the steps of obtaining monoclonal antibodies that are specific to an internal cellular component of neoplastic and normal cells of the mammal but not to external components, labeling the monoclonal antibody, contacting the labeled antibody with tissue of a mammal that has received therapy to kill neoplastic cells, and determining the effectiveness of therapy by measuring the binding of the labeled antibody to the internal cellular component of the degenerating neoplastic cells. In preparing antibodies directed to human intracellular antigens, the patentee recognizes that malignant cells represent a convenient source of such antigens.

U.S. Pat. No. 5,171,665 provides a novel antibody and method for its production. Specifically, the patent teaches formation of a monoclonal antibody which has the property of binding strongly to a protein antigen associated with human tumors, e.g. those of the colon and lung,-while binding to normal cells to a much lesser degree.

U.S. Pat. No. 5,484,596 provides a method of cancer therapy comprising surgically removing tumor tissue from a human cancer patient, treating the tumor tissue to obtain tumor cells, irradiating the tumor cells to be viable but non-tumorigenic, and using these cells to prepare a vaccine for the patient capable of inhibiting recurrence of the primary tumor while simultaneously inhibiting metastases. The patent teaches the development of monoclonal antibodies, which are reactive with surface antigens of tumor cells. As set forth at col. 4, lines 45 et seq., the patentees utilize autochthonous tumor cells in the development of monoclonal antibodies expressing active specific immunotherapy in human neoplasia.

U.S. Pat. No. 5,693,763 teaches a glycoprotein antigen characteristic of human carcinomas and not dependent upon the epithelial tissue of origin.

U.S. Pat. No. 5,783,186 is drawn to anti-Her2 antibodies, which induce apoptosis in Her2 expressing cells, hybridoma cell lines producing the antibodies, methods of treating cancer using the antibodies and pharmaceutical compositions including said antibodies.

U.S. Pat. No. 5,849,876 describes new hybridoma cell lines for the production of monoclonal antibodies to mucin antigens purified from tumor and non-tumor tissue sources.

U.S. Pat. No. 5,869,268 is drawn to a method for generating a human lymphocyte producing an antibody specific to a desired antigen, a method for producing a monoclonal antibody, as well as monoclonal antibodies produced by the method. The patent is particularly drawn to the production of an anti-HD human monoclonal antibody useful for the diagnosis and treatment of cancers.

U.S. Pat. No. 5,869,045 relates to antibodies, antibody fragments, antibody conjugates and single chain immunotoxins reactive with human carcinoma cells. The mechanism by which these antibodies function is 2-fold, in that the molecules are reactive with cell membrane antigens present on the surface of human carcinomas, and further in that the antibodies have the ability to internalize within the carcinoma cells, subsequent to binding, making them especially useful for forming antibody-drug and antibody-toxin conjugates. In their unmodified form the antibodies also manifest cytotoxic properties at specific concentrations.

U.S. Pat. No. 5,780,033 discloses the use of autoantibodies for tumor therapy and prophylaxis. However, this antibody is an anti-nuclear autoantibody from an aged mammal. In this case, the autoantibody is said to be one type of natural antibody found in the immune system. Because the autoantibody comes from "an aged mammal", there is no requirement that the autoantibody actually comes from the patient being treated. In addition the patent discloses natural and monoclonal antinuclear autoantibody from an aged mammal, and a hybridoma cell line producing a monoclonal antinuclear autoantibody.

U.S. Pat. No. 5,916,561 discloses a specific antibody, VFF-18, and its variants directed against the variant exon v6 of the CD44 gene. This antibody is an improvement over the comparator antibody in that it recognizes a human CD44 v6 variant rather than a rat CD44 v6 variant. In addition this antibody discloses diagnostic assays for CD44 v6 expression. There was no in vitro or in vivo function disclosed for this antibody.

U.S. Pat. No. 5,616,468 discloses a monoclonal antibody, Var3.1, raised against a synthetic peptide containing a sequence encoded by the human exon 6A of the CD44 gene.

Specifically this antibody does not bind to the 90 kD form of human CD44 and is distinguished from the Hermes-3 antibody. A method for detection of the v6 variant of CD44 is provided, as well as a method for screening and assaying for malignant transformation based on this antigen. A method for screening for inflammatory disease based on detecting the antigen in serum is also provided.

U.S. Pat. No. 5,879,898 discloses a specific antibody that binds to a 129 bp exon of a human CD44 variant 6 that produces a 43 amino acid peptide. The monoclonal antibody is produced by a number of hybridoma cell lines: MAK<CD44>M-1.1.12, MAK<CD44>M-2.42.3, MAK<CD44>M-4.3.16. The antibody is generated from a fusion protein that contains at least a hexapeptide of the novel CD44 v6 amino acid sequence. Further, there is a disclosure of an immunoassay for the detection of exon 6 variant that can be used as a cancer diagnostic. Significantly, there is no in vitro or in vivo function of this antibody disclosed.

U.S. Pat. No. 5,942,417 discloses a polynucleotide that encodes a CD44 like polypeptide, and the method of making a recombinant protein using the polynucleotide and its variants. Antibodies are claimed to these polypeptides however there are no specific examples and there are no deposited clones secreting such antibodies. Northern blots demonstrate the appearance of the polynucleotide in several types of tissues, but there is no accompanying evidence that there is translation and expression of this polynucleotide. Therefore, there is no evidence that there were antibodies to be made to the gene product of this polynucleotide, that these antibodies would have either in vitro or in vivo function, and whether they would be relevant to human cancerous disease.

U.S. Pat. No. 5,885,575 discloses an antibody that reacts with a variant epitope of CD44 and methods of identifying the variant through the use of the antibody. The isolated polynucleotide encoding this variant was isolated from rat cells, and the antibody, mAb1.1ASML, directed against this variant recognizes proteins of molecular weight 120 kD, 150 kD, 180 kD, and 200 kD. The administration of monoclonal antibody 1.1ASML delayed the growth and metastases of rat BSp73ASML in isogenic rats. Significantly 1.1ASML does not recognize human tumors as demonstrated by its lack of reactivity to LCLC97 human large-cell lung carcinoma. A human homolog was isolated from LCLC97 but no equivalent antibody recognizing this homolog was produced. Thus, although an antibody specific to a variant of rat CD44 was produced and shown to affect the growth and metastasis of rat tumors there is no evidence for the effect the this antibody against human tumors. More specifically the inventors point out that this antibody does not recognize human cancers.

SUMMARY OF THE INVENTION

The instant inventors have previously been awarded U.S. Pat. No. 6,180,357, entitled "Individualized Patient Specific Anti-Cancer Antibodies" directed to a process for selecting individually customized anti-cancer antibodies which are useful in treating a cancerous disease. It is well recognized in the art that some amino acid sequence can be varied in a polypeptide without significant effect on the structure or function of the protein. In the molecular rearrangement of antibodies, modifications in the nucleic or amino acid sequence of the backbone region can generally be tolerated. These include, but are not limited to, substitutions (preferred are conservative substitutions), deletions or additions. Furthermore, it is within the purview of this invention to conjugate standard chemotherapeutic modalities, e.g. radionuclides, with the CDMAB of the instant invention, thereby focusing the use of said chemotherapeutics. The CDMAB can also be conjugated to toxins, cytotoxic moieties, enzymes e.g. biotin conjugated enzymes, or hematogenous cells, thereby forming an antibody conjugate.

This application utilizes the method for producing patient specific anti-cancer antibodies as taught in the '357 patent for isolating hybridoma cell lines which encode for cancerous disease modifying monoclonal antibodies. These antibodies can be made specifically for one tumor and thus make possible the customization of cancer therapy. Within the context of this application, anti-cancer antibodies having either cell-killing (cytotoxic) or cell-growth inhibiting (cytostatic) properties will hereafter be referred to as cytotoxic. These antibodies can be used in aid of staging and diagnosis of a cancer, and can be used to treat tumor metastases. These antibodies can also be used for the prevention of cancer by way of prophylactic treatment. Unlike antibodies generated according to traditional drug discovery paradigms, antibodies generated in this way may target molecules and pathways not previously shown to be integral to the growth and/or survival of malignant tissue. Furthermore, the binding affinity of these antibodies are suited to requirements for initiation of the cytotoxic events that may not be amenable to stronger affinity interactions.

The prospect of individualized anti-cancer treatment will bring about a change in the way a patient is managed. A likely clinical scenario is that a tumor sample is obtained at the time of presentation, and banked. From this sample, the tumor can be typed from a panel of pre-existing cancerous disease modifying antibodies. The patient will be conventionally staged but the available antibodies can be of use in further staging the patient. The patient can be treated immediately with the existing antibodies, and a panel of antibodies specific to the tumor can be produced either using the methods disclosed herein or through the use of phage display libraries in conjunction with the screening methods herein disclosed. All the antibodies generated will be added to the library of anti-cancer antibodies since there is a possibility that other tumors can bear some of the same epitopes as the one that is being treated. The antibodies produced according to this method may be useful to treat cancerous disease in any number of patients who have cancers that bind to these antibodies.

In addition to anti-cancer antibodies, the patient can elect to receive the currently recommended therapies as part of a multi-modal regimen of treatment. The fact that the antibodies isolated via the present methodology are relatively non-toxic to non-cancerous cells allows for combinations of antibodies at high doses to be used, either alone, or in conjunction with conventional therapy. The high therapeutic index will also permit re-treatment on a short time scale that should decrease the likelihood of emergence of treatment resistant cells.

If the patient is refractory to the initial course of therapy or metastases develop, the process of generating specific antibodies to the tumor can be repeated for re-treatment. Furthermore, the anti-cancer antibodies can be conjugated to red blood cells obtained from that patient and re-infused for treatment of metastases. There have been few effective treatments for metastatic cancer and metastases usually portend a poor outcome resulting in death. However, metastatic cancers are usually well vascularized and the delivery of anti-cancer antibodies by red blood cells can have the effect of concentrating the antibodies at the site of the tumor. Even prior to metastases, most cancer cells are dependent on the host's blood supply for their survival and an anti-cancer antibody conjugated to red blood cells can be effective against in situ tumors as well. Alternatively, the antibodies may be conjugated to other hematogenous cells, e.g. lymphocytes, macrophages, monocytes, natural killer cells, etc.

There are five classes of antibodies and each is associated with a function that is conferred by its heavy chain. It is generally thought that cancer cell killing by naked antibodies are mediated either through antibody dependent cellular cytotoxicity or complement dependent cytotoxicity. For example murine IgM and IgG2a antibodies can activate human complement by binding the C1 component of the complement system thereby activating the classical pathway of complement activation which can lead to tumor lysis. For human antibodies the most effective complement activating antibodies are generally IgM and IgG1. Murine antibodies of the IgG2a and IgG3 isotype are effective at recruiting cytotoxic cells that have Fc receptors which will lead to cell killing by monocytes, macrophages, granulocytes and certain lymphocytes. Human antibodies of both the IgG1 and IgG3 isotype mediate ADCC.

Another possible mechanism of antibody mediated cancer killing may be through the use of antibodies that function to catalyze the hydrolysis of various chemical bonds in the cell membrane and its associated glycoproteins or glycolipids, so-called catalytic antibodies.

There are three additional mechanisms of antibody-mediated cancer cell killing. The first is the use of antibodies as a vaccine to induce the body to produce an immune response against the putative antigen that resides on the cancer cell. The second is the use of antibodies to target growth receptors and interfere with their function or to down regulate that receptor so that its function is effectively lost. The third is the effect of such antibodies on direct ligation of cell surface moieties that may lead to direct cell death, such as ligation of death receptors such as TRAIL R1 or TRAIL R2, or integrin molecules such as alpha V beta 3 and the like.

The clinical utility of a cancer drug is based on the benefit of the drug under an acceptable risk profile to the patient. In cancer therapy survival has generally been the most sought after benefit, however there are a number of other-well-recognized benefits in addition to prolonging life. These other benefits, where treatment does not adversely affect survival, include symptom palliation, protection against adverse events, prolongation in time to recurrence or disease-free survival, and prolongation in time to progression. These criteria are generally accepted and regulatory bodies such as the U.S. Food and Drug Administration (F.D.A.) approve drugs that produce these benefits (Hirschfeld et al. Critical Reviews in Oncology/Hematolgy 42:137-143 2002). In addition to these criteria it is well recognized that there are other endpoints that may presage these types of benefits. In part, the accelerated approval process granted by the U.S. F.D.A. acknowledges that there are surrogates that will likely predict patient benefit. As of year-end (2003), there have been sixteen drugs approved under this process, and of these, four have gone on to full approval, i.e., follow-up studies have demonstrated direct patient benefit as predicted by surrogate endpoints. One important endpoint for determining drug effects in solid tumors is the assessment of tumor burden by measuring response to treatment (Therasse et al. Journal of the National Cancer Institute 92(3):205-216 2000). The clinical criteria (RECIST criteria) for such evaluation have been promulgated by Response Evaluation Criteria in Solid Tumors Working Group, a group of international experts in cancer. Drugs with a demonstrated effect on tumor burden, as shown by objective responses according to RECIST criteria, in comparison to the appropriate control group tend to, ultimately, produce direct patient benefit. In the pre-clinical setting tumor burden is generally more straightforward to assess and document. In that pre-clinical studies can be translated to the clinical setting, drugs that produce prolonged survival in pre-clinical models have the greatest anticipated clinical utility. Analogous to producing positive responses to clinical treatment, drugs that reduce tumor burden in the pre-clinical setting may also have significant direct impact on the disease. Although prolongation of survival is the most sought after clinical outcome from cancer drug treatment, there are other benefits that have clinical utility and it is clear that tumor burden reduction, which may correlate to a delay in disease progression, extended survival or both, can also lead to direct benefits and have clinical impact (Eckhardt et al. Developmental Therapeutics: Successes and Failures of Clinical Trial Designs of Targeted Compounds; ASCO Educational Book, $39^{th}$ Annual Meeting, 2003, pages 209-219).

Using substantially the process of U.S. Pat. No. 6,180,357, the mouse monoclonal antibody H460-16-2 was obtained following immunization of mice with cells from a patient's lung tumor biopsy. The H460-16-2 antigen was expressed on the cell surface of a broad range of human cell lines from different tissue origins. The breast cancer cell line MDA-MB-231 (MB-231) and skin cancer cell line A2058 were susceptible to the cytotoxic effects of H460-16-2 in vitro.

The result of H460-16-2 cytotoxicity against MB-231 cells in culture was further extended by its anti-tumor activity towards these cancer cells when transplanted into mice (as disclosed in Ser. No. 10/603,000). Pre-clinical xenograft tumor models are considered valid predictors of therapeutic efficacy.

In the preventative in vivo model of human breast cancer, H460-16-2 treatment was significantly ($p<0.0001$) more effective in suppressing tumor growth during the treatment period than an isotype control antibody. At the end of the treatment phase, mice given H460-16-2 had tumors that grew to only 1.3 percent of the control group. During the post treatment follow-up period, the treatment effects of H460-16-2 were sustained and the mean tumor volume in the treated groups continued to be significantly smaller than controls until the end of the measurement phase. Using survival as a measure of antibody efficacy, it was estimated that the risk of dying in the H460-16-2 treatment group was about 71 percent of the antibody buffer control group ($p=0.028$) at 70 days post-treatment. These data demonstrated that H40-16-2 treatment conferred a survival benefit compared to the control-treated groups. H460-16-2 treatment appeared safe, as it did not induce any signs of toxicity, including reduced body weight and clinical distress. Thus, H460-16-2 treatment was efficacious as it both delayed tumor growth and enhanced survival compared to the control-treated groups in a well-established model of human breast cancer.

In addition, H460-16-2 demonstrated anti-tumor activity against MB-231 cells in an established in vivo tumor model (as disclosed in Ser. No. 10/603,000). Treatment with H460-16-2 was compared to the standard chemotherapeutic drug, Cisplatin, and it was shown that the Cisplatin and H460-16-2 treatment groups had significantly ($p<0.001$) smaller mean tumor volumes compared with groups treated with either antibody dilution buffer or the isotype control antibody. H460-16-2 treatment mediated tumor suppression that was approximately two-thirds that of Cisplatin chemotherapy but without the significant (19.2 percent) weight loss ($p<0.003$) and clinical distress, including 2 treatment-associated deaths, observed with Cisplatin treatment. The anti-tumor activity of H460-16-2 and its minimal toxicity make it an attractive anti-cancer therapeutic agent.

In the post-treatment period, H460-16-2 showed a significant survival benefit ($p<0.02$) as the risk of dying in the H460-16-2 group was about half of that in the isotype control antibody group at >70 days after treatment. The observed survival benefit continued past 120 days post-treatment where 100 percent of the isotype control and Cisplatin treated mice had died compared to 67 percent of the H460-16-2 treatment group. H460-16-2 maintained tumor suppression by delaying tumor growth by 26 percent compared to the isotype control antibody group. At 31 days post treatment, H460-16-2 limited tumor size by reducing tumor growth by 48 percent compared to the isotype control group, which is comparable to the 49 percent reduction observed at the end of the treatment. In the established tumor model of breast cancer, these results indicated the potential of H460-16-2 to maintain tumor suppression beyond the treatment phase and demonstrated the ability of the antibody to reduce the tumor burden and enhance survival in a mammal.

In addition to the beneficial effects in the established in vivo tumor model of breast cancer, H460-16-2 treatment in combination with a chemotherapeutic drug (Cisplatin) had anti-tumor activity against PC-3 cells in an established in vivo prostate cancer model (as disclosed in Ser. No. 10/810,165). Using a paired t-test, H460-16-2 plus Cisplatin treatment was significantly more effective in suppressing tumor growth shortly after the treatment period than buffer control ($p<0.0001$), Cisplatin treatment alone ($p=0.004$) or H460-16-2 treatment alone ($p<0.0001$). At the end of the treatment phase, mice given H460-16-2 plus Cisplatin had tumors that grew to only 28.5 percent of the buffer control group. For PC-3 SCID xenograft models, body weight can be used as a surrogate indicator of disease progression. Mice in all the groups experienced severe weight loss. In this study, mice in all groups showed a weight loss of approximately 23 to 35 percent by the end of the treatment period. The group treated with H460-16-2 showed the smallest degree of weight loss (21.7 percent). After treatment, day 48, there was no significant increase in weight loss associated with the treatment of H460-16-2 and Cisplatin in comparison to buffer control ($p=0.5042$). Thus, H460-16-2 plus Cisplatin treatment was efficacious as it delayed tumor growth compared to the isotype control treated group in a well-established model of human prostate cancer.

In order to validate the H460-16-2 epitope as a drug target, the expression of H460-16-2 antigen in normal human tissues was previously determined (Ser. No. 10/603,000). This work was extended by comparison with the anti-CD44 antibodies; clone L178 (disclosed in Ser. No. 10/647,818) and clone BU75 (disclosed in Ser. No. 10/810,165). By IHC staining with H460-16-2, the majority of the tissues failed to express the H460-16-2 antigen, including the cells of the vital organs, such as the liver, kidney (except for marginal staining of tubular epithelial cells), heart, and lung. Results from tissue staining indicated that H460-16-2 showed restricted binding to various cell types but had binding to infiltrating macrophages, lymphocytes, and fibroblasts. The BU75 antibody showed a similar staining pattern. However, there was at least one difference of note; staining of lymphocytes was more intense with BU75 in comparison to H460-16-2.

Localization of the H460-16-2 antigen and determining its prevalence within the population, such as among breast cancer patients, is important in assessing the therapeutic use of H460-16-2 and designing effective clinical trials. To address H460-16-2 antigen expression in breast tumors from cancer patients, tumor tissue samples from 50 individual breast cancer patients were previously screened for expression of the H460-16-2 antigen (Ser. No. 10/603,000) and was compared to L178 (Ser. No. 10/647,818), BU75 (Ser. No. 10/810,165) and the anti-Her2 antibody c-erbB-2 (Ser. No. 10/810,165).

The results of these studies were similar and showed that 62 percent of tissue samples stained positive for the H460-16-2 antigen while 73 percent of breast tumor tissues were positive for the BU75 epitope. Expression of H460-16-2 within patient samples appeared specific for cancer cells as staining was restricted to malignant cells. H460-16-2 stained 4 of 10 samples of normal tissue from breast cancer patients while BU75 stained 8. Breast tumor expression of both the H460-16-2 and BU75 antigen appeared to be mainly localized to the cell membrane of malignant cells, making CD44 an attractive target for therapy. H460-16-2 expression was further evaluated based on breast tumor expression of the receptors for the hormones estrogen and progesterone, which play an important role in the development, treatment, and prognosis of breast tumors. No correlation was apparent between expression of the H460-16-2 antigen and expression of the receptors for either estrogen or progesterone. When tumors were analyzed based on their stage, or degree to which the cancer advanced, again there was no clear correlation between H460-16-2 antigen expression and tumor stage. Similar results were obtained with BU75. In comparison to c-erbB-2, H460-16-2 showed a completely different staining profile where 52 percent of the breast tumor tissue samples that were positive for the H460-16-2 antigen were negative for Her2 expression indicating a yet unmet targeted therapeutic need for breast cancer patients. There were also differences in the intensity of staining between the breast tumor tissue sections that were positive for both H460-16-2 and Her2. The c-erbB-2 antibody also positively stained one of the normal breast tissue sections.

To further extend the potential therapeutic benefit of H460-16-2, the frequency and localization of the antigen within various human cancer tissues was also previously determined (Ser. No. 10/603,000) and was compared to clone L178 (Ser. No. 10/647,818). The majority of these tumor types were also positive for the L178 antigen. As with human breast tumor tissue, H460-16-2 and L178 localization occurred on the membrane of tumor cells. However, there was substantially more membrane localization with the L178 compared to the H460-16-2 antibody. Also, of the tumor types that were stained by both H460-16-2 and L178, 43 percent of the tissues showed higher intensity staining with the L178 antibody.

There appears to be no form of CD44 that exactly matches the IHC data presented herein based on comparisons with the IHC data from the literature. The standard form of CD44 is normally expressed in the human brain; the H460-16-2 antigen is not. Antibodies directed against pan-CD44 isoforms do not stain the liver (including Kuppfer cells) and positively stain the endometrial glands in all phases of the reproductive cycle. The H460-16-2 antigen is clearly present on Kuppfer cells and is only present on the secretory endometrial glands of the reproductive cycle. H460-16-2 antigen is clearly present on tissue macrophages and only the variant forms V4/5 and V8/9 show occasional macrophage staining. The similar yet distinct binding pattern seen with H460-16-2 in comparison to anti-CD44 L178 and now BU75 indicates that the H460-16-2 antigen is an unique epitope of CD44.

As disclosed previously (Ser. No. 10/647,818), additional biochemical data also indicated that the antigen recognized by H460-16-2 is one of the forms of CD44. This was supported by studies that showed a monoclonal antibody (L178) reactive against CD44 identifies proteins that were bound to H460-16-2 by immunoprecipitation. Western blotting studies also suggested that the epitope of CD44 recognized by H460-16-2 was not present on v6 or v10. The H460-16-2 epitope was also distinguished by being carbohydrate and conformation dependent, whereas many anti-CD44 antibodies are directed against peptide portions of CD44. These IHC and biochemical results demonstrated that H460-16-2 binds to a variant of the CD44 antigen. Thus, the preponderance of evidence showed that H460-16-2 mediates anti-cancer effects through ligation of an unique carbohydrate dependent conformational epitope present on a variant of CD44. For the purpose of this invention, said epitope is defined as a "CD44 antigenic moiety" characterized by its ability to bind with a monoclonal antibody encoded by the hybridoma cell line H460-16-2, antigenic binding fragments thereof or antibody conjugates thereof.

In order to further elucidate the mechanism behind H460-16-2's anti-cancer effects, hyaluronic acid (HA) binding assays were performed (as disclosed in Ser. No. 10/810,165). It was determined that an average concentration of 1.87 ($\pm$1.01) micrograms/mL of H460-16-2 was required to inhibit adhesion of MDA-MB-231 cells to HA by 50 percent. These results indicated that H460-16-2 interacts with, at least in part, the region(s) on CD44 that are responsible for binding to HA and consequently could be mediating its anti-cancer effects through down regulation of angiogenesis or tumor invasiveness through the ECM.

In addition to the HA binding assays, a cell cycling experiment was performed in order to determine if the H460-16-2 in vitro and in vivo anti-cancer effects were due to regulation of the cell cycle (as disclosed in Ser. No. 10/810,165). After 24 hours and with 20 $\mu$g/mL of H460-16-2, there was an increase in the number of MDA-MB-231 apoptotic cells in comparison to the isotype control. This effect also appeared to be dose dependent. Therefore, the efficacy of H460-16-2 might be also due, in whole or in part, to its apoptotic inducing capabilities.

In toto, this data demonstrates that the H460-16-2 antigen is a cancer associated antigen and is expressed in humans, and is a pathologically relevant cancer target. Further, this data also demonstrates the binding of the H460-16-2 antibody to human cancer tissues, and can be used appropriately for assays that can be diagnostic, predictive of therapy, or prognostic. In addition, the cell membrane localization of this antigen is indicative of the cancer status of the cell due to the lack of expression of the antigen in most non-malignant cells, and this observation permits the use of this antigen, its gene or derivatives, its protein or its variants to be used for assays that can be diagnostic, predictive of therapy, or prognostic.

Other studies, involving the use of anti-CD44 antibodies, have limitations of therapeutic potential that are not exhibited by H460-16-2. H460-16-2 demonstrates both in vitro and in vivo anti-tumor activity. Previously described antibodies such as MAK<CD44>M-1.1.12, MAK<CD44>M-2.42.3 and MAK<CD44>M-4.3.16 have no in vitro or in vivo cytotoxicity ascribed to them and VFF-18 and Mab U36 show no intrinsic tumor cytotoxicity. In addition other anti-CD44 antibodies that have shown in vivo tumor effects also have certain limitations that are not evident with H460-16-2. For example, ASML1.1, K926, anti-CD44s and IM-78.1 show in vivo anti-tumor activity against rat, murine, rat and murine tumors grown in xenograft models respectively. H460-16-2 demonstrates anti-tumor activity in a model of human cancer. H460-16-2 is also directed against human CD44 while antibodies such as ASML1.1 recognize only rat CD44. The clone 515 anti-CD44 antibody does inhibit peritoneal tumor implantation of a human ovarian cell line but does not prevent or inhibit tumor growth. H460-16-2 is capable of inhibiting human breast tumor growth in a SCID mouse xenograft model. GKW.A3 is an anti-human CD44 monoclonal antibody capable of inhibiting tumor growth of a human metastasizing melanoma grown in mice in a preventative but not an established model. H460-16-2 has demonstrated significant anti-tumor activity in both preventative and established murine xenograft models of human breast cancer. Consequently, it is quite apparent that H460-16-2 has superior anti-tumor properties in comparison to previously described anti-CD44 antibodies. It has demonstrated both in vitro and in vivo anti-tumor activity on a human breast tumor in SCID mice and is directed against human CD44. It also exhibits activity in a preventative and established (more clinically relevant) model of human breast cancer and it exhibits activity with Cisplatin in an established model of human prostate cancer.

In all, this invention teaches the use of the H460-16-2 antigen as a target for a therapeutic agent, that when administered can reduce the tumor burden of a cancer expressing the antigen in a mammal (thus delaying disease progression), and can also lead to a prolonged survival of the treated mammal. This invention also teaches the use of a CDMAB (H460-16-2), and its derivatives, to target its antigen to reduce the tumor burden of a cancer expressing the antigen in a mammal, and to prolong the survival of a mammal bearing tumors that express this antigen. In addition, this invention teaches that after binding to its antigen, H460-16-2 can interfere with a cancer cell's ability to interact with hyaluronic acid and can also cause a cancer cell to undergo apoptosis. Furthermore, this invention also teaches the use of detecting the H460-16-2 antigen in cancerous cells that can be useful for the diagnosis, prediction of therapy, and prognosis of mammals bearing tumors that express this antigen.

The present invention describes the development and use of H460-16-2 developed by the process described in patent U.S. Pat. No. 6,180,357 and identified by its effect in a cytotoxic assay, in non-established and established tumor growth in animal models and in prolonging survival time in those suffering from cancerous disease. The present invention also describes the development and use of AR37A335.8 developed by the process described in patent U.S. Pat. No. 6,180,357 and identified by its effect in a cytotoxic assay and in prophylactic prevention of tumor growth in animal models. This invention represents an advance in the field of cancer treatment in that it describes, for the first time, naked antibodies that bind specifically to an epitope or epitopes present on the target molecule, CD44, and that also have in vitro cytotoxic properties against malignant tumor cells but not normal cells, and which also directly mediate inhibition of tumor growth and extension of survival in in vivo models of human cancer. This is an advance in relation to any other previously described anti-CD44 antibody, since none have been shown to have similar properties. It also provides an advance in the field since it clearly demonstrates, and for the first time, the direct involvement of CD44 in events associated with growth and development of certain types of tumors. It also represents an advance in cancer therapy since it has the potential to display similar anti-cancer properties in human patients. A further advance is that inclusion of these antibodies in a library of anti-cancer antibodies will enhance the possibility of targeting tumors expressing different antigen markers by determination of the appropriate combination of different anti-cancer antibodies, to find the most effective in targeting and inhibiting growth and development of the tumors.

In all, this invention teaches the use of the H460-16-2 antigen as a target for a therapeutic agent, that when administered can reduce the tumor burden of a cancer expressing the antigen in a mammal, and can also lead to a prolonged survival of the treated mammal. This invention also teaches the use of CDMAB (H460-16-2 and AR37A335.8), and their derivatives, ligands and antigen binding fragments thereof, to target their antigen to reduce the tumor burden of a cancer expressing the antigen in a mammal, and to prolong the survival of a mammal bearing tumors that express this antigen. Furthermore, this invention also teaches the use of detecting the H460-16-2 and AR37A335.8 antigen in cancerous cells that can be useful for the diagnosis, prediction of therapy, and prognosis of mammals bearing tumors that express this antigen.

Accordingly, it is an objective of the invention to utilize a method for producing cancerous disease modifying antibodies (CDMAB) raised against cancerous cells derived from a particular individual, or one or more particular cancer cell lines, which CDMAB are cytotoxic with respect to cancer cells while simultaneously being relatively non-toxic to non-cancerous cells, in order to isolate hybridoma cell lines and the corresponding isolated monoclonal antibodies and antigen binding fragments thereof for which said hybridoma cell lines are encoded.

It is an additional objective of the invention to teach cancerous disease modifying antibodies, ligands and antigen binding fragments thereof.

It is a further objective of the instant invention to produce cancerous disease modifying antibodies and ligands whose cytotoxicity is mediated through antibody dependent cellular toxicity.

It is yet an additional objective of the instant invention to produce cancerous disease modifying antibodies and ligands whose cytotoxicity is mediated through complement dependent cellular toxicity.

It is still a further objective of the instant invention to produce cancerous disease modifying antibodies and ligands whose cytotoxicity is a function of their ability to catalyze hydrolysis of cellular chemical bonds.

A still further objective of the instant invention is to produce cancerous disease modifying antibodies or ligands which are useful in a binding assay for diagnosis, prognosis, and monitoring of cancer.

Other objects and advantages of this invention will become apparent from the following description wherein are set forth, by way of illustration and example, certain embodiments of this invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1 compares the percentage cytotoxicity and binding levels of the AR37A335.8 hybridoma supernatants against cell lines PC-3, LnCap and CCD-27sk.

FIG. 2 is a comparison of AR37A335.8 versus positive and negative controls in a cytotoxicity assay.

FIG. 3 represents binding of AR37A335.8 and the anti-EGFR control to cancer and normal cell lines. The data is tabulated to present the mean fluorescence intensity as a fold increase above isotype control.

FIG. 11 is a summary of H460-16-2 binding on a human prostate tumor and normal tissue microarray.

FIG. 12. Representative micrographs showing the binding pattern on prostate tumor tissue obtained with H460-16-2 (A) or the isotype control antibody (B) and on normal prostate tissue obtained with H460-16-2 (C) or the isotype control antibody (D) from a human tissue microarray. H460-16-2 displayed strong positive staining for the tumor cells and weak staining for stromal fibroblasts on the normal tissue. Magnification is 200×.

FIG. 13 is a summary of H460-16-2 binding on a human liver tumor and normal tissue microarray.

FIG. 15 is a summary of the number of apoptotic cells in MDA-MB-231 tumor xenografts after H460-16-2 or buffer treatment as determined by a TUNEL assay or H & E staining.

FIG. 19. Raw sequence data for pCR2.1(H460-16-2 Vh) clones (SEQ ID NOS: 1-8 and 36).

FIG. 21. Raw sequence data for pCR2.1(H460-16-2 Vk) and pCR2.1(H460-16-2 Vh) clones (SEQ ID NOS:9-11).

FIG. 23. Primer Sequences (SEQ ID NOS:12-19).

FIG. 36. Raw sequence data for pNEF38(H460-16-2 Vk) and pDEF38(H460-16-2 Vh) clones (SEQ ID NOS:20-25).

FIG. 39. Map of pkCR5B43G3.

FIG. 43. List of primers used to construct the chimeric IgG2 isotype of H460-16-2 (SEQ ID NOS:26-35).

FIG. 48. Analysis of the antibody concentration, by SDS-PAGE followed by staining with Coomassie Fluo-Orange staining, of the antibody produced by the CHOcTA clone 6'.

FIG. 52 represents the total apoptotic effects of the murine and chimeric H460-16-2 antibodies obtained in two (2) separate Annexin-V staining experiments.

DETAILED DESCRIPTION OF THE INVENTION

Figure 4:
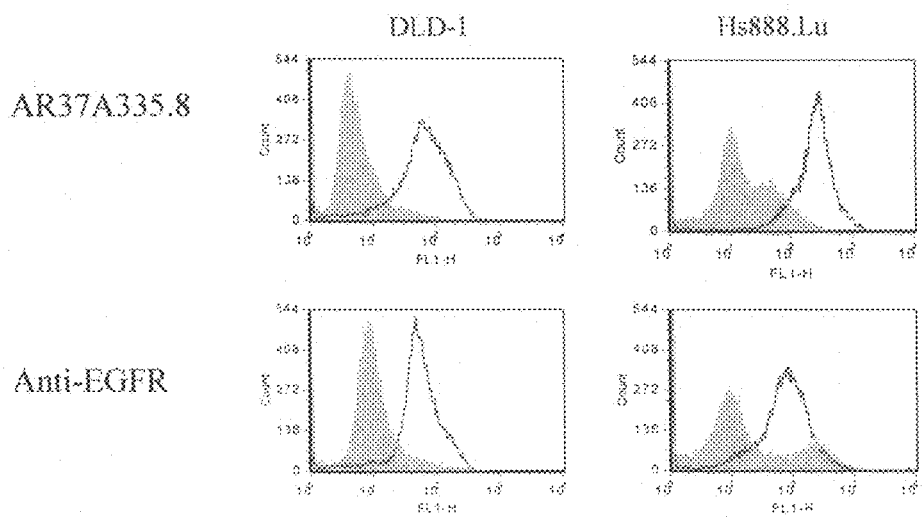
FIG. 4 includes representative FACS histograms of AR37A335.8 and anti-EGFR antibodies directed against a cancer and non-cancer cell line.

In general, the following words or phrases have the indicated definition when used in the summary, description, examples, and claims.

The term "antibody" is used in the broadest sense and specifically covers, for example, single monoclonal antibodies (including agonist, antagonist, and neutralizing antibodies, de-immunized, murine, chimerized or humanized antibodies), antibody compositions with polyepitopic specificity, single chain antibodies, immunoconjugates and fragments of antibodies (see below).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma (murine or human) method first described by Kohler et al., Nature, 256:495 (1975), or may be made by recombinant DNA methods (see, e.g., U.S. Pat. No. 4,816, 567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

"Antibody fragments" comprise a portion of an intact antibody, preferably comprising the antigen-binding or variable region thereof. Examples of antibody fragments include less than full length antibodies, Fab, Fab', F(ab')$_2$, and Fv fragments; diabodies; linear antibodies; single-chain antibody molecules; single-chain antibodies, single domain antibody molecules, fusion proteins, recombinant proteins and multispecific antibodies formed from antibody fragment(s).

An "intact" antibody is one which comprises an antigen-binding variable region as well as a light chain constant domain (CL) and heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

Depending on the amino acid sequence of the constant domain of their heavy chains, intact antibodies can be assigned to different "classes". There are five-major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called a, d, e, ?, and μ, respectively. The subunit structures and three-dimensional configurations of different classes of immunoglobulins are well known.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express Fc?RIII only, whereas monocytes express Fc?RI, Fc?RII and Fc?RIII. FcR expression on hematopoietic cells in summarized is Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS* (USA) 95:652-656 (1998).

"Effector cells" are leukocytes which express one or more FcRs and perform effector functions. Preferably, the cells express at least Fc?RIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

The terms "Fc receptor" or "FcR" are used to describe a receptor that binds to the Fe region of an antibody. The preferred FcR is a native sequence human FcR. Moreover, a preferred FcR is one which binds an IgG antibody (a gamma receptor) and includes receptors of the Fc?RI, Fc?RII, and Fc? RIII subclasses, including allelic variants and alternatively spliced forms of these receptors. Fc?RII receptors include Fc?RIIA (an "activating receptor") and Fc?RIIB (an "inhibiting receptor"), which have similar amino acid sequences that differ primarily in the cytoplasmic domains thereof. Activating receptor Fc?RIIA contains an immunoreceptor tyrosine-based activation motif (ITAM) in its cytoplasmic domain. Inhibiting receptor Fc?RIIB contains an immunoreceptor tyrosine-based inhibition motif (ITIM) in its cytoplasmic domain. (see review M. in Daëron, *Annu. Rev. Immunol*. 15:203-234 (1997)). FcRs are reviewed in Ravetch and Kinet, Annu. Rev. Immunol 9:457-92 (1991); Capel et al., *Immunomethods* 4:25-34 (1994); and de Haas et al., *J. Lab. Clin. Med*. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol*. 117:587 (1976) and Kim et al., *Eur. J. Immunol*. 24:2429 (1994)).

"Complement dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the >sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 2632 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol*. 196:901-917 (1987)). "Framework Region" or "FR" residues are those variable domain residues other than the hypervariable region residues as herein defined. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site. The Fab fragment also contains the constant domain of the light chain and the first constant domain (CH I) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (?) and lambda (?), based on the amino acid sequences of their constant domains.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the scFv to form the desired structure for antigen binding. For a review of scFv see Plückthun in *The Pharmacology of Monoclonal Antibodies*, vol. 113, Rosenburg and Moore eds., Springer-Verlag, N.Y., pp. 269-315 (1994).

The term "diabodies" refers to small antibody fragments with two antigen-binding sites, which fragments comprise a variable heavy domain ($V_H$) connected to a variable light domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other protcinaceous or nonproteinaceous solutes. Isolated antibody includes the antibody in situ within recombinant cells since at least one component of the antibody's natural environment will not be present. Ordinarily, however, isolated antibody will be prepared by at least one purification step.

An antibody "which binds" an antigen of interest, e.g. CD44 antigenic moiety, is one capable of binding that antigenic moiety with sufficient affinity such that the antibody is useful as a therapeutic agent in targeting a cell expressing the antigen. Where the antibody is one which binds CD44 antigenic moiety, it will usually preferentially bind CD44 antigenic moiety as opposed to other receptors, and does not include incidental binding such as non-specific Fc contact, or binding to post-translational modifications common to other antigens and may be one which does not significantly cross-react with other proteins. Methods, for the detection of an antibody that binds an antigen of interest, are well known in the art and can include but are not limited to assays such as FACS, cell ELISA and Western blot.

As used herein, the expressions "cell", "cell line", and "cell culture" are used interchangeably, and all such designations include progeny. It is also understood that all progeny may not be precisely identical in DNA content, due to deliberate or inadvertent mutations. Mutant progeny that have the same function or biological activity as screened for in the originally transformed cell are included. It will be clear from the context where distinct designations are intended.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. Hence, the mammal to be treated herein may have been diagnosed as having the disorder or may be predisposed or susceptible to the disorder.

The terms "cancer" and "cancerous" refer to or describe the physiological condition in mammals that is typically characterized by unregulated cell growth or death. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carnomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2?-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol- Myers Squibb Oncology, Princeton, N.J.) and docetaxel (TAXOTERE®, Aventis, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

"Mammal" for purposes of treatment refers to any animal classified as a mammal, including humans, mice, SCID or nude mice or strains of mice, domestic and farm animals, and zoo, sports, or pet animals, such as sheep, dogs, horses, cats, cows, etc. Preferably, the mammal herein is human.

"Oligonucleotides" are short-length, single- or double-stranded polydeoxynucleotides that are chemically synthesized by known methods (such as phosphotriester, phosphite, or phosphoramidite chemistry, using solid phase techniques such as described in EP 266,032, published 4 May 1988, or via deoxynucleoside H-phosphonate intermediates as described by Froehler et al., *Nucl. Acids Res.*, 14:5399-5407, 1986. They are then purified on polyacrylamide gels.

Unless indicated otherwise, the term "CD44 antigenic moiety" when used herein refers to the single chain hyaluronic acid (HA) binding glycoprotein also referred to as hyaluronate receptor, H-CAM, gp85 and Hermes.

An antibody which induces "apoptosis" is one which induces programmed cell, death as determined by binding of annexin V, fragmentation of DNA, cell shrinkage, dilation of endoplasmic reticulum, cell fragmentation, and/or formation of membrane vesicles (called apoptotic bodies).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567 and Morrison et al, *Proc. Natl. Acad. Sci. USA*, 81:6851-6855 (1984)).

"Humanized" forms of non-human (e.g. murine) antibodies are specific chimeric immunoglobulins, immunoglobulin chains or fragments thereof (such as Fv, Fab, Fab', F(ab)$_2$ or other antigen-binding subsequences of antibodies) which contain minimal sequence derived from non-human immunoglobulin. For the most part, humanized antibodies are human immunoglobulins (recipient antibody) in which residues from the complementarity determining regions (CDRs) of the recipient antibody are replaced by residues from the CDRs of a non-human species (donor antibody) such as mouse, rat or rabbit having the desired specificity, affinity and capacity. In some instances, Fv framework region (FR) residues of the human immunoglobulin are replaced by corresponding non-human FR residues. Furthermore, the humanized antibody may comprise residues which are found neither in the recipient antibody nor in the imported CDR or FR sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR residues are those of a human immunoglobulin consensus sequence. The humanized antibody optimally also will comprise at least a portion of an immunoglobulin constant region (Fc), typically that of a human immunoglobulin.

"De-immunized" antibodies are immunoglobulins that are non-immunogenic, or less immunogenic, to a given species. De-immunization can be achieved through structural alterations to the antibody. Any de-immunization technique known to those skilled in the art can be employed. One suitable technique for de-immunizing antibodies is described, for example, in WO 00/34317 published Jun. 15, 2000.

"Homology" is defined as the percentage of residues in the amino acid sequence variant that are identical after aligning the sequences and introducing gaps, if necessary, to achieve the maximum percent homology. Methods and computer programs for the alignment are well known in the art.

Throughout the instant specification, hybridoma cell lines, as well as the isolated monoclonal antibodies which are produced therefrom, are alternatively referred to by their internal designation, H460-16-2 and AR37A335.8 or Depository Designation, ATCC Accession No. PTA-4621 or IDAC 280104-06 respectively.

As used herein "ligand" includes a moiety which exhibits binding specificity for a target antigen, and which may be an intact antibody molecule and any molecule having at least an antigen-binding region or portion thereof (i.e., the variable portion of an antibody molecule), e.g., an Fv molecule, Fab molecule, Fab' molecule, F(ab').sub.2 molecule, a bispecific antibody, a fusion protein, or any genetically engineered molecule which specifically recognizes and binds the antigen bound by the isolated monoclonal antibody produced by the hybridoma cell line designated as, ATCC Accession No. PTA-4621 or IDAC 280104-06 (the ATCC PTA-4621 or IDAC 280104-06 antigen).

As used herein "antigen-binding region" means a portion of the molecule which recognizes the target antigen.

As used herein "competitively inhibits" means being able to recognize and bind a determinant site to which the monoclonal antibody produced by the hybridoma cell line designated as PTA-4621 or IDAC 280104-06, (the PTA-4621 or IDAC 280104-06 antibody) is directed using conventional reciprocal antibody competition assays. (Belanger L., Sylvestre C. and Dufour D. (1973), Enzyme linked immunoassay for alpha fetoprotein by competitive and sandwich procedures. Clinica Chimica Acta 48, 15).

As used herein "target antigen" is the PTA-4621 or IDAC 280104-06 antigen or portions thereof.

As used herein, an "immunoconjugate" means any molecule or ligand such as an antibody chemically or biologically linked to a cytotoxin, a radioactive agent, enzyme, toxin, an anti-tumor drug or a therapeutic agent. The antibody may be linked to the cytotoxin, radioactive agent, anti-tumor drug or therapeutic agent at any location along the molecule so long as it is able to bind its target. Examples of immunoconjugates include antibody toxin chemical conjugates and antibody-toxin fusion proteins.

As used herein, a "fusion protein" means any chimeric protein wherein an antigen binding region is connected to a biologically active molecule, e.g., toxin, enzyme, or protein drug.

In order that the invention herein described may be more fully understood, the following description is set forth.

The present invention provides ligands (i.e., PTA-4621 or IDAC 280104-06 ligands) which specifically recognize and bind the PTA-4621 or IDAC 280104-06 antigen.

The ligand of the invention may be in any form as long as it has an antigen-binding region which competitively inhibits the immunospecific binding of the monoclonal antibody produced by hybridoma PTA-4621 or IDAC 280104-06 to its target antigen. Thus, any recombinant proteins (e.g., fusion proteins wherein the antibody is combined with a second protein such as a lymphokine or a tumor inhibitory growth factor) having the same binding specificity as the IDAC 280104-06 antibody fall within the scope of this invention.

In one embodiment of the invention, the ligand is the PTA-4621 or IDAC 280104-06 antibody.

In other embodiments, the ligand is an antigen binding fragment which may be a Fv molecule (such as a single chain Fv molecule), a Fab molecule, a Fab' molecule, a F(ab')2 molecule, a fusion protein, a bispecific antibody, a heteroantibody or any recombinant molecule having the antigen-binding region of the PTA-4621 or IDAC 280104-06 antibody. The ligand of the invention is directed to the epitope to which the PTA-4621 or IDAC 280104-06 monoclonal antibody is directed.

The ligand of the invention may be modified, i.e., by amino acid modifications within the molecule, so as to produce derivative molecules. Chemical modification may also be possible.

Derivative molecules would retain the functional property of the polypeptide, namely, the molecule having such substitutions will still permit the binding of the polypeptide to the PTA-4621 or IDAC 280104-06 antigen or portions thereof.

These amino acid substitutions include, but are not necessarily limited to, amino acid substitutions known in the art as "conservative".

For example, it is a well-established principle of protein chemistry that certain amino acid substitutions, entitled "conservative amino acid substitutions," can frequently be made in a protein without altering either the conformation or the function of the protein.

Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

Given an antibody, an individual ordinarily skilled in the art can generate a competitively inhibiting ligand, for example a competing antibody, which is one that recognizes the same epitope (Belanger et al., 1973). One method could entail immunizing with an immunogen that expresses the antigen recognized by the antibody. The sample may include but is not limited to tissue, isolated protein(s) or cell line(s). Resulting hybridomas could be screened using a competing assay, which is one that identifies antibodies that inhibit the binding of the test antibody, such as ELISA, FACS or immunoprecipiation. Another method could make use of phage display libraries and panning for antibodies that recognize said antigen (Rubinstein et al., 2003). In either case, hybridomas would be selected based on their ability to out-compete the binding of the original antibody to its target antigen. Such hybridomas would therefore possess the characteristic of recognizing the same antigen as the original antibody and more specifically would recognize the same epitope.

EXAMPLE 1

Hybridoma Production—Hybridoma Cell Line AR37A335.8

The hybridoma cell line AR37A335.8 was deposited, in accordance with the Budapest Treaty, with the International Depository Authority of Canada (IDAC), Bureau of Microbiology, Health Canada, 1015 Arlington Street, Winnipeg, Manitoba, Canada, R3E 3R2, on Jan. 28, 2004, under Accession Number 280104-06. In accordance with 37 CFR 1.808, the depositors assure that all restrictions imposed on the availability to the public of the deposited materials will be irrevocably removed upon the granting of a patent.

To produce the hybridoma that produces the anti-cancer antibody AR37A335.8, a fresh single cell suspension of the PC-3 prostate cancer cell line that had been grown as a solid tumor in SCID mice, was prepared in PBS. IMMUNEASY™ (Qiagen, Venlo, Netherlands) adjuvant was prepared for use by gentle mixing. Five to seven week old BALB/c mice were immunized by injecting subcutaneously, 2 million cells in 50 microliters of the antigen-adjuvant. Recently prepared antigen-adjuvant was used to boost the immunized mice intraperitoneally, 2 and 5 weeks after the initial immunization, with 2 million cells in 50 microliters. A spleen was used for fusion three days after the last immunization. The hybridomas were prepared by fusing the isolated splenocytes with NSO-1 myeloma partners. The supernatants from the fusions were tested for subcloning of the hybridomas.

To determine whether the antibodies secreted by the hybridoma cells are of the IgG or IgM isotype, an ELISA assay was employed. 100 microliters/well of goat anti-mouse IgG+IgM (H+L) at a concentration of 2.4 micrograms/mL in coating buffer (0.1M carbonate/bicarbonate buffer, pH 9.2-9.6) at 4° C. was added to the ELISA plates overnight. The plates were washed thrice in washing buffer (PBS+0.05% Tween). 100 microliters/well blocking buffer (5% milk in wash buffer) was added to the plate for 1 hour. at room temperature and then washed thrice in washing buffer. 100 microliters/well of hybridoma supernatant was added and the plate incubated for 1 hour. at room temperature. The plates were washed thrice with washing buffer and 1/100,000 dilution of either goat anti-mouse IgG or IgM horseradish peroxidase conjugate (diluted in PBS containing 5% milk), 100 microliters/well, was added. After incubating the plate for 1 hour. at room temperature the plate was washed thrice with washing buffer. 100 microliters/well of TMB solution was incubated for 1-3 minutes at room temperature. The color reaction was terminated by adding 100 microliters/well 2M $H_2SO_4$ and the plate was read at 450 nm with a Perkin-Elmer HTS7000 plate reader. As indicated in FIG. 1, the AR37A335.8 hybridoma secreted primarily antibodies of the IgG isotype.

To determine the subclass of antibody secreted by the hybridoma cells, an isotyping experiment was performed using a Mouse Monoclonal Antibody Isotyping Kit (GE Healthcare, Piscataway, N.J.). Antibody-containing hybridoma supernatant was added to a test tube (in a 1:10 dilution with TBS-T) with an isotyping strip carrying goat antibody specific for the different types of peptide chain. The tube was agitated for 15 minutes. The strip was then washed twice with TBS-T for 5 minutes with agitation. A peroxidase-labelled, species-specific anti-mouse antibody was added (in a 1:500 dilution with TBS-T) to the test tube for 15 minutes, to detect the monoclonal antibody bound to the goat antibody on the stick. The strip was again washed twice with TBS-T for 5 minutes with agitation. The peroxidase-labelled antibody bound to the strip was then detected using a peroxidase substrate system. One 30 mg tablet of 4-chloro-1-napthol was dissolved in 10 mL cold ethanol, and one drop of hydrogen peroxide solution (30% v/v) was diluted in 50 mL TBS. The two solutions were combined immediately before use, and 3 mL was added to the isotyping strip for 15 minutes with agitation. The substrate solution was then discarded and the strip was washed three times with 5 mL distilled water with agitation. The typing stick was then removed from the test tube and analysed for results. The anti-cancer antibody AR37A335.8 is of the IgG2b, lambda isotype.

After one round of limiting dilution hybridoma supernatants were tested for antibodies that bound to target cells in a cell ELISA assay. Two human prostate cancer cell lines and 1 human normal skin cell line were tested: PC-3, LnCap and CCD-27sk respectively. The plated cells were fixed prior to use. The plates were washed thrice with PBS containing $MgCl_2$ and $CaCl_2$ at room temperature. 100 microliters of 2% paraformaldehyde diluted in PBS was added to each well for 10 minutes at room temperature and then discarded. The plates were again washed with PBS containing $MgCl_2$ and $CaCl_2$ three times at room temperature. Blocking was done with 100 microliters/well of 5% milk in wash buffer (PBS+ 0.05% Tween) for 1 hour at room temperature. The plates were washed thrice with wash buffer and the hybridoma supernatant was added at 100 microliters/well for 1 hour at room temperature. The plates were washed 3 times with wash buffer and 100 microliters/well of 1/25,000 dilution of goat anti-mouse IgG antibody conjugated to horseradish peroxidase (diluted in PBS containing 5% milk) was added. After 1 hour incubation at room temperature the plates were washed 3 times with wash buffer and 100 microliter/well of TMB substrate was incubated for 1-3 minutes at room temperature. The reaction was terminated with 100 microliters/well 2M $H_2SO_4$ and the plate read at 450 nm with a Perkin-Elmer HTS7000 plate reader. The results as tabulated in FIG. 1 were expressed as the number of folds above background compared to an in-house IgG isotype control that has previously been shown not to bind to the cell lines tested. The antibodies from the hybridoma AR37A335.8 showed substantial binding to the prostate cancer cell line PC-3 and to the skin cell line CCD-27sk. AR37A335.8 did not show any detectable binding to another prostate cancer cell line LnCap.

In conjunction with testing for antibody binding the cytotoxic effect of the hybridoma supernatants were tested in the same cell lines: PC-3, LnCap and CCD-27sk. Calcein AM was obtained from Molecular Probes (Eugene, Oreg.). The assays were performed according to the manufacturer's instructions with the changes outlined below. Cells were plated before the assay at the predetermined appropriate density. After 2 days, 100 µl of supernatant from the hybridoma microtitre plates were transferred to the cell plates and incubated in a 5 percent $CO_2$ incubator for 5 days. The wells that served as the positive controls were aspirated until empty and 100 microliters of sodium azide ($NaN_3$) or cycloheximide was added. After 5 days of treatment, the plates were then emptied by inverting and blotting dry. Room temperature DPBS (Dulbecco's phosphate buffered saline) containing $MgCl_2$ and $CaCl_2$ was dispensed into each well from a multichannel squeeze bottle, tapped 3 times, emptied by inversion and then blotted dry. 50 microliters of the fluorescent calcein dye diluted in DPBS containing $MgCl_2$ and $CaCl_2$ was added to each well and incubated at 37° C. in a 5% $CO_2$ incubator for 30 minutes. The plates were read in a Perkin-Elmer HTS7000 fluorescence plate reader and the data was analyzed in Microsoft Excel. The results are tabulated in FIG. 1. The AR37A335.8 hybridoma produced specific cytotoxicity of 16 percent in LnCap cells, which was 21 and 30 percent, of the cytotoxicity obtained with the positive controls sodium azide and cycloheximide respectively. Results from FIG. 1 demonstrated that the cytotoxic effects of AR37A335.8 were not proportional to the binding levels on the cancer cell types. There was a greater level of cytotoxicity produced in the LnCap cells as compared to the PC-3 cells, although the level of binding in the PC-3 cells was higher. Therefore, binding was not necessarily predictive of the outcome of antibody ligation of its cognate antigen, and was a non-obvious finding. This suggested that the context of antibody ligation in different cells determined cytoxicity, rather than just antibody binding. As tabulated in FIG. 1, AR37A335.8 did not produce cytotoxicity in the CCD-27sk normal cell line. The known non-specific cytotoxic agents cycloheximide and $NaN_3$ generally produced cytotoxicity as expected.

EXAMPLE 2

Antibody Production

AR37A335.8 monoclonal antibody was produced by culturing the hybridoma in CL-1000 flasks (BD Biosciences, Oakville, ON) with collections and reseeding occurring twice/week. Standard antibody purification procedures with Protein G Sepharose 4 Fast Flow (Amersham Biosciences, Baie d'Urfé, QC) were followed. It is within the scope of this invention to utilize monoclonal antibodies that are human, de-immunized, humanized, chimerized or murine.

AR37A335.8 was compared to a number of both positive (anti-EGFR (C225, IgG1, kappa, 5 micrograms/mL, Cedarlane, Hornby, ON), cycloheximide (CHX, 0.5 micromolar, Sigma, Oakville, ON), and $NaN_3$ (0.1%, Sigma, Oakville, ON)) and negative (MPC-11 (antigenic specificity unknown, IgG2b, kappa, 20 micrograms/mL, BD Biosciences, Oakville, ON) controls as well as a buffer diluent control in a cytotoxicity assay (FIG. 2). Colon (DLD-1 and Lovo) and ovarian (OVCAR-3) cancer, and non-cancer lung (Hs888.Lu) cell lines were tested (all from the ATCC, Manassas, Va.). Calcein AM was obtained from Molecular Probes (Eugene, Oreg.). The assays were performed according to the manufacturer's instructions with the changes outlined below. Cells were plated before the assay at the predetermined appropriate density. After 2 days, 100 microliters of purified antibody or controls were diluted into media, and then transferred to the cell plates and incubated in a 5 percent $CO_2$ incubator for 5 days. The plates were then emptied by inverting and blotted dry. Room temperature DPBS containing $MgCl_2$ and $CaCl_2$ was dispensed into each well from a multichannel squeeze bottle, tapped 3 times, emptied by inversion and then blotted dry. 50 microliters of the fluorescent calcein dye diluted in DPBS containing $MgCl_2$ and $CaCl_2$ was added to each well and incubated at 37° C. in a 5 percent $CO_2$ incubator for 30 minutes. The plates were read in a Perkin-Elmer HTS7000 fluorescence plate reader and the data was analyzed in Microsoft Excel and the results were tabulated in FIG. 2. Each antibody received a score between 5 and 50 based on the average cytotoxicity observed in four experiments tested in triplicate, and a score between 25 and 100 based on the variability observed between assays. The sum of these two scores (the cytotoxicity score) is presented in FIG. 2. A cytotoxicity score of greater than or equal to 55 was considered to be positive on the cell line tested. The AR37A335.8 antibody produced cytotoxicity in the Lovo and DLD-1 colon cancer cell lines relative to both isotype and buffer negative controls. The AR37A335.8 antibody did not produce cytotoxicity in the OVCAR-3 ovarian cancer cell line. Importantly, AR37A335.8 did not produce specific cytotoxicity against the non-cancer cell line Hs888.Lu, indicating that the antibody was specific for cancer cells. The chemical cytotoxic agents induced their expected non-specific cytotoxicity.

Binding of AR37A335.8 antibodies to the above-mentioned panel of cancer and normal human cell lines was assessed by flow cytometry (FACS). Cells were prepared for FACS by initially washing the cell monolayer with DPBS (without $Ca^{++}$ and $Mg^{++}$). Cell dissociation buffer (INVITROGEN, Burlington, ON) was then used to dislodge the cells from their cell culture plates at 37° C. After centrifugation and collection, the cells were resuspended in DPBS containing $MgCl_2$, $CaCl_2$ and 2 percent fetal bovine serum at 4° C. (staining media) and counted, aliquoted to appropriate cell density, spun down to pellet the cells and resuspended in staining media at 4° C. in the presence of test antibody (AR37A335.8) or control antibodies (isotype control, anti-EGFR) at 20 micrograms/mL on ice for 30 minutes. Prior to the addition of Alexa Fluor 488-conjugated secondary antibody the cells were washed once with staining media. The Alexa Fluor 488-conjugated antibody in staining media was then added for 30 minutes. The cells were then washed for the final time and resuspended in fixing media (staining media containing 1.5% paraformaldehyde). Flow cytometric acquisition of the cells was assessed by running samples on a FACScan using the CellQuest software (BD Biosciences, Oakville, ON). The forward (FSC) and side scatter (SSC) of the cells were set by adjusting the voltage and amplitude gains on the FSC and SSC detectors. The detectors for the fluorescence (FITC) channel was adjusted by running cells stained only with Alexa Fluor 488-conjugated secondary antibody such that cells had a uniform peak with a median fluorescent intensity of approximately 1-5 units. For each sample, approximately 10,000 stained fixed cells were acquired for analysis and the results are presented in FIG. 3.

FIG. 3 presents the mean fluorescence intensity fold increase above isotype control. Representative histograms of AR37A335.8 antibodies were compiled for FIG. 4. AR37A335.8 showed binding to all cell lines tested. These data demonstrate that AR37A335.8 exhibited functional specificity in that although there was clear binding to all cancer types tested, there was only associated cytotoxicity with Lovo and DLD-1 colon cancer cells.

EXAMPLE 3

In vivo Tumor Experiments with MDA-MB-231 Cells

Figure 5:
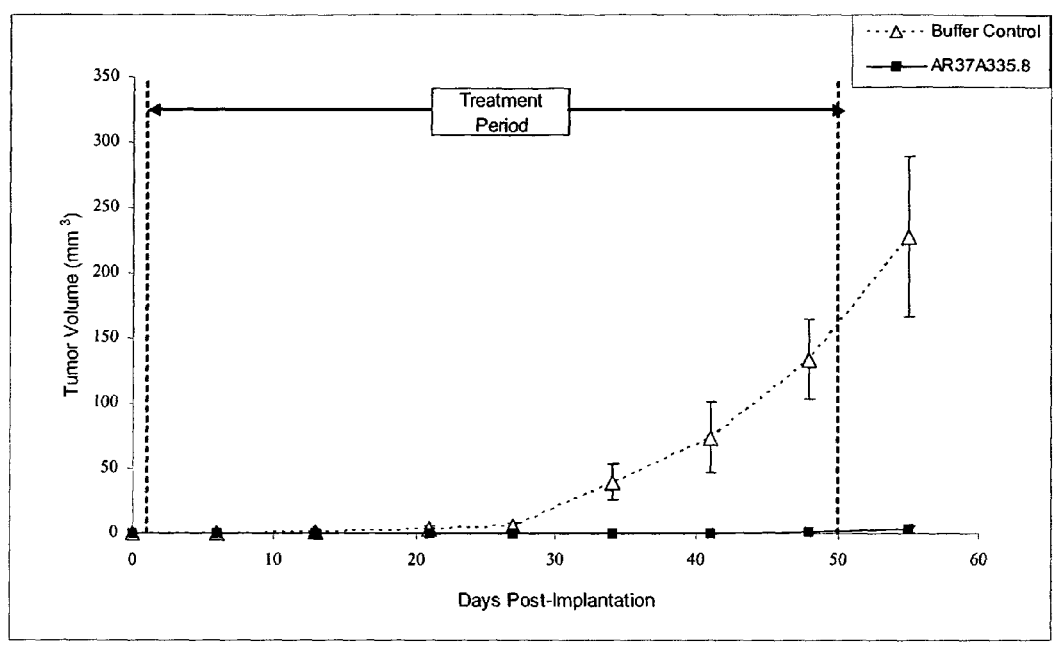
FIG. 5 demonstrates the effect of AR37A335.8 on tumor growth in a prophylactic MDA-MB-231 breast cancer model. The vertical dashed lines indicate the period during which the antibody was administered. Data points represent the mean±SEM.
Figure 6:
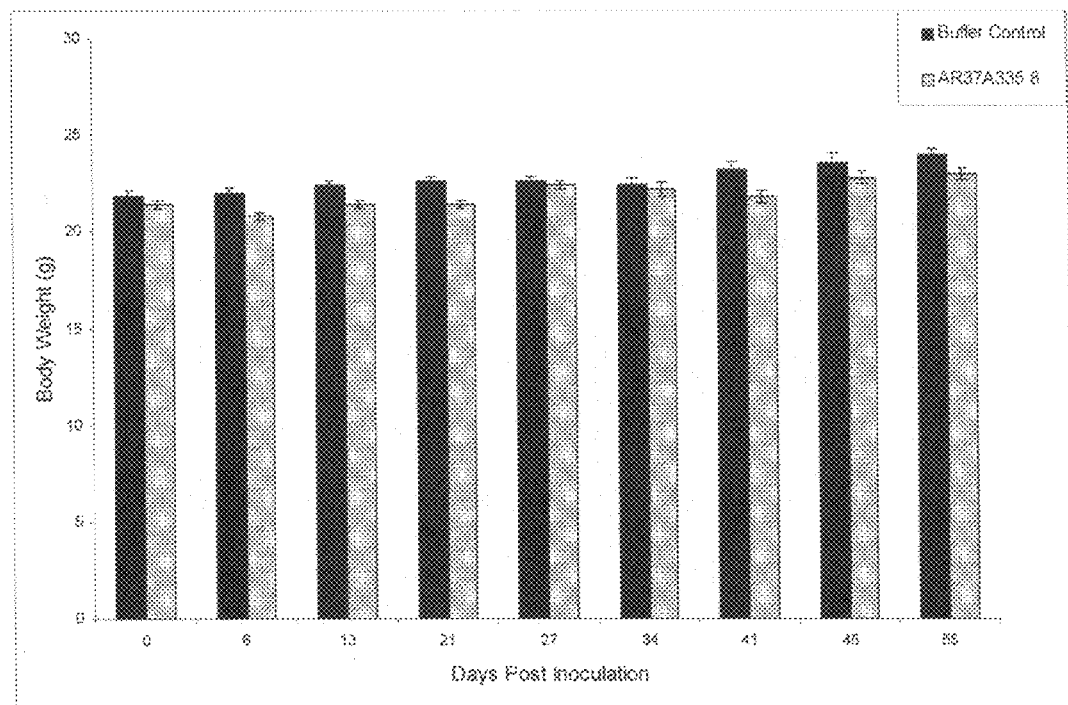
FIG. 6 demonstrates the effect of AR37A335.8 on body weight in a prophylactic MDA-MB-231 breast cancer model. Data points represent the mean±SEM.

With reference to FIGS. 5 and 6, 4 to 6 week old female SCID mice were implanted with 5 million human breast cancer cells (MDA-MB-231) in 100 microliters saline injected subcutaneously in the scruff of the neck. The mice were randomly divided into 2 treatment groups of 5. On the day after implantation, 20 mg/kg of AR37A335.8 test antibody or buffer control was administered intraperitoneally to each cohort in a volume of 300 microliters after dilution from the stock concentration with a diluent that contained 2.7 mM KCl, 1 mM $KH_2PO_4$, 137 mM NaCl and 20 mM $Na_2HPO_4$. The antibody and control samples were then administered once per week for the duration of the study, a total of 8 doses, in the same fashion. Tumor growth was measured about every seventh day with calipers. Body weights of the animals were recorded once per week for the duration of the study. At the end of the study all animals were euthanized according to CCAC guidelines.

AR37A335.8 markedly reduced tumor growth in the MDA-MB-231 in vivo prophylactic model of human breast cancer. On day 55 post-implantation, 5 days after the last treatment dose, the mean tumor volume in the AR37A335.8 treated group was 98.8 percent lower than the tumor volume in the buffer control-treated group (FIG. 5). The tumor volume at the end of the study was significantly different from that of the control (p=0.0064, t-test).

There were no clinical signs of toxicity throughout the study. Body weight measured at weekly intervals was a surrogate for well-being and failure to thrive. As seen in FIG. 6, the body weights for both control and AR37A335.8-treated groups increased over the course of the study.

In conclusion, AR37A335.8 was well-tolerated and decreased the tumor burden in this human breast cancer xenograft model.

EXAMPLE 4

In vivo Tumor Experiments with SW1116 Cells

With reference to FIGS. 7 and 8, 4 to 6 week old female SCID mice were implanted with 5 million human colon cancer cells (SW1116) in 100 microliters saline injected subcutaneously in the scruff of the neck. The mice were randomly divided into 2 treatment groups of 5. On the day after implantation, 20 mg/kg of AR37A335.8 test antibody or buffer control was administered intraperitoneally to each cohort in a volume of 300 microliters after dilution from the stock concentration with a diluent that contained 2.7 mM KCl, 1 mM $KH_2PO_4$, 137 mM NaCl and 20 mM $Na_2HPO_4$. The antibody and control samples were then administered once per week for the duration of the study, a total of 8 doses, in the same fashion. Tumor growth was measured about every seventh day with calipers. Body weights of the animals were recorded once per week for the duration of the study. At the end of the study all animals were euthanized according to CCAC guidelines.

Figure 7:
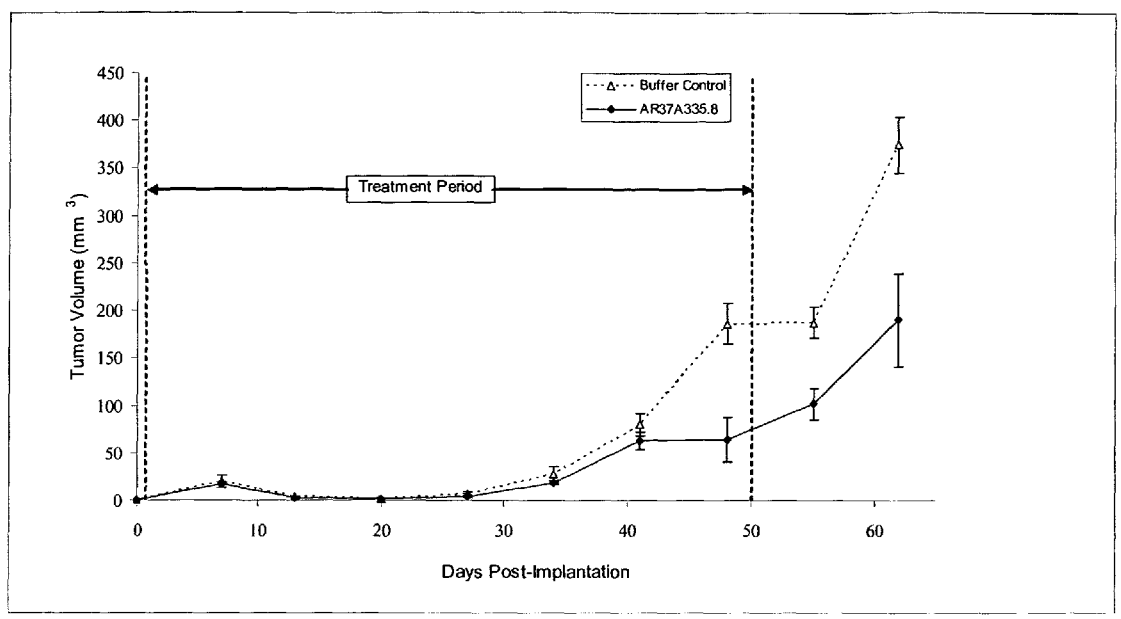
FIG. 7 demonstrates the effect of AR37A335.8 on tumor growth in a prophylactic SW1116 colon cancer model. The vertical dashed lines indicate the period during which the antibody was administered. Data points represent the mean±SEM.

Treatment with AR37A335.8 resulted in tumor growth inhibition in the SW1116 in vivo prophylactic model of human colon cancer. On day 55 post-implantation, 5 days after the last treatment dose, the mean tumor volume in the AR37A335.8 treated group was 48.7 percent lower than the tumor volume in the buffer control-treated group (FIG. 7). Treatment with AR37A335.8 resulted in a tumor volume that was significantly less than that of the control (p=0.0055).

Figure 8:
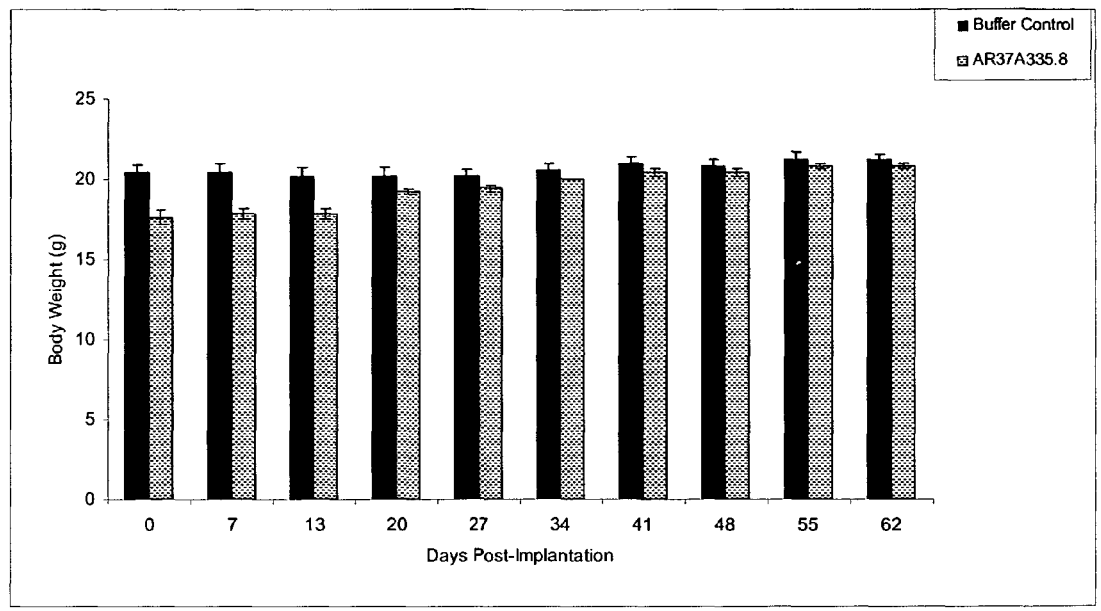
FIG. 8 demonstrates the effect of AR37A335.8 on body weight in a prophylactic SW1116 colon cancer model. Data points represent the mean±SEM.

There were no clinical signs of toxicity throughout the study. Body weight measured at weekly intervals was a surrogate for well-being and failure to thrive. As seen in FIG. 8, the body weights of the control or AR37A335.8-treated groups did not decrease over the course of the study. There was also no difference in body weight between the two groups at the end of the treatment period (Day 48) or at the end of the post-treatment follow up period. (Day 63).

Therefore AR37A335.8 was well-tolerated and decreased the tumor burden in this human colon cancer xenograft model.

EXAMPLE 5

Determination of Cross-Reactivity Between AR37A335.8 and Anti-CD44 H460-16-2

Figure 9:
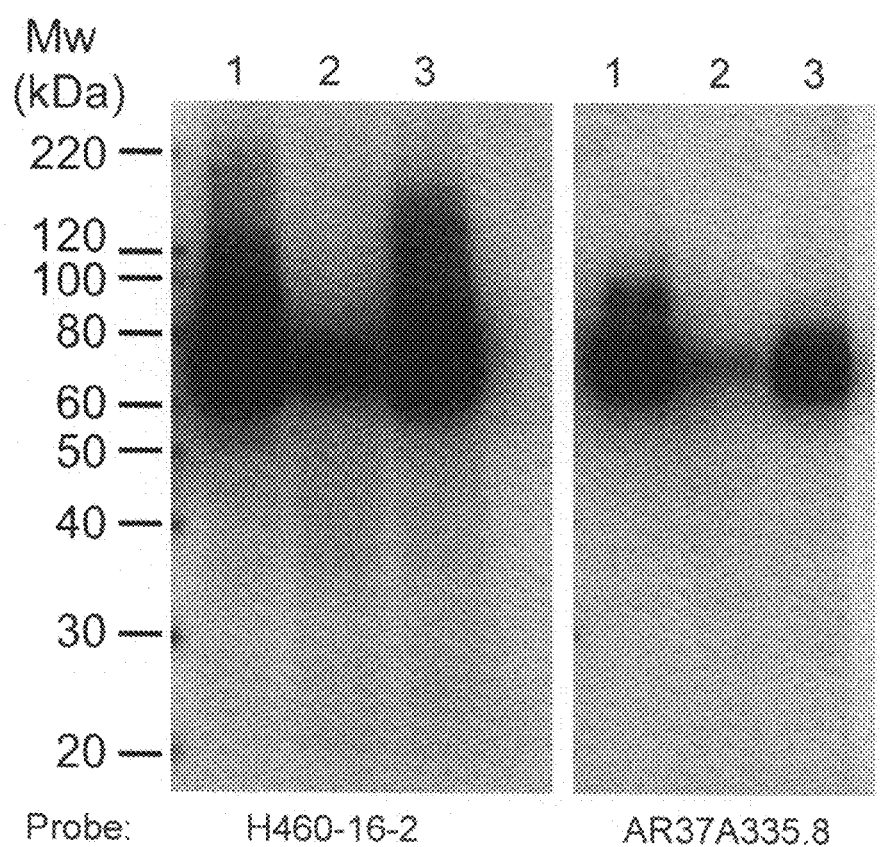
FIG. 9. Western blot, of samples obtained from the total membrane fraction of MDA-MB-231 cells (lane 1) and from whole cell lysates of PC-3 (lane 2) and CCD-27sk (lane 3) cell lines, probed with AR37A335.8 and H460-16-2
Figure 10:
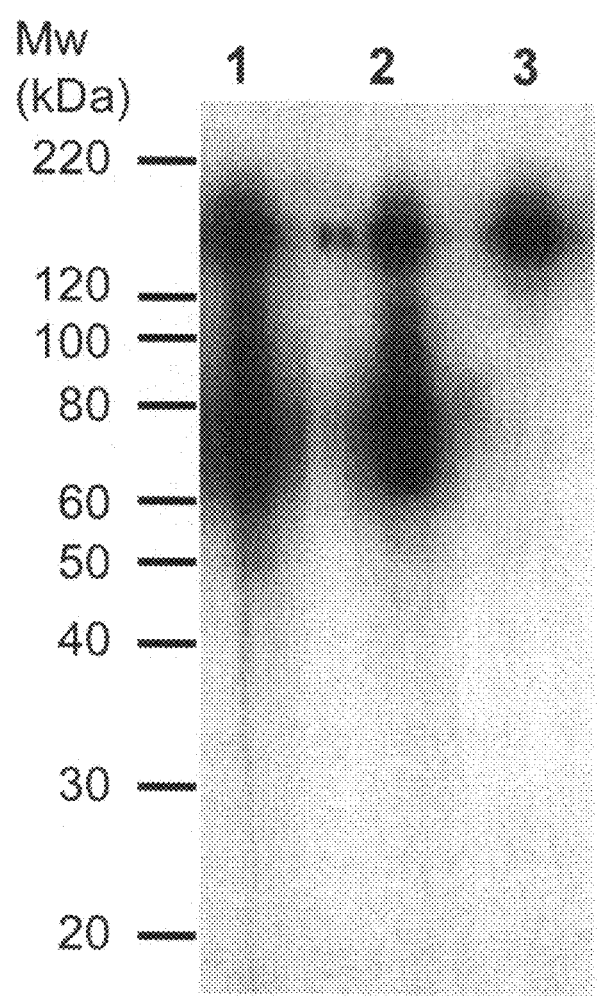
FIG. 10. Western blot of an immunocomplex prepared by immunoprecipitation, with the anti-CD44 H460-16-2, from the total membrane fraction of the MDA-MB-231 cell line. Individual lanes of the blot were probed with AR37A335.8 (lane 1), H460-16-2 (lane 2) or with the isotype control antibody (lane 3).

Western blots of total membrane fractions and of whole cell lysates, were probed with the monoclonal antibody AR37A335.8 and with the anti-CD44 monoclonal antibody H460-16-2. Briefly, 20 micrograms of total membrane fraction isolated from MDA-MB-231 cells grown in culture, and 40 micrograms of whole cell lysate prepared from PC-3 and CCD-27sk cells grown in culture, were analyzed by electrophoresis on a 10% SDS-polyacrylamide gel, under non-reducing conditions. After electrotransfer onto PVDF membranes, the blots were probed with the antibodies AR37A335.8 and H460-16-2, following a standard protocol for Western blotting. The results from the Western blot probed with the monoclonal antibody AR37A335.8 revealed a strong similarity with that obtained with anti-CD44 monoclonal antibody H460-16-2 (FIG. 9), suggesting that both antibodies might recognize the same antigen, i.e. CD44. In order to determine whether AR37A335.8 cross-reacted with the CD44 molecule, it was used as a probe on a Western blot of an immunoprecipitate complex obtained with the anti-CD44 H460-16-2 from the total membrane fraction of cells grown in culture. Briefly 300 micrograms of MDA-MB-231 total membrane fraction (1 mg/mL final protein concentration) was incubated with H460-16-2-conjugated protein G Sepharose beads for 2 hours at 4° C. After washing, the beads were boiled in 1× non-reducing SDS-PAGE sample buffer and the sample was analyzed by electrophoresis on a 10% preparative polyacrylamide gel. After electrotransfer onto a PVDF membrane, individual lanes on the blot were probed with the antibodies AR37A335.8, H460-16-2 and with an IgG1 isotype control according to a standard Western blot protocol. All primary antibodies were used at a concentration of 5 micrograms/mL. The image of the resulting blot (FIG. 10) shows that both AR37A335.8 and H460-16-2 cross-reacted with the same antigen, therefore demonstrating that the antibody AR37A335.8 also recognizes an epitope contained within the CD44 molecule.

EXAMPLE 6

Human Prostate Tumor Tissue Staining

IHC studies were conducted to further evaluate the binding of H460-16-2 to human prostate tumor tissue. IHC optimization studies were performed previously in order to determine the conditions for further experiments. H460-16-2 monoclonal antibodies were produced and purified as described above.

Binding of antibodies to 53 human prostate tumor and 3 normal prostate tissues was performed using a human, prostate normal and tumor tissue microarray (Imgenex, San Diego, Calif.). Tissue sections were deparaffinized by drying in an oven at 58° C. for 1 hour and dewaxed by immersing in xylene 5 times for 4 minutes each in Coplin jars. Following treatment through a series of graded ethanol washes (100%-75%) the sections were re-hydrated in water. The slides were immersed in 10 mM citrate buffer at pH 6 (Dako, Toronto, Ontario) then microwaved at high, medium, and low power settings for 5 minutes each and finally immersed in cold PBS. Slides were then immersed in 3% hydrogen peroxide solution for 6 minutes, washed with PBS three times for 5 minutes each, dried, incubated with Universal blocking solution (Dako, Toronto, Ontario) for 5 minutes at room temperature. H460-16-2, monoclonal mouse anti-prostate specific membrane antigen (PSMA; clone 1D11, North West Biotherapeutics, Bothell, Wash.) or isotype control antibody (directed towards *Aspergillus niger* glucose oxidase, an enzyme which is neither present nor inducible in mammalian tissues; Dako, Toronto, Ontario) were diluted in antibody dilution buffer (Dako, Toronto, Ontario) to its working concentration (5 micrograms/mL for each antibody except for anti-PSMA which was diluted to 2 micrograms/mL) and incubated for 1 hour at room temperature. The slides were washed with PBS 3 times for 5 minutes each. Immunoreactivity of the primary antibodies was detected/visualized with HRP conjugated secondary antibodies as supplied (Dako Envision System, Toronto, Ontario) for 30 minutes at room temperature. Following this step the slides were washed with PBS 3 times for 5 minutes each and a color reaction developed by adding DAB (3,3'-diaminobenzidine tetrahydrachloride, Dako, Toronto, Ontario) chromogen substrate solution for immunoperoxidase staining for 10 minutes at room temperature. Washing the slides in tap water terminated the chromogenic reaction. Following counterstaining with Meyer's Hematoxylin (Sigma Diagnostics, Oakville, ON), the slides were dehydrated with graded ethanols (75-100%) and cleared with xylene. Using mounting media (Dako Faramount, Toronto, Ontario) the slides were coverslipped. Slides were microscopically examined using an Axiovert 200 (Ziess Canada, Toronto, ON) and digital images acquired and stored using Northern Eclipse Imaging Software (Mississauga, ON). Results were read, scored and interpreted by a histopathologist.

FIG. 11 presents a summary of the results of H460-16-2 staining of an array of human normal and tumor prostate tissues. From the table, 19/53 (36%) of the tested tumors were positive for H460-16-2. H460-16-2 was specific for tumor cells and stroma fibroblasts. Cellular localization was mostly membranous and cytoplasmic membranous with or without luminal localization. The percentage of positive cells ranged from <10%→50% indicating heterogenous binding of the antibody to tumor cells. The relation of the antibody binding to tumors' stages could not be assessed properly due to a discrepancy in the number of tumors among different tumor stages, being 1/1 (100%), 4/12 (33%), 0/2 (0%) and 11/33 (33%) to stage I, II, III and IV, respectively.

There was higher binding to Gleason score G3-G4 (36%) than to G1-G2 (25%). The Gleason score is a system of grading prostate cancer. The Gleason grading system assigns a grade to each of the two largest areas of cancer in the tissue samples. Grades range from 1 to 5 with 1 being the least aggressive and 5 the most aggressive. Grade 3 tumors, for example, seldom have metastases, but metastases are common with grade 4 or grade 5. The two grades are then added together to produce a Gleason score. A score of 2 to 4 is considered low grade; 5 through 7, intermediate grade; and 8 through 10, high grade. A tumor with a low Gleason score typically grows slowly enough that it may not pose a significant threat to the patient in his lifetime.

All 3 normal prostate tissue sections were positive for the antibody. However, the tissue specificity was for myoepithelium and stromal fibroblasts and spared the glandular epithelium. FIG. 12 demonstrates the heterogeneity of the binding of H460-16-2 to tested prostate tumors: 10/53, 6/53, 3/53 positive tumors were in the categories of <10-10%, <50-50% and >50%, respectively. As a result of its binding to prostate cancer cells, the therapeutic benefit of H460-16-2 can potentially be extended to the treatment of prostate cancer.

EXAMPLE 7

Human Liver Tumor Tissue Staining

To further evaluate the binding of H460-16-2 to human liver tumor tissues, the antibody was tested on a liver tumor tissue array (Imgenex, San Diego, Calif.). The following information was provided for each patient: age, sex, organ and diagnosis. The staining procedure used was the same as the one disclosed in Example 6. The same negative control antibody was used as described above. The positive control antibody used was anti-AFP (alpha 1 fetoprotein; clone AFP-11, Abcam, Cambridge, Mass.). All antibodies were used at a working concentration of 5 micrograms/mL except for anti-AFP which was used at a working concentration of 10 micrograms/mL.

Figure 14:
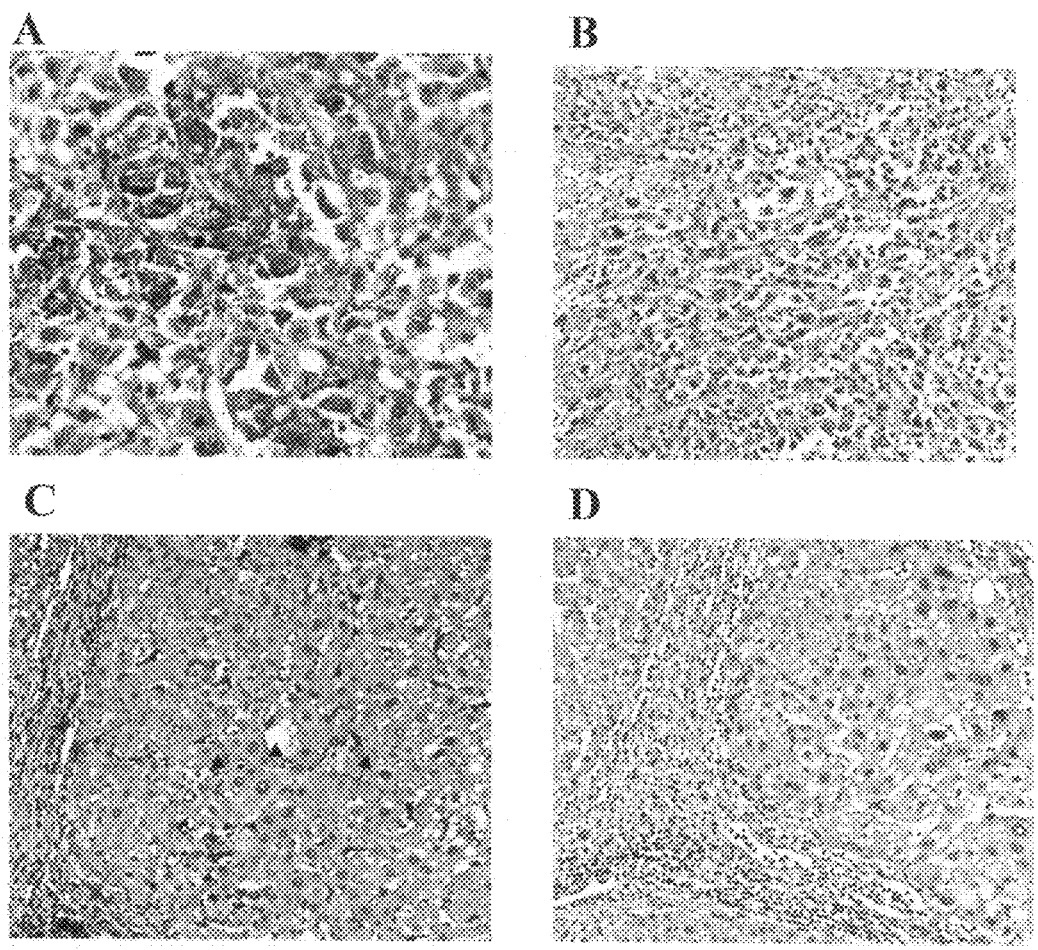
FIG. 14. Representative micrographs showing the binding pattern on liver tumor tissue obtained with H460-16-2 (A) or the isotype control antibody (B) and on non-neoplastic liver tissue obtained with H460-16-2 (C) or the isotype control antibody (D) from a human tissue microarray. H460-16-2 displayed strong positive staining for the tumor cells and was limited to staining on sinusoidal cells (black arrows) and infiltrating lymphocytes (green arrows) on the non-neoplastic liver tissue. Magnification is 200×.

As disclosed in FIG. 13, the H460-16-2 antibody showed binding to 21/49 (43%) of tested liver cancers, including 11/37 (30%) of primary, 7/8 (88%) of metastatic hepatocellular carcinoma, 1/2 (50%) of primary and 2/2 (100%) of metastatic cholangiocarcinomas. The antibody showed significant higher binding to advanced tumors' stages III and IV in comparison with early stages I and II (p=0.03) [stage I, 0/2 (0%); stage II, 2/17 (12%); stage III, 8/16 (50%) and stage IV, 6/8 (75%)]. H460-16-2 was specific for tumor cells and infiltrating inflammatory cells. Cellular localization was mainly membranous. Some tumors also displayed a diffuse cytoplasmic staining pattern. The antibody bound to 9/9 of non-neoplastic liver tissues (FIG. 14). However, the binding was restricted to the sinusoidal cells and infiltrating lymphocytes. The H460-16-2 antigen appears to be specifically expressed on advanced liver tumor tissue. H460-16-2 therefore has potential as a therapeutic drug in the treatment of liver cancer.

EXAMPLE 8

Apoptosis Study on MDA-MB-231 Xenograft Tumor Tissue Derived from SCID Mice Treated with H460-16-2

H460-16-2 has shown the ability to produce tumor growth suppression in a preventative and established MDA-MB-231 xenograft model in vivo (disclosed in Ser. No. 10/603,000). Using FACS, H460-16-2 has also demonstrated an effect on MDA-MB-231 cell cycling and this effect led to a dose dependent increase in the number of apoptotic cells (disclosed in Ser. No. 10/810,165). To further elucidate the mechanism of action for H460-16-2, the effect of H460-16-2 treatment upon apoptosis in MDA-MB-231 tumors grown in vivo in a xenograft model of breast cancer was investigated.

At the end of the treatment period in a MDA-MB-231 established model of human breast cancer, mice in the H460-16-2 group showed an average tumor volume that was 68.8% of the volume in the buffer control treated group (similar process as disclosed in Example 10). Two days after the end of treatment, 4 mice per group were randomly selected and the tumors harvested. Harvested tumors were bisected into half and fixed in 10% buffered formnalin. After fixation, the tissue was further trimmed to give an approximately 2 mm tumor slice for paraffin embedding. Reasonable efforts were made to have the entire cross section of the tumor represented. The tissues were embedded in paraffin, sectioned and mounted on slides for staining at the clinical research laboratory in the Toronto General Hospital (Toronto, ON).

Apoptosis was assessed in the tissue sections using the ApopTag® Plus Peroxidase In Situ Apoptosis Detection Kit (S7101) from Chemicon International (Temecula, Calif.). The ApopTag Kit is based on the TUNEL assay and examines apoptosis by assessing DNA fragmentation. Terminal deoxynucleotidyl transferase (TdT) is used to end label the fragments with digoxigenin-dNTP. Incorporated digoxigenin-dNTP was detected using an anti-digoxigenin peroxidase reagent. The protocol followed was as outlined in the manual provided with the kit. ApopTag staining and cellular morphology was visualized using light microscopy. For each section, 4 separate regions from the viable area of the tumor were used to count stained cells. Care was taken not to focus on necrotic regions of the tumor. Counts from the 4 separate regions were added together to give a total count representative of that section. The counts were repeated 3 times for each section (each time focusing on 4 regions). The totals obtained from the 3 counts were used to give an average for the section. Subsequently, average counts for the different treatment groups were calculated. As shown in FIG. 15, the buffer control group yielded an average total score of 31.5 cells (±14.62) while the H460-16-2 treated group yielded an average total score of 42.5 cells (±3.70). Therefore, there is a trend towards increased apoptosis with H460-16-2 treatment as determined using a TUNEL assay.

Serial sections of the ApoTag stained tumors were subsequently H & E stained and these were examined for apoptotic cells using morphological criteria such as deletion of single cells, cell shrinkage and compaction of chromatin into a dense mass. Counts for cells meeting these criteria were done as described in the section above to give average counts for the treatment groups. A positive control slide (of tissue from a 3-5 day post lactating normal rodent mammary gland) was included in the kit and was stained along with the test slides. As shown in FIG. 15, the buffer control group yielded an average total score of 17 cells (±5.29) while the H460-16-2 treated group yielded an average total score of 22.5 cells (±4.20). Therefore, there is a trend towards increased apoptosis with H460-16-2 treatment as determined using cellular morphology.

EXAMPLE 9

Chimerization of H460-16-2

1.0 Cloning Variable Region Genes Into Sequencing Vectors

To facilitate production of antibody chimera, the genes encoding the variable regions of both heavy and light chains were separately cloned into the commercial sequencing vector pCR2.1.

1.1 Isolation of mRNA

Messenger ribonucleic acid (mRNA) was isolated from a culture of confluent Master Cell Bank H460-16-2 hybridoma cells using QuickPrep™ Micro mRNA Purification Kit (GE Healthcare, Piscataway, N.J.). mNA was stored at −80° C. until required for further use.

1.2 RT-PCR Amplification of Variable Region Genes

Separate reactions were carried out to amplify the light and heavy chain variable regions. Reverse transcriptase polymerase chain reaction (RT-PCR) synthesized complimentary deoxynucleic acid (cDNA) from the mRNA template, then specifically amplified the targeted gene.

For the light chain, 1 microliter of mRNA was heated at 65° C. for 10 minutes, and then cooled on ice. RT-PCR reactions were prepared using SuperScript™ One-Step RT-PCR with Platinum® Taq (Invitrogen, Burlington, ON) with 12.5 microliters of 2× RT-PCR reaction mix (Invitrogen, Burlington, ON), 1 microliter of 20 pmol/microliter MuIgκ$V_L$5'-F primer (Novagen, Mississauga, ON), 1 microliter of 20 pmol/microliter MuIgκ$V_L$3'-1 primer (Novagen, Mississauga, ON), 0.5 microliters RT/Platinum Taq mix (Invitrogen, Burlington, ON), 0.4 microliters of 50 mM MgSO$_4$ (Invitrogen, Burlington, ON) and water up to 25 microliters. A second set of reactions was also prepared as above except that the forward primer used was MuIgκV$_L$5'-C primer (Novagen, Mississauga, ON) instead of MuIgκV$_L$5'-F. Reactions were heated in the thermocycler for 40 minutes at 50° C., followed by 94° C. for 2 minutes. The polymerase chain reaction (PCR) reaction was performed for 30 cycles of 94° C. for 30 seconds, 55° C. for 1 minute and 72° C. for 1 minute. Finally the PCR products were heated at 72° C. for 10 minutes, and then stored at 4° C. PCR product was purified using QIAquick PCR Purification Kit (QIAGEN, Mississauga, ON).

For the heavy chain, 1 microliter of mRNA was heated at 65° C. for 10 minutes, and then cooled on ice. RT-PCR reactions were prepared using SuperScript™ One-Step RT-PCR with Platinum® Taq (Invitrogen, Burlington, ON) with 12.5 microliters of 2× RT-PCR reaction mix (Invitrogen, Burlington, ON), 1 microliter of 5 pmol/microliter MuIgV$_H$5'-A primer (Novagen, Mississauga, ON), 1 microliter of 10 pmol/microliter MuIgV$_H$5'-B primer (Novagen, Mississauga, ON), MuIgV$_H$5'-C primer (Novagen, Mississauga, ON), 1 microliter of 5 pmol/microliter MUIgV$_H$5'-D primer (Novagen, Mississauga, ON), 1 microliter of 5 pmol/microliter MuIgV$_H$5'-F primer (Novagen, Mississauga, ON), 1 microliters of 5 pmol/microliter MuIgGV$_H$3'-2 primer (Novagen, Mississauga, ON), 0.5 microliters RT/Platinum® Taq mix (Invitrogen, Burlington, ON), 0.4 microliters of 50 mM MgSO$_4$ (Invitrogen, Burlington, ON) and water up to 25 microliters. Reactions were heated in the thermocycler for 40 minutes at 50° C., followed by 94° C. for 2 minutes. The PCR reaction was performed for 30 cycles of 94° C. for 30 seconds, 55° C. for 1 minute and 72° C. for 1 minute. Finally the PCR products were heated at 72° C. for 10 minutes, and then stored at 4° C.

Figure 16:
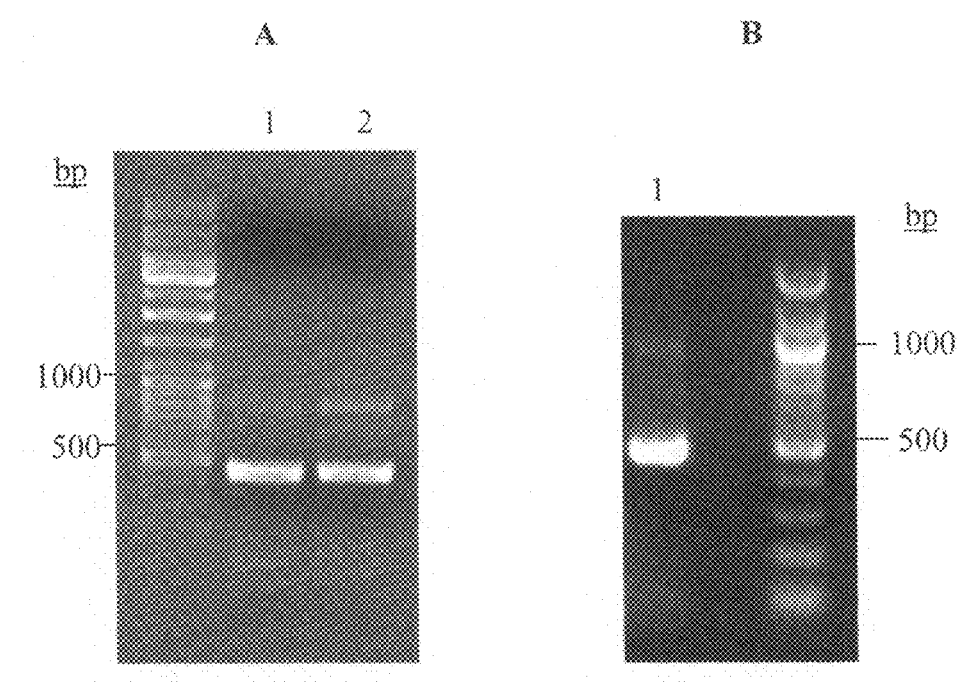
FIG. 16. RT-PCR products from H460-16-2 mRNA. Light chain reactions (Panel A) were amplified using MuIgκ$V_L$ 5'-F (Lane 1) or MuIgκ$V_L$ 5'-C (Lane 2) forward primer. The heavy chain reaction (Panel B) was amplified using a mix of MuIg$V_H$ 5'-A, B, C, D and F forward primers. Both light chain reactions (Panel A, Lanes 1 and 2) demonstrate a strong band at 450 bp as well as a weaker band at 850 bp. The 450 bp band is the target band containing the H460-16-2 Vk gene. The heavy chain reaction (Panel B, Lane 1) demonstrates a strong band at 500 bp and a weak band at 1000 bp. The band at 500 bp is the target band corresponding to the H460-16-2 Vh gene.

FIG. 16 shows the result of the RT-PCR reactions. Light chain reactions (Panel A) were amplified using MuIgκV$_L$ 5'-F (Lane 1) or MuIgκV$_L$ 5'-C (Lane 2) forward primer. The heavy chain reaction (Panel B) was amplified using a mix of MUIgV$_H$ 5'-A, B, C, D and F forward primers. Both of the light chain reactions (Panel A, Lanes 1 and 2) demonstrate a strong band at 450 bp as well as a weaker band at 850 bp. The 450 bp band is the target band containing the H460-16-2 Vk gene. The heavy chain reaction (Panel B, Lane 1) demonstrates a strong band at 500 bp and a weak band at 1000 bp. The band at 500 bp is the target band corresponding to the H460-16-2 Vh gene. All PCR products were purified using QIAquick PCR Purification Kit (QIAGEN, Mississauga, ON).

1.3 Cloning Into Sequencing Vectors

Light and heavy chain purified PCR products were separately cloned into pCR2.1 vectors using the TOPO TA Cloning® Kit (Invitrogen, Burlington, ON). Both the light and heavy chain reactions contained 2 microliters of the appropriate purified PCR product. Plasmids were transformed into One Shot® MAX Efficiency™ DH5α™-T1$^R$ E. coli (Invitrogen, Burlington, ON), as per manufacturer's instructions. For both the light and heavy chain transformations, 2 microliters of ligation reactions were used.

30 microliters of transformed cells from each reaction was plated onto pre-warmed Lennox L broth (LB) agar (Sigma, Oakville, ON) plates containing 50 micrograms/mL ampicillin (Sigma, Oakville, ON) and 40 microliters of 40 mg/mL 5-bromo-4-chloro-3-indolyl-beta-D-galactopyranoside (X-gal, Caledon Laboratories, Georgetown, ON) in N,N-dimethylformamide (Caledon Laboratories, Georgetown, ON). The plates were inverted and incubated at 37° C. overnight.

Five single white clones from each of the H460-16-2 Vk transformed plates and ten single white clones from the H460-16-2 Vh transformed plate were selected and used to inoculate 4 mL of LB broth (Sigma, Oakville, ON) containing 50 micrograms/mL ampicillin (Sigma, Oakville, ON). Cultures were grown overnight at 37° C. shaking at 200 rpm. Plasmids were isolated from each culture using QIAprep Spin Miniprep Kit (QIAGEN, Mississauga, ON).

Recovered plasmids were digested with EcoR I to determine the size of the insert. The H460-16-2 Vk digests contained 5 microliters of plasmid, 0.02 microliters of 50 U/microliter EcoR I (Amersham Biosciences, Baie d'Urfé, QC), 1.5 microliters of 10× buffer H (Amersham Biosciences, Baie d'Urfé, QC), 1.5 microliters of 0.1% bovine serum albumin (BSA) and 6.98 microliters of water. The H460-16-2 Vh digests contained 5 microliters of plasmid, 0.04 microliters of 50 U/microliter EcoR I (Amersham Biosciences, Baie d'Urfé, QC), 1.5 microliters of 10× buffer H (Amersham Biosciences, Baie d'Urfé, QC), 1.5 microliters of 0.1% BSA (Amersham Biosciences, Baie d'Urfé, QC) and 6.96 microliters of water. The plasmids were digested at 37° C. for 1 hour. 5 microliters of each digested plasmid was run on a 1.0% agarose gel.

Figure 17:
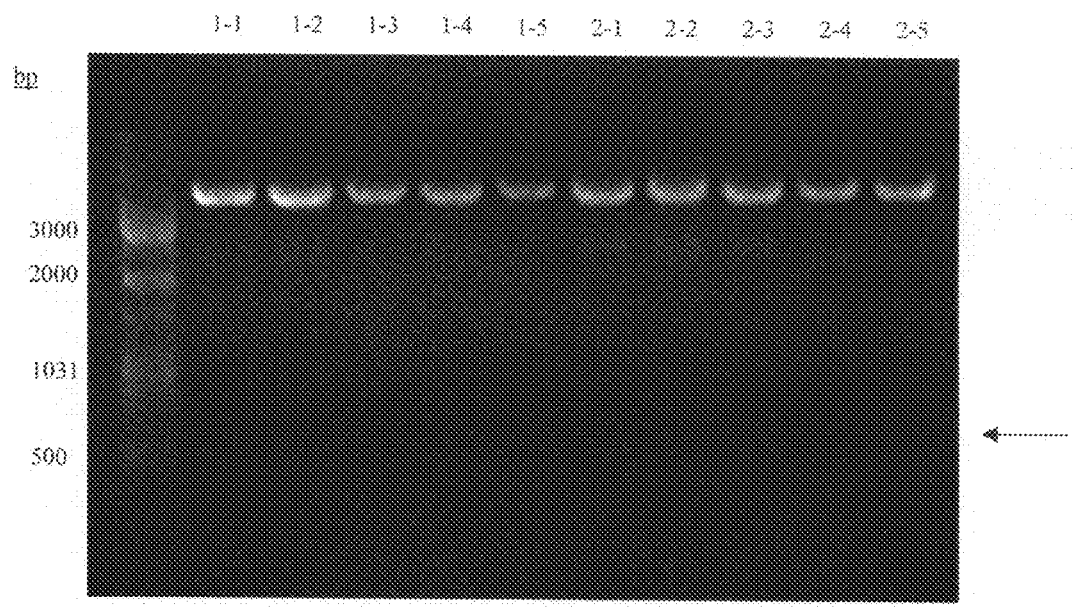
FIG. 17. EcoR I digested plasmids isolated from *E. coli* transformed with pCR2.1(H460-16-2 Vk). The clone number is indicated at the top. The first number indicates the forward primer used (1 for MuIgκ$V_L$5'-F and 2 for MuIgκ$V_L$5'-C), and the second number indicates the clone number (1-5). The molecular weight marker is indicated on the left. The arrow indicates the position of the desired H460-16-2 Vk inserts.

FIG. 17 shows pCR2.1 (H460-16-2 Vk) plasmids digested with EcoR I. The clone numbers are indicated at the top. The first number denotes the forward primer used (1 for MuIgκV$_L$5'-F and 2 for MuIgκV$_L$5'-C), and the second number denotes the clone number (1-5). The large band around 5000 bp is the pCR2.1 vector backbone. All clones except 2-4 have bands at 500 bp, the expected size of the H460-16-2 Vk insert (indicated by the arrow).

Figure 18:
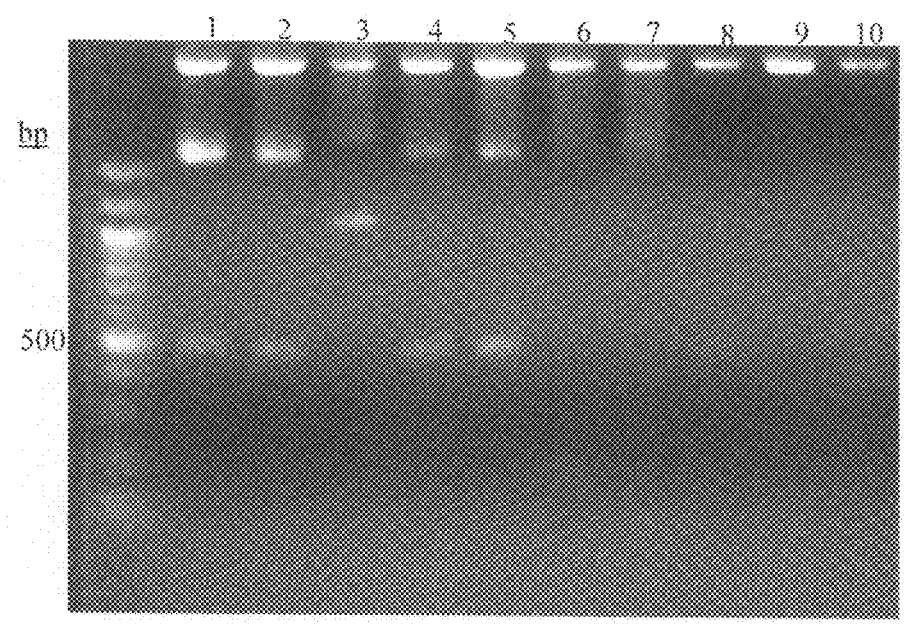
FIG. 18. EcoR I digested plasmids isolated from *E. coli* transformed with pCR2.1(H460-16-2 Vh). The clone number is indicated at the top. The molecular weight marker is indicated on the left. Clones 1, 2, 3, 4, 5 and 8 demonstrate the desired 500 bp band that corresponds to the H460-16-2 Vh gene.

FIG. 18 shows the pCR2.1 (H460-16-2 Vh) plasmids digested with EcoR I. Clones 1, 2, 3, 4, 5 and 8 demonstrate the desired 500 bp band that corresponds to the H460-16-2 Vh gene.

Some of the plasmids that contained appropriately sized inserts (Vk 1-1, Vk 1-2, Vk 1-3, Vk 2-1, Vk 2-2, Vk 2-3, Vh 1, Vh 4 and Vh 5) were sequenced at York University's Core Molecular Biology Facility (Toronto, ON). Sequences are given in FIG. 19 (SEQ ID NOS:1-8 and 36). The correct H460-16-2 Vk sequence was found in only clone 1-1. The remaining Vk clones contained an aberrant immunoglobulin gene. Clone 1-1 (pVkH460-16-2#1-1) was used for construction of the chimeric H460-16-2 IgG2 plasmid. None of the H460-16-2 Vh clones contained the correct H460-16-2 Vh sequence. The correct sequence was deduced from the alignment of the incorrect sequences and is listed in FIG. 19 as SEQ ID NO:36.

1.4 Cloning of H460-16-2 VH into Sequencing Vector (for Construction of Chimeric IgG2)

mRNA from above was used to amplify the H460-14-2 Vh gene. For the heavy chain, 1 microliter of mRNA was heated at 65° C. for 10 minutes, and then cooled on ice for 2 minutes. RT-PCR reactions were prepared using SuperScript™ One-Step RT-PCR with Platinum® Taq (Invitrogen, Burlington, ON) with 12.5 microliters of 2× RT-PCR reaction mix (Invitrogen, Burlington, ON), 1 microliter of 5 pmol/microliter MuIgV$_H$5'-A primer (Novagen, Mississauga, ON), 1 microliter of 10 pmol/microliter MuIgV$_H$5'-B primer (Novagen, Mississauga, ON), 1 microliter of 5 pmol/microliter MuIgV$_H$5'-D primer (Novagen, Mississauga, ON), 1 microliter of 5 pmol/microliter MuIgV$_H$5'-F primer (Novagen, Mississauga, ON), 1 microliter of 5 pmol/microliter MuIgGV$_H$3'-2 primer (Novagen, Mississauga, ON), 0.5 microliters RT/Platinum Taq mix (Invitrogen, Burlington, ON), 0.4 microliters of 50 mM MgSO$_4$ (Invitrogen, Burlington, ON) and water up to 25 microliters. Reactions were heated in the thermocycler for 40 minutes at 50° C., followed by 94° C. for 2 minutes. The PCR reaction was performed for 30 cycles of 94° C. for 30 seconds, 55° C. for 1 minute and 72° C. for 1 minute. Finally the PCR products were heated at 72° C. for 10 minutes, and then stored at 4° C. PCR product was purified using QIAquick PCR Purification Kit (QIAGEN, Mississauga, ON), as per manufacturer's instructions.

Heavy chain purified PCR product was cloned into the pCR2.1 vector using the TOPO TA Cloning® Kit (Invitrogen, Burlington, ON). The reaction contained 1 microliter of purified PCR product. 2 microliter of ligation reaction was used to transform One Shot® MAX Efficiency™ DH5α®-T1$^R$ *E. coli* (Invitrogen, Burlington, ON). 30 microliter of transformed cells were plated onto pre-warmed Lennox L broth (LB) agar (Sigma, Oakville, ON) plates containing 50 micrograms/mL ampicillin (Sigma, Oakville, ON) and 40 microliters of 40 mg/mL 5-bromo-4-chloro-3-indolyl-beta-D-galactopyranoside (X-gal, Caledon Laboratories, Georgetown, ON) in N,N-dimethylformamide (Caledon Laboratories, Georgetown, ON). The plates were inverted and incubated at 37° C. overnight.

Ten single clones from H460-16-2 $V_H$ transformed plate were selected and used to inoculate 4 mL of LB broth containing 50 micrograms/mL ampicillin. Cultures were grown overnight at 37° C. shaking at 200 rpm. Plasmids were isolated from each culture using QIAprep Spin Miniprep Kit (QIAGEN, Mississauga, ON), as per manufacturer's instructions.

Recovered plasmids were digested with EcoR I to determine the size of the insert. The H460-16-2 Vh digests contained 5 microliters of plasmid, 0.04 microliters of 50 U/microliter EcoR I (Amersham Biosciences, Baie d'Urfé, QC), 1.5 microliters of 10x buffer H (Amersham Biosciences, Baie d'Urfé, QC), 1.5 microliters of 0.1% BSA (Amersham Biosciences, Baie d'Urfé, QC) and 6.96 microliters of water. The plasmids were digested at 37° C. for 1 hour. 5 microliters of each digested plasmid was run on a 1.0% agarose gel.

Clone #3 and #1 appeared to have the expected 500 bp insert. Ten more clones were selected from the pCR2.1 (H460-16-2 $V_H$)-transformed *E. coli* plate in order to obtain more clones with the correct insert. Clones were used to inoculate LB broth as described above. Plasmids were isolated from cultures as described above, and then digested with EcoR I as described above.

Figure 20:
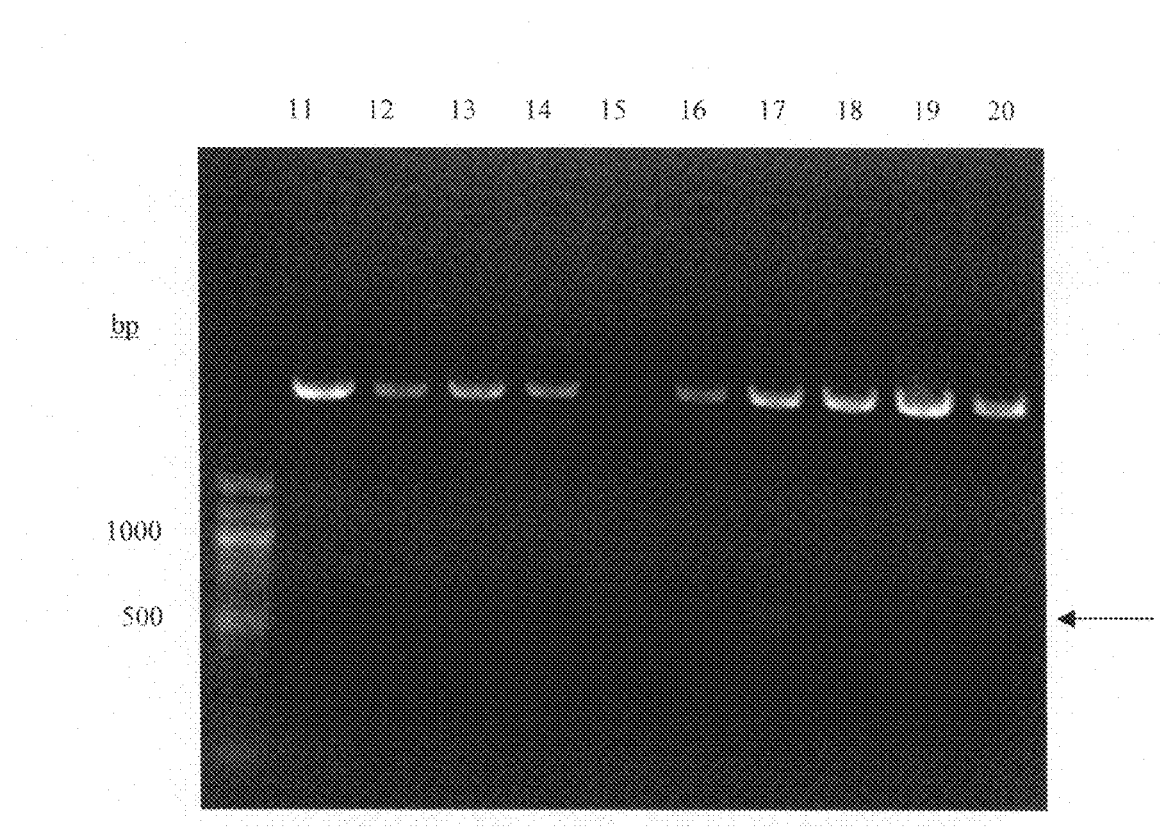
FIG. 20. EcoR I digested plasmids isolated from *E. coli* transformed with pCR2.1(H460-16-2 Vh). The clone number is indicated at the top. The molecular weight marker is indicated on the left. The arrow indicates the position of the desired H460-16-2 Vh inserts.

FIG. 20 shows EcoR I digests of pCR2.1(H460-16-2 Vh) plasmids. The large band around 5000 bp is the pCR2.1 vector backbone. Clone #17 had a band at 500 bp, the expected size of the H460-16-2 $V_H$ insert (indicated by the arrow).

The plasmids that contained appropriately sized inserts (Vh #1, Vh #3 and Vh #17) were sequenced at York University's Core Molecular Biology Facility (Toronto, ON). Sequences are given in FIG. 21 (SEQ ID NOS:9-11). The correct H460-16-2 Vh sequence was found in clone 17. The correct sequence was used for construction of the chimeric H4601-16-2 IgG2 plasmid. Plasmids with the correct sequence were stored at −30° C. for future applications.

2.0 Cloning of Murine H460-16-2 Genes into CMV Promoter Vectors Containing Human Constant Region Genes In order to create murine-human IgG1 chimeric antibody constructs, the murine H460-16-2 variable region genes were cloned into plasmids containing human constant region genes. These CMV promoter vectors were obtained from G. R. McLean et al. The vectors were originally called pHC-huCg1 and pLC-huCk. Herein, they will be referred to as pCH-huIg1 and pCL-huCk.

2.1 Change Restriction Enzyme Site of pCH-huIg1

Figure 22:
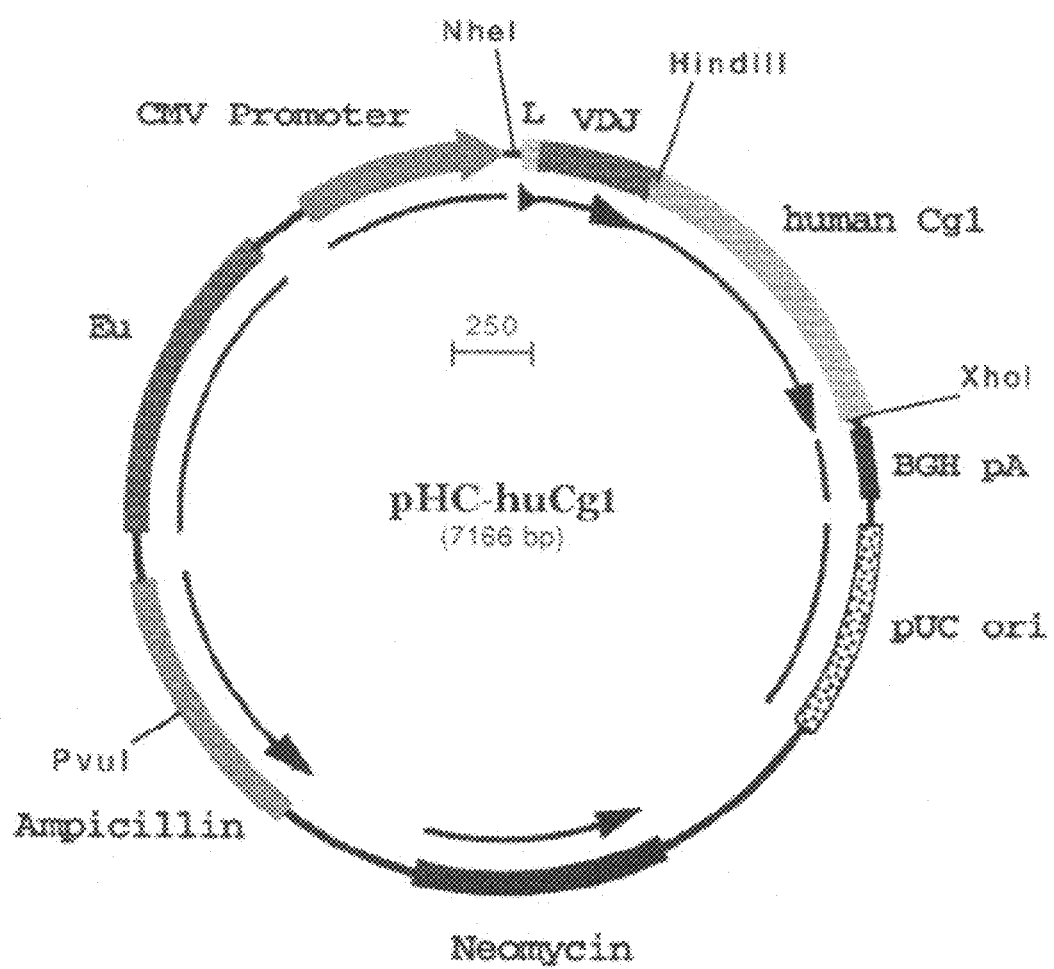
FIG. 22. The schematic plasmid map of the pHC-huCg1 vector (also called pCH-huIg1). The constant region for human Cγ1 lies between the Hind III and Xho I restriction sites. Selection markers for bacteria (Ampicillin) and mammalian cells (Neomycin) are shown. This plasmid was provided by G. R. McLean et al.

The plasmid map for the heavy chain CMV promoter vector (pCH-huIg1) is given in FIG. 22. The H460-16-2 Vh variable gene was cloned between the Nhe I and Hind III restriction sites. Due to an internal Hind III site within the H460-16-2 Vh gene, the Hind III site on the vector was changed to BsiW I.

PCR primers were designed in house to facilitate this cloning, and were synthesized by Gibco BRL (Burlington, ON). Primer sequences are given in FIG. 23 (SEQ ID NOS:12-19). 1 microliter of purified pCH-huIg1 plasmid (G.R. McLean, Bronx, N.Y.) was combined with 1 microliter of 20 pmol/microliter pCH-huBsiWI primer (SEQ ID NO:12), 1 microliter of 20 pmol/microliter BGH primer (SEQ ID NO:13), 0.2 microliters of 50 mM $MgCl_2$ (Invitrogen, Burlington, ON) and 22 microliters of Platinum® PCR Supermix (Invitrogen, Burlington, ON). The reaction was incubated in a thremocycler at 94° C. for 5 minutes, followed by 30 cycles of 94° C. for 1 minute, 58° C. for 1 minute and 72° C. for 1 minute. Finally, the reaction was incubated at 72° C. for 10 minutes, and then stored at 4° C.

Figure 24:
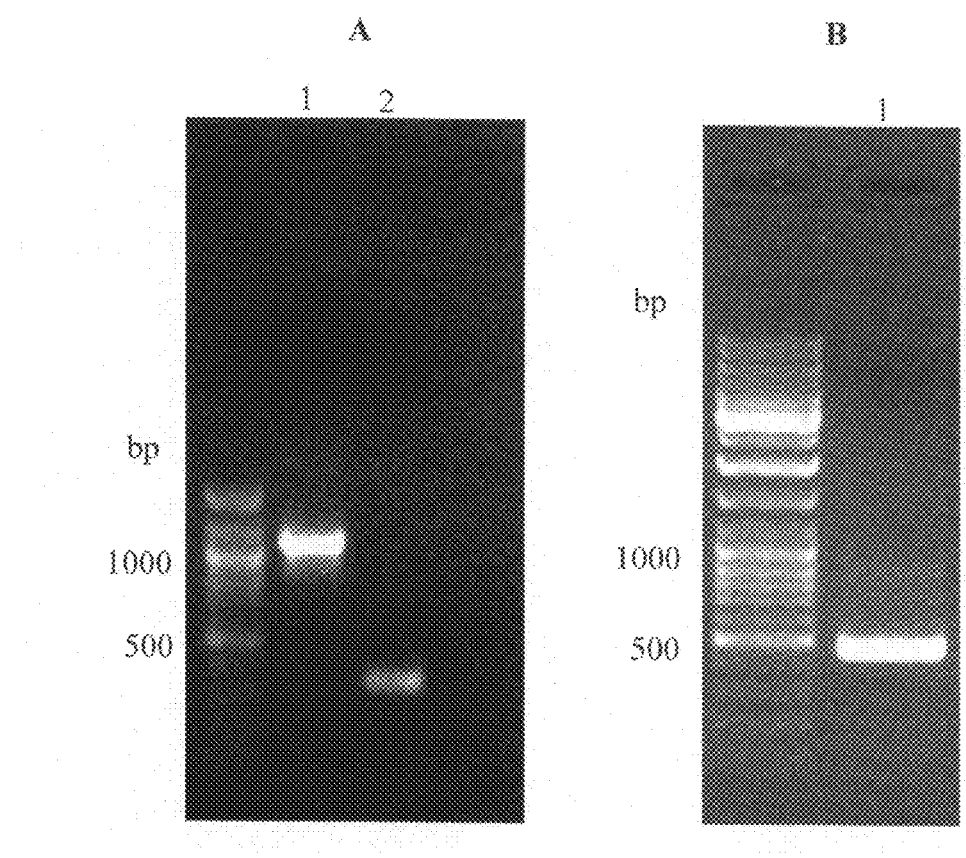
FIG. 24. PCR amplified pCH-huIg1 (Panel A, Lane 1), H460-16-2 Vk (Panel A, Lane 2) and H460-16-2 Vh (Panel B, Lane 1) PCR amplification added the appropriate restriction sites to the existing templates. A BsiW I site was added just downstream of the existing Hind III site of pCH-huIg1 vector. The 1100 bp band (Lane 1) is the amplified region of the plasmid between the Hind III and Xba I sites. An Nhe I site was added at the 5' end and a Not I site was added at the 3' end of the H460-16-2 Vk gene. An Nhe I site was added at the 5' end and a BsiW I site was added at the 3' end of the gene. The resulting sizes of the H460-16-2 Vk (Panel A, Lane 2) and H460-16-2 Vh (Panel B, Lane 1) bands are similar in size to the original genes, ~450 bp, as very few nucleotides were added.

Four microliters of PCR product was run on a 1.0 percent agarose gel, as shown in FIG. 24. Panel A, Lane 1 is the PCR amplified region of the pCH-huIg1 plasmid that contains the human heavy chain constant region of IgG1. A band appears at ~1100 bp, which is the expected size. The remaining PCR product was purified using QIAquick PCR Purification Kit (QIAGEN, Mississauga, ON).

Both the purified PCR product and purified pCH-huIg1 plasmid were digested with Hind III and Xho I to facilitate ligation. The PCR product digestion contained 46 microliters of purified PCR product, 6 microliters of 10× buffer M (Amersham Biosciences, Baie d'Urfé, QC), 6 microliters of 0.1% BSA (Amersham Biosciences, Baie d'Urfé, QC) and 2 microliters of 15 U/microliter Hind III (Amersham Biosciences, Baie d'Urfé, QC). The plasmid digestion contained 4 microliters of 1.4 micrograms/microliter pCH-huIg1, 6 microliters of 10× buffer M (Amersham Biosciences, Baie d'Urfé, QC), 6 microliters of 1 percent BSA (Amersham Biosciences, Baie d'Urfé, QC) 42 microliters of water and 2 microliters of 15 U/microliter Hind III (Amersham Biosciences, Baie d'Urfé, QC). Digestions were incubated at 37° C. for 2 hours. Small aliquots (2 microliters of PCR product reaction and 3 microliters of plasmid reaction) were removed and saved to check progression of digestion on an agarose gel. To the remaining digestions, 3.2 microliters of 1 M NaCl, 2.5 microliters of 1 M Tris-HCl, pH 7.4 and 3 microliters of 8 U/microliter Xho I (New England Biolabs, Ipswich, Mass.) were added. Reactions were further incubated at 37° C. for 2 hours. Another small aliquot of each digestion was removed and saved to run on an agarose gel.

Figure 25:
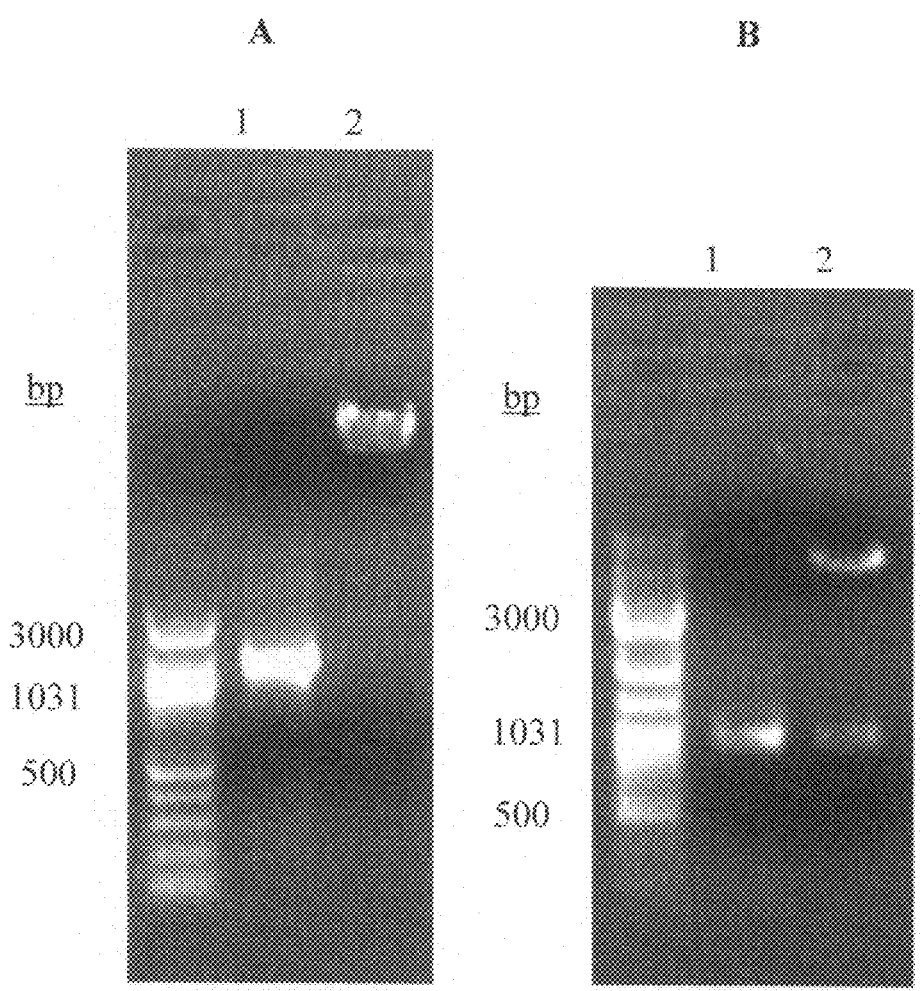
FIG. 25. Digestion of human heavy chain constant region of IgG1 PCR product (Lane 1) and pCH-huIg1 plasmid (Lane 2). Panel A is a single digest using Hind III. Panel B is a double digest using Hind III and Xho I. The size of the PCR product (Lane 1) does not change between digestions (Panels A and B) from ~1000 bp as very few nucleotides are removed by digestion. The pCH-huIg1 plasmid (Lane 2) is completely linearized by Hind III (Panel A). A band equal to the size of the digested PRC product appears from the plasmid double digestion (Lane 2, Panel B) around 1000 bp. This is the portion of the plasmid to be replaced with the PCR product, which contains the new BsiW I site.

FIG. 25 shows the digested PCR product and plasmid. There is very little change in size of the PCR product following digestion (Lane 1, Panels A and B), as is expected due to the very small numbers of base pairs removed from either end. The single Hind III digest of the plasmid (Panel A, Lane 2) shows the size of the linearized plasmid (larger than the molecular weight marker). The double Hind III and Xho I digest (Panel B) shows the large plasmid backbone and the ~1000 bp section that has been digested out and will be replaced with the digested PCR product. The remaining digested PCR product was purified using QIAquick PCR Purification kit (QIAGEN, Mississauga, ON) and the remaining plasmid backbone was purified from a 1% aragose gel using QIAquick Gel Extraction Kit (QIAGEN, Mississauga, ON).

Digested PCR product and plasmid backbone were ligated together in a 4:1 molar ratio. The reaction contained 233 ng of digested plasmid backbone, 162 ng of digested PCR product, 4 microliters of 5× ligation buffer (Gibco BRL, Burlington, ON), 4 microliters of 1 U/microliter T4 DNA ligase (Gibco BRL, Burlington, ON) and 9.33 microliters of water. The reaction was incubated at 16° C. overnight, then at 70° C. for 15 minutes to inactivate the enzyme. 2 microliters of the ligation reaction was transformed into 50 microliters of One Shot® MAX Efficiency® DH5α™-T1$^R$ E. coli cells (Invitrogen, Burlington, ON) by incubating on ice for 30 minutes, at 42° C. for 2 minutes, then again on ice for 5 minutes. 250 microliters of S.O.C. media (Invitrogen, Burlington, ON) was added and transformed cells were incubated at 37° C. for 1 hour. One hundred microliters of cells were plated onto pre-warmed LB agar plates (Sigma, Oakville, ON) containing 50 micrograms/mL ampicillin (Sigma, Oakville, ON) and incubated overnight at 37° C.

Figure 26:
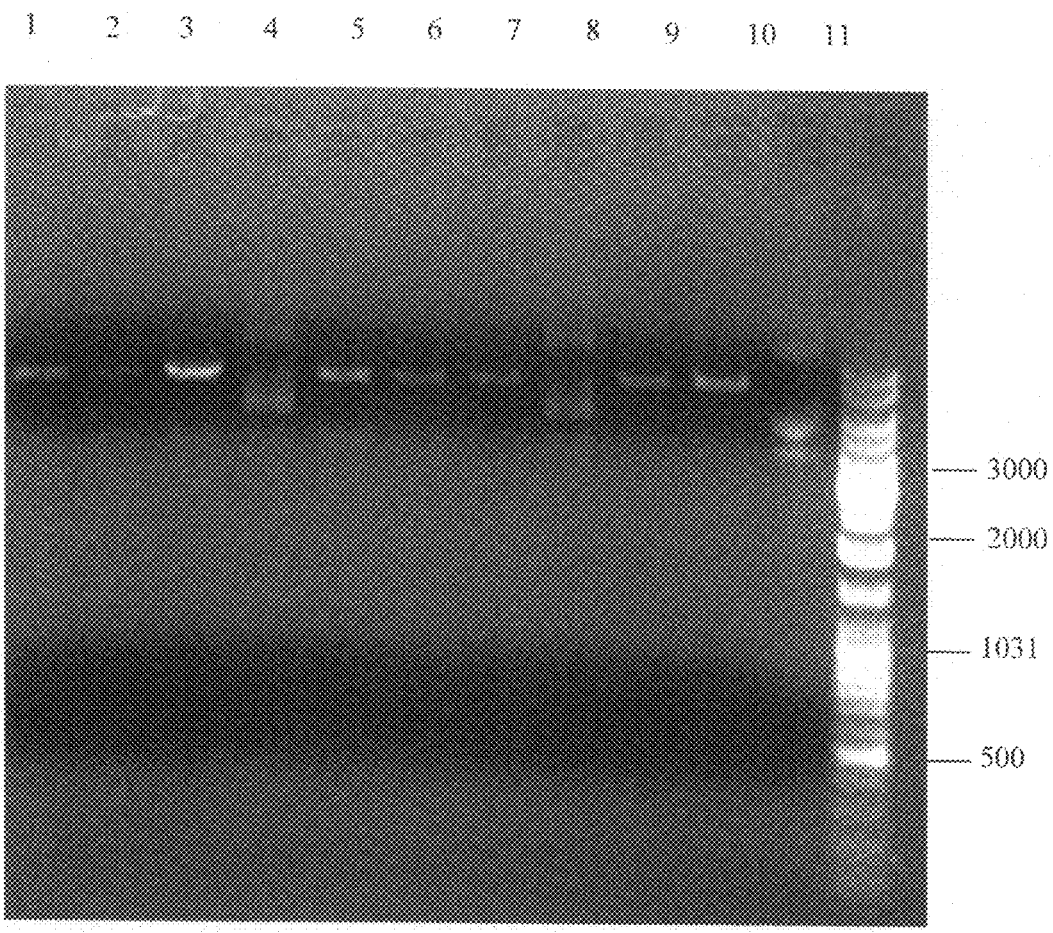
FIG. 26. BsiW I digested pCH-huIg1 with altered cut site. A BsiW I restriction site was added to pCH-huIg1 to facilitate cloning of H460-16-2 (which has an internal Hind III site). Plasmids were isolated from *E. coli* cells transformed with the altered plasmids and digested with BsiW I to determine if the cut site was incorporated. The clone number is indicated above each lane, except in the case of Lane 11, which is an undigested control plasmid (clone #5). All clones except 4 and 8 are linearized upon digestion, which confirms they contain the new cut site. Clones 4 and 8 appear the same as Lane 11, the uncut control, indicating they do not contain the new cut site.

Ten single colonies were selected from the transformed cells and used to inoculate 4 mL of LB broth (Sigma, Oakville, ON) containing 50 μg/mL of ampicillin (Sigma, Oakville, ON), and incubated overnight at 37° C. shaking at 200 rpm. Plasmids were isolated from overnight cultures using QIAprep Miniprep Kit (QIAGEN, Mississauga, ON). Isolated plasmids were digested with BsiW I to identify which clones had incorporated the new cut site. Digests contained 3 microliters of purified plasmid, 2 microliters of 10× NEBuffer 2 (New England Biolabs, Ipswich, Mass.), 1 microliter of 3 U/microliter BsiW I (New England Biolabs, Ipswich, Mass.) and water up to 20 microliters. Digests were incubated at 37° C. for 2 hours, and then 5 microliters of the digested plasmid was run on a 1% agarose gel, as shown in FIG. 26. All clones except 4 and 8 were linearized upon digestion, indicating they incorportaed the new BsiW I cut site. Lane 11 shows an undigested aliquot of clone 5 as a control circular plasmid. Clones 1, 2, 5 and 7 were sequenced at York University (Toronto, ON). All 6 clones had the desired sequence and were stored at −30° C. for future use.

2.2 Insert ARH460-16-2 Vκ and $V_H$ Genes into pCL-huCk and pCH-huIg1

Figure 27:
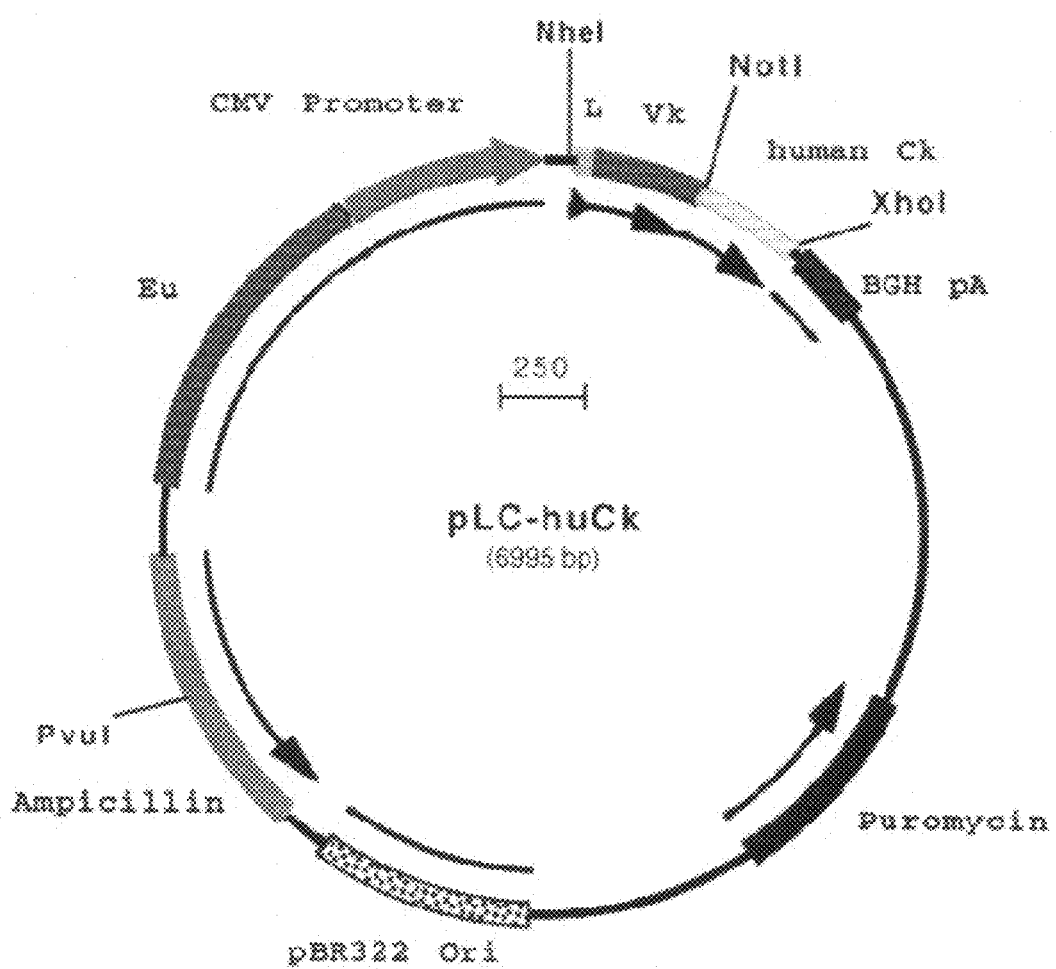
FIG. 27. The schematic plasmid map of the pCL-huCk vector. The constant region for human Ck lies between the Not I and Xho I restriction sites. The variable region lies between the Nhe I and Not I sites. Selection markers for bacteria (Ampicillin) and mammalian cells (Puromycin) are shown. This plasmid was provided by G. R. McLean et al.

In order to facilitate the cloning of the H460-16-2 Vk and Vh genes into pCL-huCk and pCH-huIg1, respectively, restriction sites needed to be added to either end of the genes. For the light chain, a Bgl II site was added at the 5' end and a Hind III site was added to the 3' end. For the heavy chain, a Nhe I site was added at the 5' end and a BsiW I site was added to the 3' end. Sequences for the primers used in these PCR reactions are given in FIG. 23 (SEQ ID NOS:12-19). The plasmid map for pCL-huCk (also called pLC-huCk) is given in FIG. 27. Although it does not appear in the Figure, there is a Bgl II site between the leader and variable regions in the pCL-huCk vector.

For the light chain, 1 microliter of 150 ng/microliter plasmid purified from pCR2.1(H460-16-2 Vk) M #1-1 (SEQ ID NO:1) (see above, M denotes Master Cell Bank) was combined with 1 microliter of 20 pmol/microliter H460-16-2 Vk 5' primer (SEQ ID NO:14), 1 microliter of 20 pmol/microliter Vk 3'NotI (SEQ ID NO:15), 0.2 microliter of 50 mM MgCl$_2$ (Invitrogen, Burlington, ON) and 22 microliters of Platinum® PCR Supermix (Invitrogen, Burlington, ON). For the heavy chain, 1 microliter of 40 ng/microliter plasmid purified from pCR2.1 (H460-16-2 Vh) #1 (SEQ ID NO:6) (see above) was combined with 1 microliter of 25 pmol/microliter H460-16-2 Vh 5' NheI primer (SEQ ID NO:16), 1 microliter of 25 pmol/microliter Vh 3' BsiWI primer (SEQ ID NO:12) and 47 microliters of PCR Supermix High Fidelity (Invitrogen, Burlington, ON). The light chain reaction was incubated at 94° C. for 5 minutes, 30 cycles of 94° C. for 1 minute, 58° C. for 1 minute and 72° C. for 1 minute, followed by 72° C. for 7 minutes. The heavy chain reaction was incubated similarly, but at 55° C. for the annealing temperature (instead of 58° C.).

The restriction sites flanking the Ch-ARH460-16-2 genes in the CMV promoter vectors required alteration to facilitate sub-cloning into CREF1 expression vectors. The leader, variable and constant regions in the CMV promoter constructs were PCR amplified using primers that introduced the desired restriction sites. Primer sequences are given in FIG. 23 (SEQ ID NOS:12-19).

Figure 28:
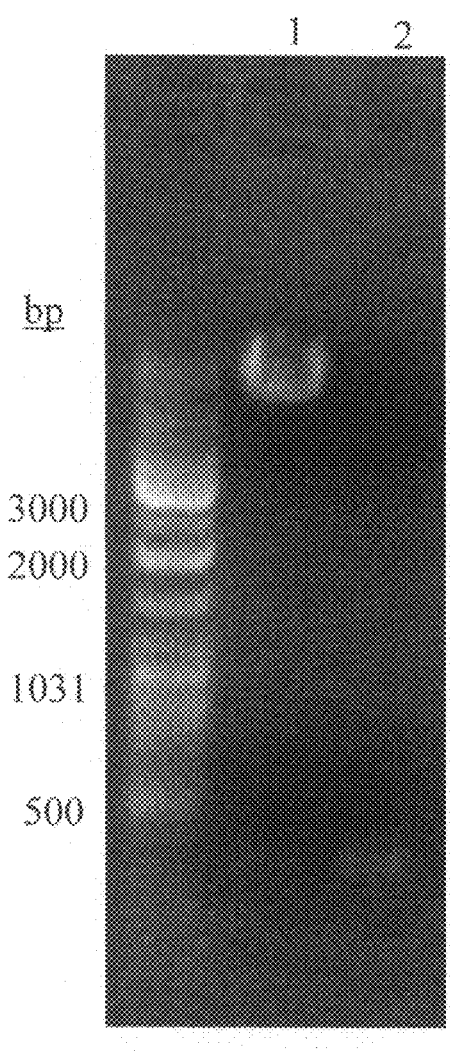
FIG. 28. pCL-huCk and H460-16-2 Vk digested with Bgl II and Not I. Both pCL-huCk plasmid (Lane 1) and H460-16-2 Vk PCR product (Lane 2) were digested with Bgl II and Not I to facilitate cloning. The digested plasmid (Lane 1) appears as a large band, which is the plasmid backbone, and a ~400 bp band, which is the light chain variable region to be replaced with H460-16-2 Vk. The H460-16-2 Vk PCR product (Lane 2) also appears as ~400 bp, the anticipated size of the light chain variable region.

For the light chain, both pCL-huCk and H460-16-2 Vk PCR product were digested with Bgl II and Not I to facilitate cloning. 40 microliters of H460-16-2 Vk PCR product was combined with 6 microliters of 10× NEBuffer 3 (New England Biolabs, Ipswich, Mass.), 0.6 microliters of 100× BSA (New England Biolabs, Ipswich, Mass.), 2 microliters of 10 U/microliter Bgl II (New England Biolabs, Ipswich, Mass.), 2 microliters of 10 U/microliter Not I and water up to 60 microliters. For the light chain plasmid, an equivalent reaction containing 8 microliters of pCL-huCk (G.R. McLean, Bronx, N.Y.) instead of PCR product was prepared. Both reactions were incubated at 37° C. for 3 hours. An aliquot of digested vector and insert was run on a 1.2% agarose gel, as shown in FIG. 28. The linearized pCL-huCk vector backbone (lane 1) appears as the large band, whereas the removed light chain variable region from the vector appears as the 400 bp band. The digested H460-16-2 Vk (lane 2) gene also appears at 400 bp. The remaining linearized pCL-huCk plasmid was run on a 1.0 percent gel and purified using QIAquick Gel Extraction Kit (QIAGEN, Mississauga, ON). The remaining digested H460-16-2 Vk PCR product was purified using QIAquick PCR Purification Kit (QIAGEN, Mississauga, ON).

For the heavy chain, both pCH-huIg1 plasmid with the added BsiW I site (see above) and H460-16-2 Vh PCR product were digested with BsiW I and Nhe I to facilitate cloning. The plasmid reaction contained 0.7 microliters of pCH-huIg1 (BsiW I) #1 DNA, 2 microliters of 10× NEBuffer 2 (New England Biolabs, Ipswich, Mass.), 0.4 microliters of 10 U/microliters BsiW I (New England Biolabs, Ipswich, Mass.) and water up to 20 microliters. An equivalent reaction containing 12.1 microliters H460-16-2 Vh purified PCR product instead of plasmid was also setup. Reactions were incubated at 55° C. overnight, and then a 5 microliter aliquot was removed from the plasmid digestion to check on a gel. 0.2 microliters of 100× BSA (New England Biolabs, Ipswich, Mass.) and 1 microliter of 5 U/microliter Nhe I (New England Biolabs, Ipswich, Mass.) was added to both reactions and they were further incubated at 37° C. for overnight. Another 5 microliters was removed and used to run on a gel to check digestion.

Figure 29:
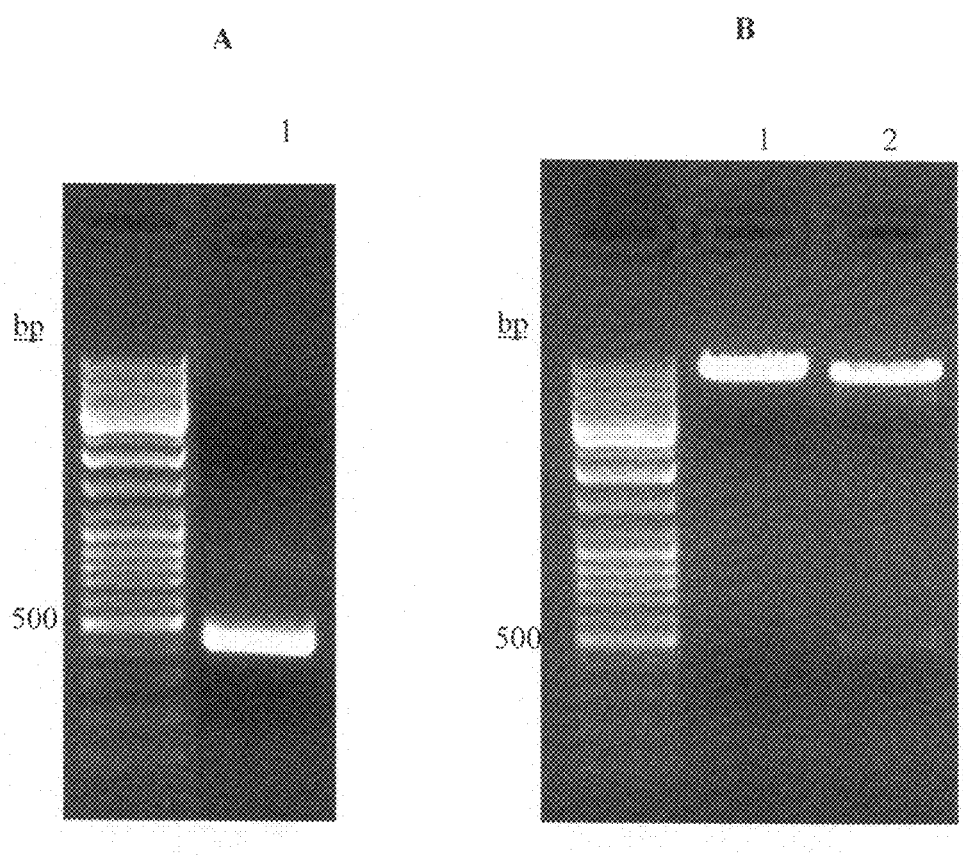
FIG. 29. H460-16-2 Vh and pCH-huIg1 digested with BsiW I and Nhe I. Panel A shows the H460-16-2 Vh PCR product digested with BsiW I and Nhe I at 450 bp. Panel B shows pCH-huIg1 digested with BsiW I (Lane 1) and BsiW I and Nhe I (Lane 2). The single pCH-huIg1 digest (Panel B, Lane 1) appears as large band, and as a large band with a 450 bp insert in the double digest (Panel B, Lane 2), which correspond to the heavy chain variable region to be replaced with H460-16-2 Vh.

FIG. 29 shows the results of the digestion run on 1.2 percent gels. The single BsiW I digest (Panel B, Lane 1) shows the linearlized plasmid. The double BsiW I and Nhe I digest (Panel B, Lane 2) shows the plasmid backbone as the large band and the heavy chain variable region at 450 bp. This smaller band is to be replaced with 450 bp digested H460-16-2 Vh PCR product (Panel A, Lane 1). The remaining digested plasmid was run on a 1.2 percent gel and purified using QIAquick Gel Extraction Kit (QIAGEN, Mississauga, ON). The remaining digested H460-16-2 Vh PCR product was purified using QIAquick PCR Purification Kit (QIAGEN, Mississauga, ON).

The digested H460-16-2 Vk PCR product was ligated into the linearized pCL-huCk plasmid. 220 ng of digested pCL-huCk was combined with 66 ng of digested H460-16-2 Vk, 4 microliters of 5× ligase buffer (Gibco BRL, Burlington, ON), 4 microliters of 1 U/microliter T4 DNA ligase (Gibco BRL, Burlington, ON) and water up to 20 microliters. The reaction was incubated overnight at 16° C., then incubated at 70° C. for 10 minutes to heat inactivate enzyme. Two microliters of the ligation reaction was transformed into 50 microliters of One Shot® MAX Efficiency® DH5α™-T1$^R$ *E. coli* cells (Invitrogen, Burlington, ON) by incubating on ice for 30 minutes, at 42° C. for 2 minutes, and on ice again for 5 minutes. 250 microliters of S.O.C. media (Invitrogen, Burlington, ON) was added and transformed cells were incubated at 37° C. for 1 hour. Thirty microliters of cells were plated onto pre-warmed LB agar (Sigma, Oakville, ON) plates containing 50 micrograms/mL ampicillin (Sigma, Oakville, ON) and incubated overnight at 37° C.

The heavy chain ligation reaction was setup containing 250 ng of digested pCH-huIg1, 84 ng digested H460-16-2 Vh PCR product, 4 microliters of 5× ligase buffer (Gibco BRL, Burlington, ON), 1 microliter of 1 U/microliter T4 DNA ligase (Gibco BRL, Burlington, ON) and water up to 20 microliters. The reaction was incubated overnight at 16° C., and then at 65° C. for 10 minutes to heat inactivate the enzyme. 1 microliter of ligation reaction was transformed into 25 microliters of One Shot® MAX Efficiency® DH5α™-T1$^R$ *E. coli* cells (Invitrogen, Burlington, ON) by incubating on ice for 30 minutes, at 42° C. for 2 minutes, and on ice again for 5 minutes. 250 microliters of S.O.C. media (Invitrogen, Burlington, ON) was added and transformed cells were incubated at 37° C. for 1 hour. 30 microliters of cells were plated onto pre-warmed LB agar (Sigma, Oakville, ON) plates containing 50 microlgrams/mL ampicillin (Sigma, Oakville, ON) and incubated overnight at 37° C.

Eight single colonies from the transformed pCL-huCk (H460-16-2 Vk) plate and six single colonies from the transformed pCH-huIg1 (H460-16-2 Vh) plate were selected and used to inoculate 4 mL 2-YT broth (Gibco BRL, Burlington, ON) containing 50 micrograms/mL ampicillin (Sigma, Oakville, ON). Plasmids were isolated from overnight cultures using QIAprep Miniprep Kit (QIAGEN, Mississauga, ON) and digested to ensure the correct sized insert. Light chain reactions were prepared with 3 microliters plasmid, 1.5 microliters 10× NEBuffer 3 (New England Biolabs, Ipswich, Mass.), 0.15 microliters 100× BSA (New England Biolabs, Ipswich, Mass.), 2 microliters of 10 U/microliter Bgl II, 2 microliters of 10 U/microliter Not I and 9.65 microliters water, and incubated at 37° C. for 3 hours. Heavy chain reactions were setup by combining 2 microliters of plasmid with 2 microliters of 10× NEBuffer 2 (New England Biolabs, Ipswich, Mass.), 0.4 microliters of 10 U/microliter BsiW I (New England Biolabs, Ipswich, Mass.) and water up to 20 microliters. These were incubated at 55° C. for 2 hours, and then 2 microliters of 10× BSA (New England Biolabs, Ipswich, Mass.) and 0.8 microliters of 5 U/microliter Nhe I was added. Reactions were further incubated at 37° C. for 2 hours.

Figure 30:
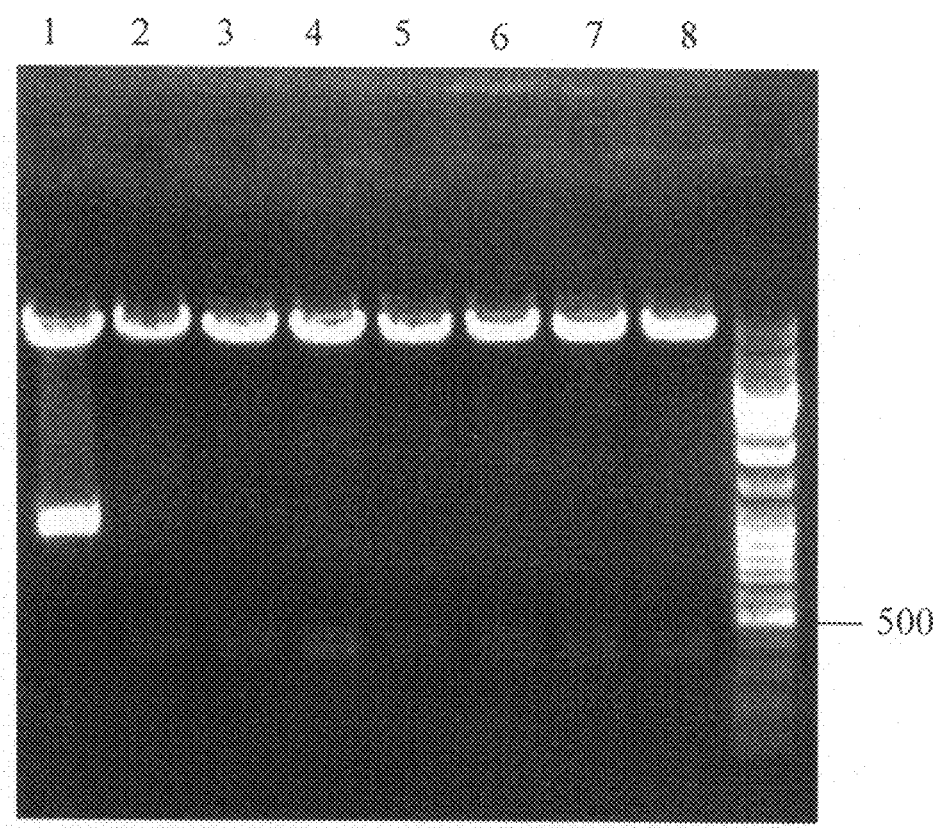
FIG. 30. Plasmids isolated from pCL-huCk (H460-16-2 Vk) transformed *E. coli* digested with Bgl II and Not I run on a 1% agarose gel. The number above the lane indicates the clone number. All clones except #1 demonstrate the desired ~400 bp insert which corresponds to the H460-16-2 Vk gene.
Figure 31:
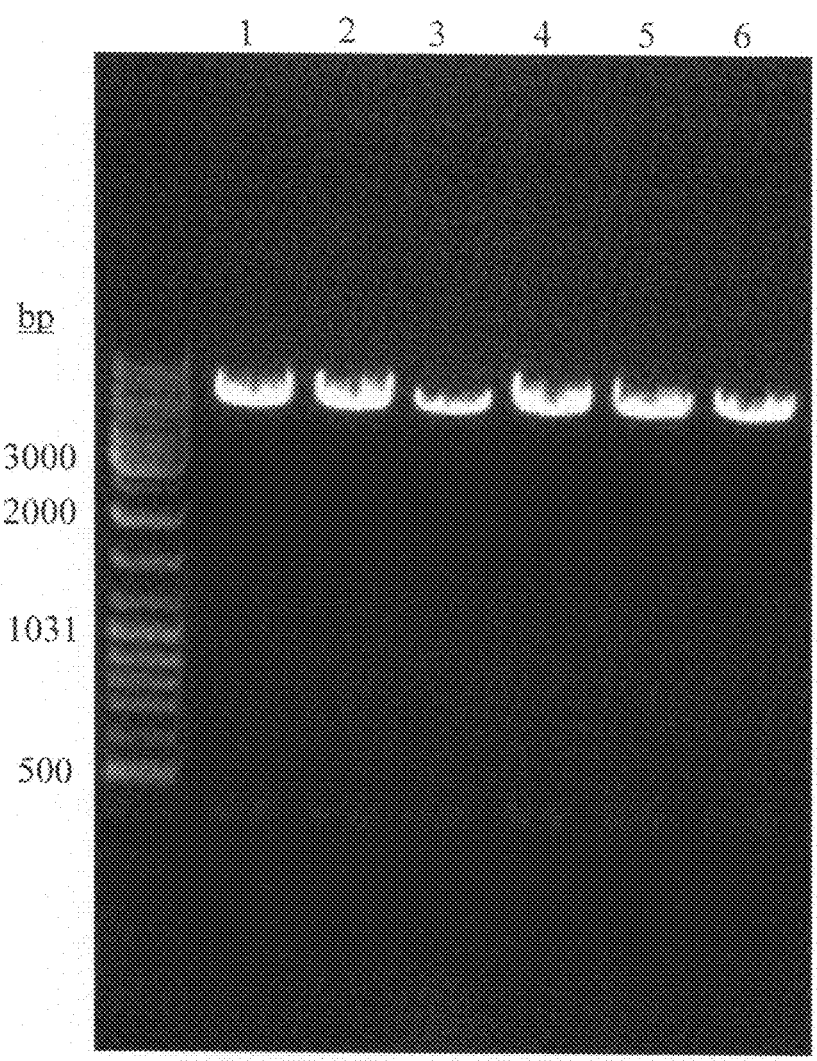
FIG. 31. Plasmids isolated from *E. coli* transformed with pCH-huIg1 (H460-16-2 Vh) digested with BsiW I and Nhe I run on a 1.2 percent agarose gel. The number above the lane indicates the clone number. All clones have the desired 450 bp insert, which corresponds to the H460-16-2 Vh gene.

FIGS. 30 and 31 show the results of the above digestions of pCL-huCk (H460-16-2 Vk) and pCH-huIg1 (H460-16-2 Vh), respectively. All of the light chain clones (FIG. 30) except #1 contained the desired 400 bp insert that corresponds to the H460-16-2 Vk gene. All the heavy chain clones (FIG. 31) contained the desired 450 bp insert that corresponds to the H460-16-2 Vh gene. Based on these results, pCL-huCk (H460-16-2 Vk) clones 3, 4, 6, 7 and 8, and pCH-huIg1 (H460-16-2 Vh) clones 4 and 6 were sequenced at York University (Toronto, ON). All of the clones sequenced have the desired sequence, and plasmids were stored at −80° C. for further use.

Figure 32:
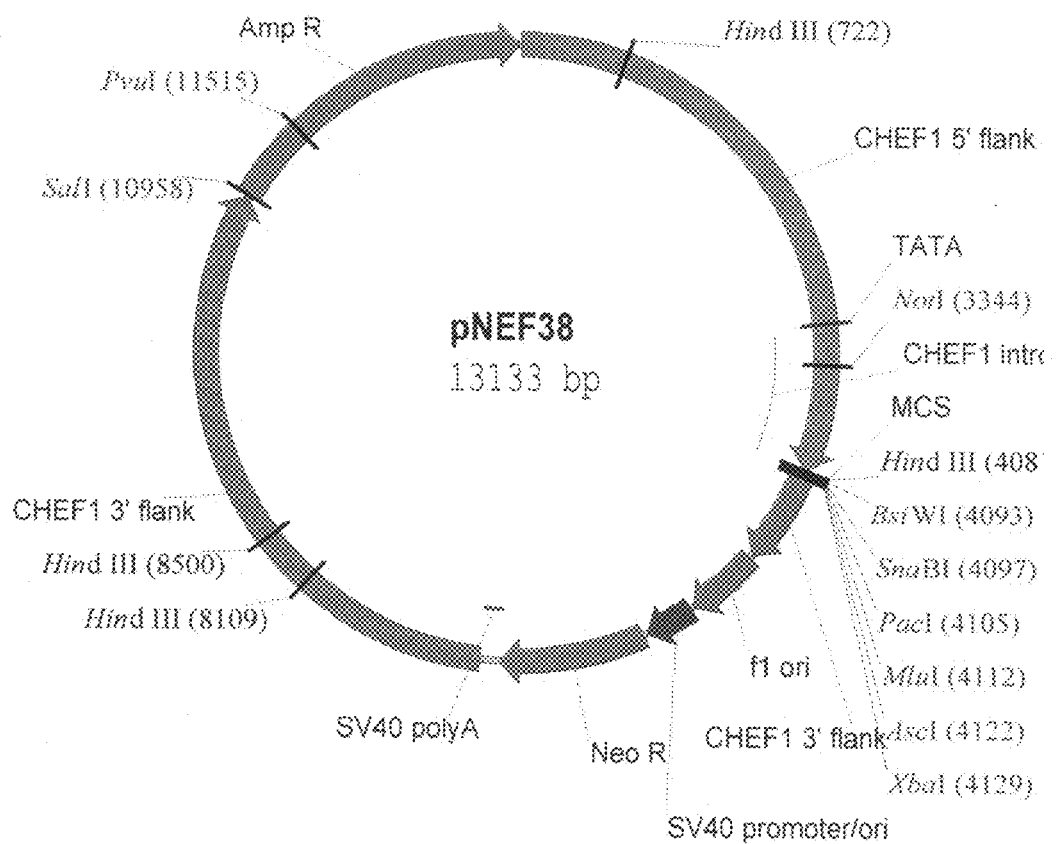
FIG. 32. Plasmid schematic of pNEF38 expression vector (ICOS, Seattle, Wash.). The chimeric H460-16-2 Vk genes were cloned into the multiple cloning site (MCS) using the Mlu I and Xba I restriction sites. The selection marker for this plasmid is the neomycin resistance (Neo$^R$) gene, which provides transfected cells with the ability to grow in the presence of Geneticin® (G418 sulfate).
Figure 33:
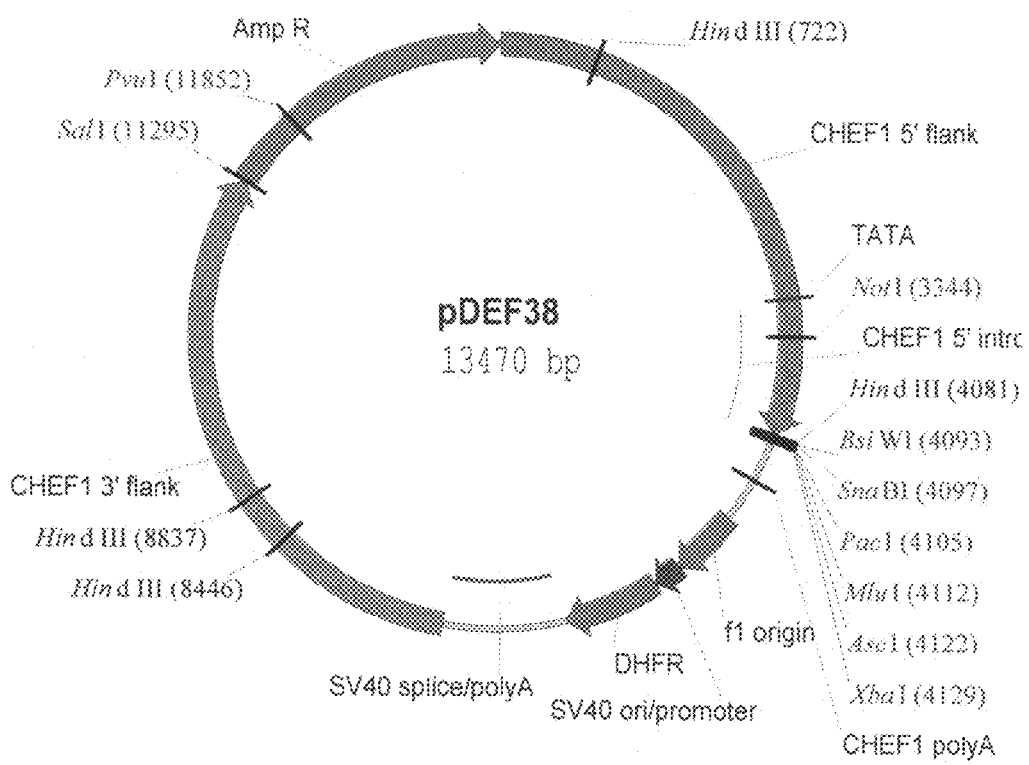
FIG. 33. Plasmid schematic of pDEF38 expression vector (ICOS, Seattle, Wash.). The chimeric H460-16-2 Vh genes were cloned into the multiple cloning site (MCS) using the Mlu I and Xba I restriction sites. The selection marker for this plasmid is the dihydrofolate reductase (DHFR) gene, which provides transfected DHFR deficient cells with the ability to grow in the absence of thymidine and hypoxanthine.

3.0 Cloning Chimerized Light and Heavy Chain ARH460-16-2 into CHEF1 Expression Vectors The murine variable and human constant regions of the light chain (H460-16-2 Vk) were then cloned into the CHEF1 expression vector pNEF38, and the murine variable and human constant regions of the heavy chain (H460-16-2 Vh) were cloned into the CHEF1 expression vector pDEF38. Plasmid maps are given in FIGS. 32 and 33.

For the remainder of this report, the term Ch-ARH460-16-2 Vk refers to the combination of the light chain variable H460-16-2 gene and the human light chain constant region derived from the pCL-huCk plasmid. The term Ch-ARH460-16-2 Vh refers to the combination of the heavy chain variable H460-16-2 gene and the human heavy chain IgG1 region derived from the pCH-huIg1 plasmid.

3.1 Changing Restriction Sites to Clone into CHEF1 Vectors

The restriction sites flanking the Ch-ARH460-16-2 genes in the CMV promoter vectors required alteration to facilitate sub-cloning into CHEF1 expression vectors. The leader, variable and constant regions in the CMV promoter constructs were PCR amplified using primers that introduced the desired restriction sites. Primer sequences are given in FIG. 23.

Figure 34:
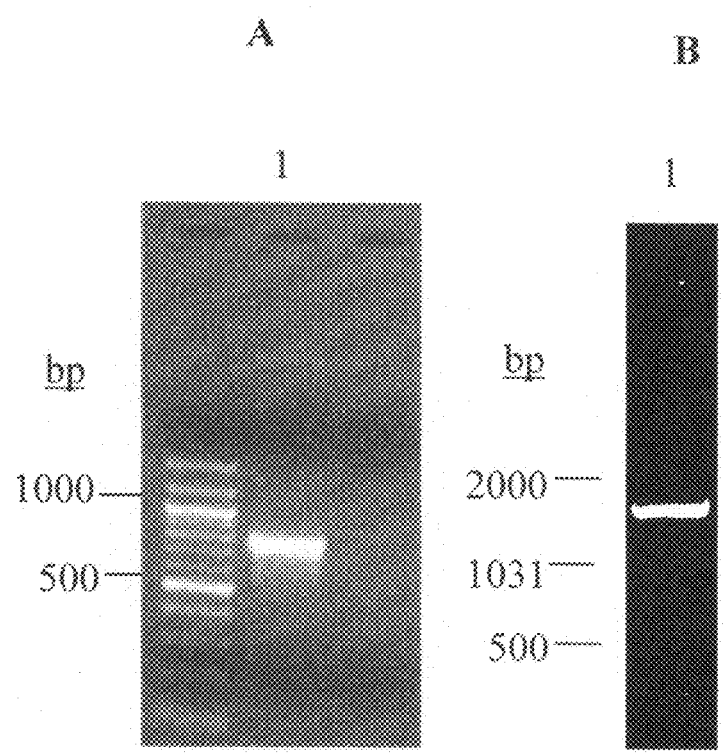
FIG. 34. Chimeric H460-16-2 Vk (Panel A) and $V_H$ (Panel B) PCR products to change restriction sites run on 1.2 percent and 1:0 percent agarose gels, respectively. The chimeric light chain PCR reaction (Panel A, Lane 1) yielded a single band at ~800 bp, which corresponds to the expected size of the combined light variable (420 bp) and constant (320 bp) regions. The heavy chain PCR reaction (Panel B) yielded a single ~1500 bp band, which corresponds to the expected size of both the heavy variable (450 bp) and constant (990 bp) regions.

For the light chain, a PCR reaction was prepared using 1.4 microliters of 73 ng/microliter pCL-huCk (ARH460-16-2 Vk) #3 DNA (see above), 1.0 microliter of 25 pmol/microliter pCL-huCK 5' MluI primer, 1.7 microliters of 15 pmol/microliter BGH primer and 20.9 microltiers PCR Supermix High Fidelity (Invitrogen, Burlington, ON). For the heavy chain, a PCR reaction was prepared using 0.5 microltiers of 0.27 micrograms/microliter pCH-huIg1 (ARH460-16-2 Vh) #4 DNA (see above), 1.7 microliters of 15 pmol/microliter Vh 5' NheI/MluI primer, 1.7 microliters of 15 pmol/microliter BGH primer and 21.1 microliters PCR Supermix High Fidelity (Invitrogen, Burlington, ON). Heavy and light chain reactions were incubated at 94° C. for 2 minutes, followed by 25 or 30 cycles of 94° C. for 30 seconds, 55° C. for 30 seconds and 68° C. for 2 minutes, respectively. An aliquot of each reaction was run on an agarose gel, as shown in FIG. 34. The Ch-ARH460-16-2 Vk PCR product (Panel A, Lane 1) appears as a 800 bp band, the expected size of the light chain murine H460-16-2 Vk variable and human constant regions. The Ch-ARH460-16-2 Vh PCR product (Panel B, Lane 1) appears a band at 1500 bp, which is the expected size of the heavy chain murine H460-16-2 Vh variable and human constant regions.

3.2 Cloning Chimeric H460-16-2 Genes into CHEF1 Vectors

Remaining PCR product was purified using MinElute PCR Purification Kit (QIAGEN, Mississauga, ON) then digested along with CHEF1 vectors with the appropriate restriction enzymes for cloning. Reactions contained 1 micrograms of DNA (purified Ch-ARH460-16-2 Vk PCR product, purified Ch-ARH460-16-2 Vh PCR product, pNEF38 (ICOS, Seattle, Wash.) or pDEF38 (ICOS, Seattle, Wash.)), 2 microliters of 10× NEBuffer 2 (New England Biolabs, Ipswich, Mass.), 2 microliters of 10× BSA (New England Biolabs, Ipswich, Mass.), 0.2 microliters of 20 U/microliter Xba I (New England Biolabs, Ipswich, Mass.) and water up to 20 microliters. Reactions were incubated overnight at 37° C., and then 0.8 microltiers of 1 M Tris-HCl, pH 7.4, 1.0 microltier of 1 M NaCl and 0.4 microltiers of 10 U/microliter Mlu I (New England Biolabs, Ipswich, Mass.) was added and further incubated at 37° C. for 6 hours. The digested PCR products were purified using MinElute Reaction Cleanup Kit (QIAGEN, Mississauga, ON) and the digested vectors were purified with QIAEX II Reaction Cleanup Kit (QIAGEN, Mississauga, ON).

Ch-ARH460-16-2 Vk was ligated into pNEF38 in a 5:1 molar ratio. 25 ng of digested pNEF38 was combined with 69 ng of digested Ch-ARH460-16-2 Vk PCR product, 4 microliters of 5× ligase reaction buffer (Invitrogen, Burlington, ON), 0.5 microliters of 1 U/microliter T4 DNA ligase (Invitrogen, Burlington, ON) and water up to 20 microliters. An equivalent heavy chain reaction was prepared using 25 ng of digested pDEF38 and 66 ng of digested Ch-ARH460-16-2 Vh PCR product. Reactions were incubated overnight at 16° C., then incubated at 65° C. for 10 minutes to inactivate the enzyme. The heavy chain ligation reaction was purified using QIAEX II Reaction Cleanup Kit (QIAGEN, Mississauga, ON).

Ligation reactions were transformed into *E. coli* by adding 3 microliters of diluted salt solution (Invitrogen, Burlington, ON) and 2 microliters of ligation reaction to 50 microliters of One Shot® TOP 10 Electrocomp™ *E. coli* (Invitrogen, Mississauga, ON). The cells were transferred to pre-chilled 1 mm cuvettes and charged in an electroporator for 5 milliseconds at 1700 V. 1 mL of S.O.C. media (Invitrogen, Burlington, ON) was added immediately, and then cells were incubated at 37° C. for 1 hour, shaking at 200 rpm. 200 microliter aliquots of cells were plated onto pre-warmed LB agar plates containing 50 micrograms/mL of ampicillin and incubated overnight at 37° C.

Six single colonies were selected from each plate and used to inoculate 4 mL of 2YT broth (Invitrogen, Burlington, ON) containing 50 micrograms/mL of ampicillin (Sigma Oakville, ON), and incubated overnight at 37° C., shaking at 200 rpm. Plasmids were isolated from the resulting overnight cultures using QIAprep Miniprep Kit (QIAGEN, Mississauga, ON). Light chain plasmids were digested with Xba I and Mlu I to identify which clones contained the correct sized insert. Digestions contained 1 microgram of plasmid DNA, 2 microliters of 10× NEBuffer 2 (New England Biolabs, Ipswich, Mass.), 2 microliters of 10× BSA (New England Biolabs, Ipswich, Mass.), 0.2 microliters of 20 U/microliter Xba I (New England Biolabs, Ipswich, Mass.) and water up to 20 microliters. Reactions were incubated overnight at 37° C., and then 0.8 microliters of 1 M Tris-HCl, pH 7.4, 1.0 microliter of 1 M NaCl and 0.4 microliters of 10 U/microliter Mlu I (New England Biolabs, Ipswich, Mass.) was added and further incubated at 37° C. for 6 hours. Heavy chain plasmids were digested with Xba I, Mlu I and Hind III. 100 ng of plasmid DNA was combined with 2 microliters of 10× NEBuffer 2 (New England Biolabs, Ipswich, Mass.), 2 microliters of 10× BSA (New England Biolabs, Ipswich, Mass.), 0.2 microliters of 20 U/μL Xba I (New England Biolabs, Ipswich, Mass.) and water up to 20 microliters. Reactions were incubated overnight at 37° C., then 0.8 microliters of 1 M Tris-HCl, pH 7.4, 1 microliter of 1 M NaCl and 0.4 microliters of 10 U/μL Mlu I were added and further digested at 37° C. for 6 hours. A small aliquot of digestion was removed to run on a gel, and 2 microliters of 10× NEBuffer 2 (New England Biolabs, Ipswich, Mass.), 0.3 microliters of 15 U/microliter Hind III and 7.7 microliters of water was added. Reactions were incubated at 37° C. for 6 hours.

Figure 35:
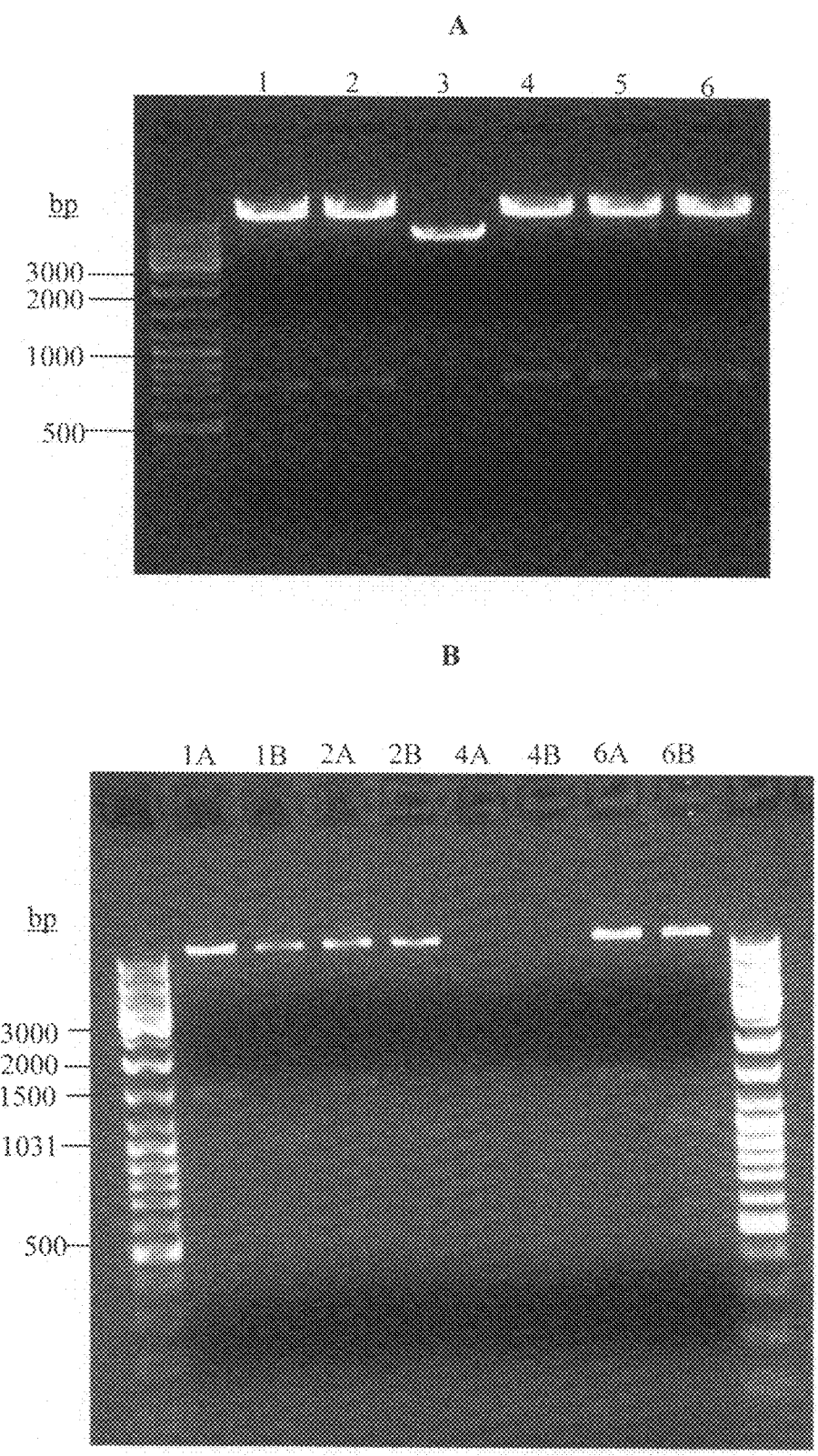
FIG. 35. Plasmids isolated from pNEF38 (H460-16-2 Vk) (Panel A) and pDEF38 (H460-16-2 Vh) (Panel B) transformed *E. coli* digested with Xba I and Mul I. The heavy chain plasmids (Panel B) were also triple digested with Xba I, Mul I and BsiW I (Lanes 1B, 2B, 4B and 6B). For the light chain plasmids (Panel A) all clones except #3 have the desired 750 bp insert, which corresponds to the light chain variable and constant regions. For the heavy chain plasmids, the Xba I and Mlu I digests (Panel B. Lanes 1A, 2A and 6A) show 1500 bp inserts, which correspond to the heavy chain variable and constant regions. The heavy chain plasmids digested with Xba I, MUl I and BsiW I (Panel B, Lanes 1B, 2B and 6B) show bands at 1000 bp and 500 bp, which correspond to the heavy chain constant and variable regions, respectively. Clone 4 (Panel B) did not appear at all, indicating there was a problem with the reaction setup.

Digested plasmids were run on 1.2 percent agarose gels, as seen in FIG. 35. For the light chain plasmids (Panel A) all clones except for #3 had the desired 750 bp insert, which corresponds to the light chain variable and constant regions. For the heavy chain plasmids, the Xba I and Mlu I digests (Panel B, Lanes 1A, 2A and 6A) show 1500 bp inserts, which correspond to the heavy chain variable and constant regions. The heavy chain plasmids digested with Xba I, Mul I and BsiW I (Panel B, Lanes 1B, 2B and 6B) show bands at 1000 bp and 500 bp, which correspond to the heavy chain constant and variable regions, respectively. Clone 4 (Panel B) did not appear at all, indicating there was a problem with the reaction setup.

Based on these results, light chain clones 1, 2 and 4 and heavy chain clones 1, 2 and 6 were sequenced at York University (Toronto, ON). Sequences are given in FIG. 36 (SEQ ID NOS:20-25). The light chain clone pNEF38 (Ch-ARH460-16-2 Vk) #4 and the heavy chain clone pDEF38 (Ch-ARH460-16-2 Vh) #2 have the correct sequences, and were used to construct the chimeric H460-16-2 constructs.

4.0 Initial Cloning to Produce (ch)ARH460-16-2-IgG1

4.1 Construction of pMPGCR5IgG1-Vk+hH460

Figure 37:
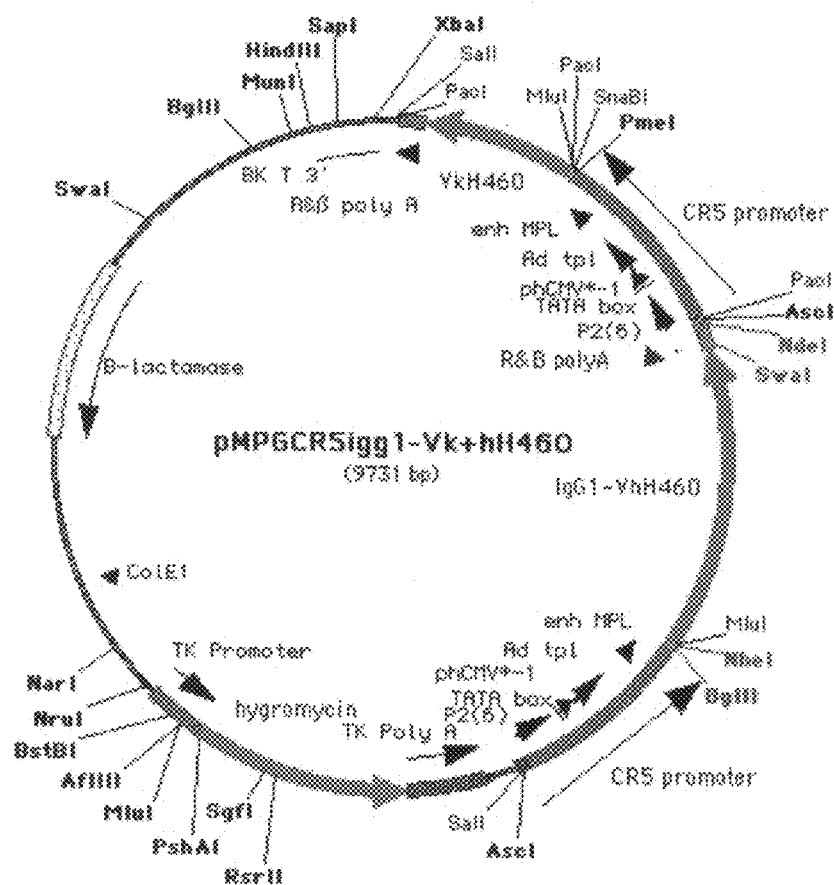
FIG. 37. Map of pMPGCR5IgG1-Vk+hH460. R&B poly A: Rabbit β-globin poly adenylation signal; phCMV: Cytomegalovirus promoter; Ad Tp1: adenovirus tripartite leader; P2 (6): binding domain for the cumate transactivator (cTA); IgG1-VhH460: coding sequence for the heavy chain of H460-16-2; VkH460: coding sequence for the light chain of H460-16-2. BK T 3': Portion of the large T antigen of BK virus; TK: Thymidine kinase; enh MPL: enhancer of the adenovirus major late promoter.

This plasmid contains the heavy and light chain of the chimeric IgG1 isotype of H460-16-2 (Ch-ARH460-16-2 Vh and Ch-ARH460-16-2 Vk) regulated by the cumate inducible promoter (CR5). In addition, this plasmid contains the resistance for hygromycin for selection of stable clones (FIG. 37). This plasmid was produced by first constructing two intermediates plasmids described below.

A) Construction of pMPGCR5VkH460AscId

Figure 38:
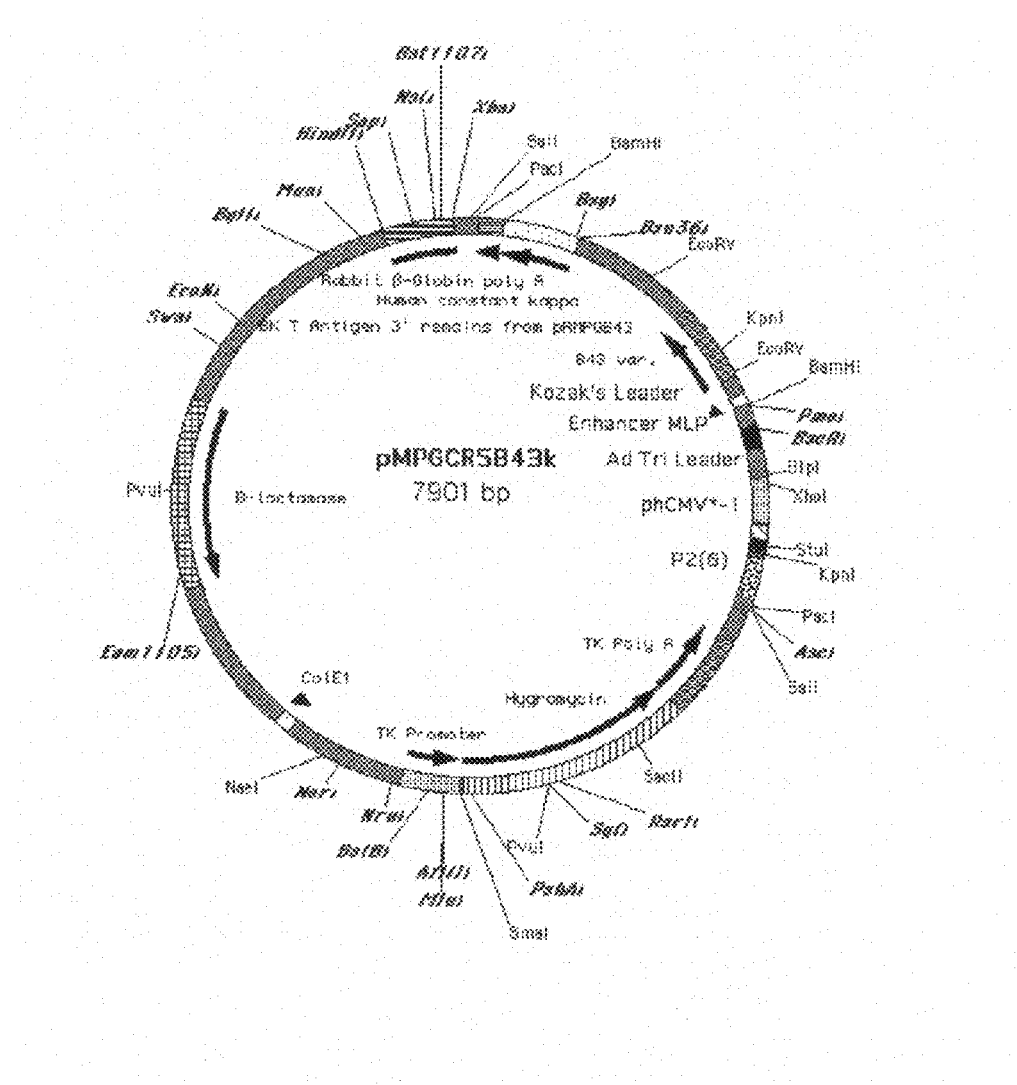
FIG. 38. Map of pMPGCR5B43k.

The DNA fragment coding for the light chain of antibody B43 was removed from pMPGCR5B43k (FIG. 38) by digestion with BamHI. After blunting the ends and treatment with calf intestinal phosphatase (CIP), the vector DNA was ligated with a DNA fragment encoding the light chain obtained by digesting pNEF38 (Ch-ARH460-16-2 Vκ) #4 with XbaI and BsiWI followed by treatment with T4 DNA polymerase to blunt the ends.

B) Construction of pCRSIgG1VhH460AscI.

The DNA fragment coding for the heavy chain of B43 was removed from pKCR5B43G3 (FIG. 39) by digestion with HindIII. After blunting the ends with T4 DNA polymerase and treatment with CIP, the vector DNA was ligated with a DNA fragment encoding the heavy chain isolated by digesting pDEF38 (Ch-ARH460-16-2 $V_H$) #2 with XbaI and PacI. Before ligation, the DNA fragment was blunted with T4 DNA polymerase.

C) Final Assembly

The heavy chain expression cassette (promoter, coding sequence, poly A signal) was excised from pCR5IgG1VhH460AscI by digestion with AscI and inserted into the AscI site of pMPGCR5VkH460AscId which was dephosphorilated by treatment with CIP before ligation. A map of the resulting construct (pMPGCR5IgG1-Vk+hH460) is presented in FIG. 37.

5.0 Production of Clones Expressing Chimeric H460-16-12

A vial of CHO-SF(a) was obtained from Gibco BRL (Burlington, ON) and thawed in CD-CHO medium (Gibco BRL, Burlington, ON) supplemented with 4 mM L-glutamine in May 2000. The cells were grown for 10 days in CD-CHO medium supplemented with 4 mM L-glutamine and frozen stocks were made in 90% fetal bovine serum (Hyclone, Logan, Utah) and 10% DMSO. The CHOcTA cells stably expressing the cumate transactivator (cTA) were generated by transfecting the CHO-SF(a) cells with linearized pMPG-BFP/CMV-cTA/tk-neo using Lipofectamine 2000 (Invitrogen, Burlington, ON) according to the manufacturer's recommendations. Three days later, the transfected cells were incubated in the presence of G418 (1.2 mg/mL) and four weeks later, the pool of G418 resistant cells was transfected with pAdCR5GFPq. Two days later, the highest GFP expressing cells were sorted on an EPICS TM V (Model 752; Beckman-Coulter, Hialeah, Fla.) multiparameter laser flow cytometer and cell sorter, and transferred into 96-well plates at a density of one cell per well in the presence of 1.2 mg/mL of G418. Confluent clones were picked, expended and the amount of cTA synthesized by the cells was determined indirectly by measuring the intensity of GFP by flow cytometry using a Coulter EPICS™ XI flowcytometer (Beckman-Coulter, Hialeah, Fla.) 24 hours after infection with an adenovirus vector expressing GFP regulated by the CR5 promoter (AdCR5GFPq). A second round of cloning was performed by transferring individual cells from the clones that were the most fluorescent after transduction with AdCR5GFPq into 96-well plates using a cell micromanipulator (Caron et al., 2000). The cells were grown in the absence of G418 and confluent colonies were picked and expanded. The quantity of cTA produced by these cells was evaluated indirectly by flow cytometry by measuring the intensity of GFPq produced after infection with AdCR5GFPq. One of the most productive subclones (CHOcTA-5F-1) was expanded. A small cell bank was generated and kept frozen in liquid nitrogen.

CHO-SF(b) cells (Invitrogen, Burlington, ON) were thawed and grown in 50 ml CD CHO medium (Invitrogen, Burlington, ON) supplemented with 1× HT supplement (Invitrogen, Burlington, ON), 4 mM L-glutamine (Invitrogen, Burlington, ON) at 37° C. After 3 passages, a bank of 22 frozen vials was made using 10% DMSO (Invitrogen, Burlington, ON) as described below. The cell bank was tested for the presence of mycoplasma at INRS-Institut Armand-Frappier, Montreal, QC. No Mycoplasma was detected. The CHOcTA cells stably expressing the cumate transactivator (cTA) were generated by transfecting CHO-SF(b) cells with linearized pMPG-/tk-neo/cymR_VP16-nls using Lipofectamine 2000 (Invitrogen, Burlington, ON) according to the manufacturer's recommendations. The next day, the cells were separated into 96-well/plate at a concentration of 10 000 or 5000 cells per well in the presence of G418 (1.2 mg/mL). Three to four weeks later, the resistant colonies were picked and expanded. The amount of cTA synthesized by the cells was determined indirectly by measuring the intensity of GFP by flow cytometry 24 hours after infection with an adenovirus vector expressing GFP regulated by the CR5 promoter (AdCR5GFPq). One month and three weeks after the initial transfection, a second round of cloning was performed by transferring individual cells from one of the clones that was the most fluorescent after transduction with AdCR5GFPq (CHOs cTA #10) into 96-well plates using a cell micromanipulator (Caron et al., 2000). The cells were grown in the absence of G418 and confluent colonies (three to four weeks later) were picked and expanded. The quantity of cTA produced by these cells was evaluated indirectly by flow cytometry by measuring the intensity of GFPq produced after infection with AdCR5GFPq. One of the most productive subclones (CHOcTA-10-9) was expended. A small cell bank was generated and kept frozen in liquid nitrogen. The cell bank was tested for the presence of mycoplasma at INRS-Institut Armand-Frappier. No Mycoplasma was detected.

CHO cells expressing the cumate transactivator (CHOcTA, clone 10-9 and 5F-1) were transfected with linearized pMPGCR5IgG1-Vk+hH460 (SspI digestion) using Lipofectamine 2000 reagent. The next day, the cells were transferred into 96-well plates at different concentrations (10 000 or 5000 cells/well). At this time point, 600 µg/mL of hygromycin B was added to the medium. After two to three weeks, the supernatant of the resistant colonies (378 clones) was analyzed for the presence of IgG1 antibody by ELISA (the quantification determined by ELISA and by western blot was only a rough estimate of the antibody production, because the standard used for quantification (purified human IgG) was different than the chimeric IgG1 of H460-16-12 produced by the cells.). A total of 104 clones produced detectable amount of antibody.

Figure 40:
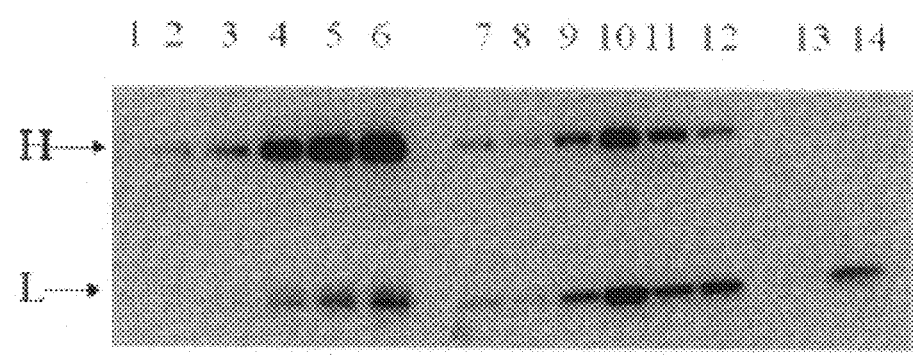
FIG. 40. Quantification by Western blot of H460-16-2 (IgG1 isotype) produced by the different clones (lanes 1-6: 0, 25, 50, 100, 150 and 200 ng human IgG respectively; lane 7: clone 17; lane 8: clone 71; lane 9: clone 80; lane 10: clone6'; lane 11: clone 47'; lane 12: clone 147'; lane 13: 100 ng pure H460-16-2; lane 14: 10 microliters hybridoma serum).
Figure 41:
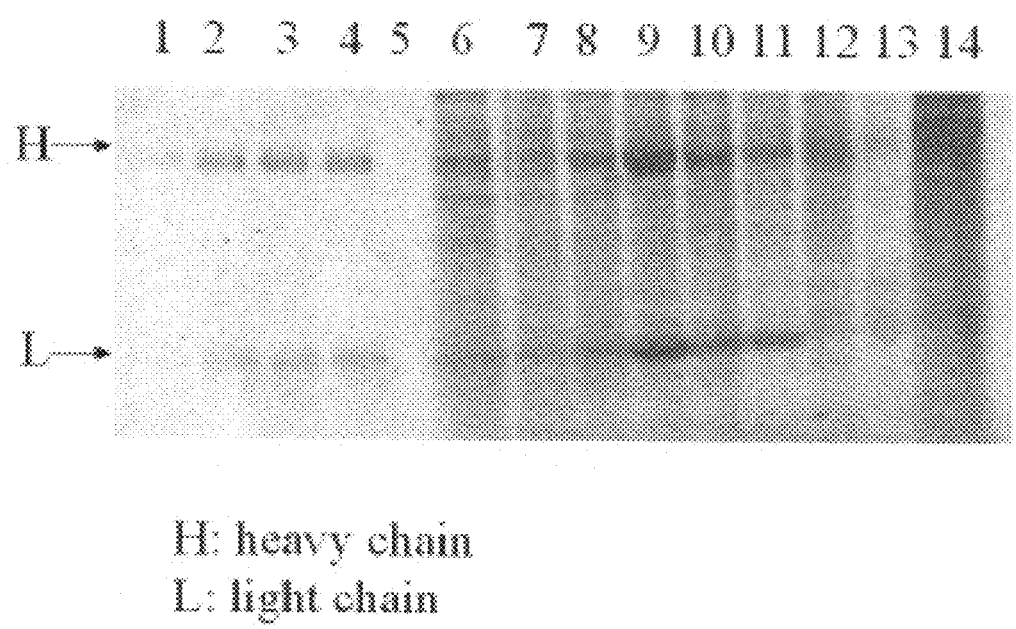
FIG. 41. Quantification by SDS-PAGE of H460-16-2 (IgG1 isotype) produced by the different clones (lanes 1-5: 50, 100, 150, 200 and 0 ng human IgG respectively; lane 6: clone 17; lane 7: clone 71; lane 8: clone 80; lane 9: clone6'; lane 10: clone 47'; lane 11: clone 147'; lane 12: 100 ng human IgG with cell supernatant; lane 13: 100 ng pure H460-16-2; lane 14: 10 microliters hybridoma serium).

Twelve clones were then amplified and tested for expression of the antibody by western blot and SDS-PAGE using a 24 hours productivity test. The production of antibody was also evaluated in batch culture at 30° C. for 6 to 13 days (FIGS. 40 and 41). Production was performed at 30° C. because the CR5 promoter is much stronger at this temperature.

Six of the clones were 17, 71, 80, 6', 47' and 147'. Clones 17, 71 and 80 were generated using CHOcTA-10-9 and clones 6', 47' and 147' were generated using CHOcTA-5F1. These 6 clones secreted 4 to 6 pg/cell/day at 37° C. as estimated by coomassie Fluo-Orange staining using the human IgG as standard.

6.0 Initial Cloning to Produce (ch)ARH1460-16-2-IgG2

6.1 Construction of pMPGCR5VK+h460-IgG2

Figure 42:
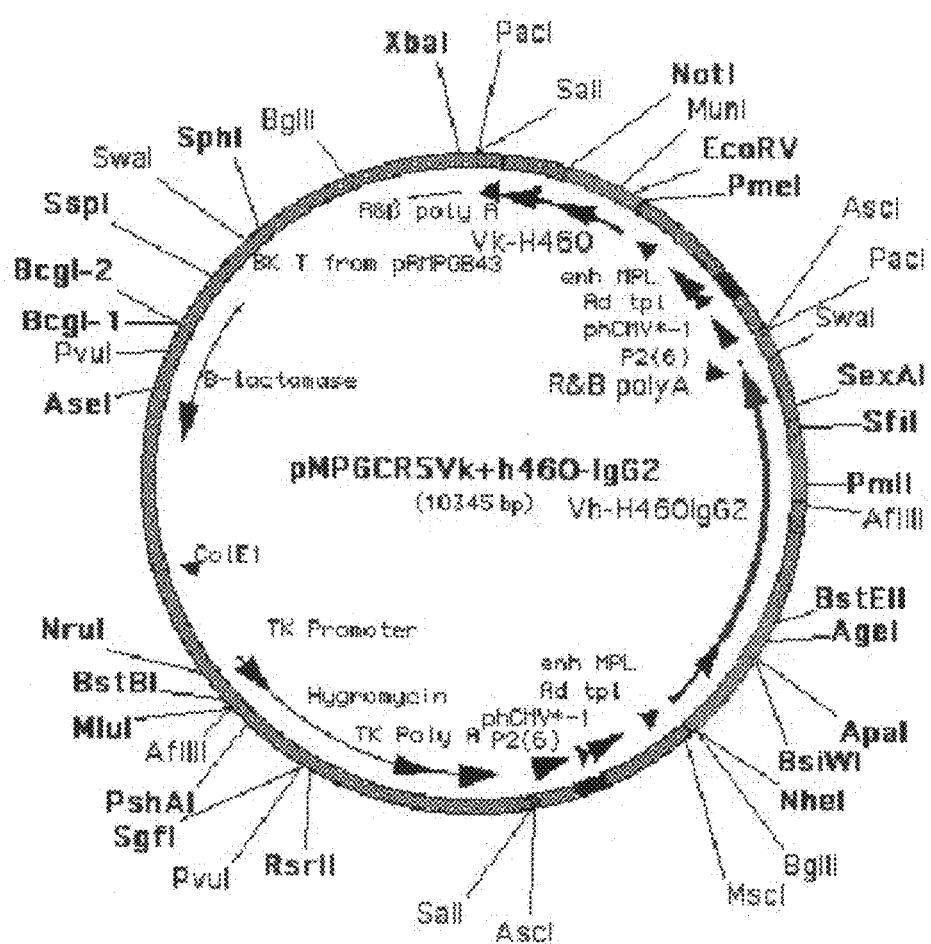
FIG. 42. Map of pMPGCR5VK+h460-IgG2. R&B poly A: Rabbit β-globin poly adenylation signal; phCMV : Cytomegalovirus promoter; Ad Tp1: adenovirus tripartite leader; P2 (6): binding domain for the cumate transactivator (cTA); Vh-H460IgG2: coding sequence for the heavy chain of H460-16-2; Vk-H460: coding sequence for the light chain of H460-16-2. BK T: Portion of the large T antigen of BK virus; TK: Thymidine kinase; enh MPL: enhancer of the adenovirus major late promoter.

This plasmid contains the heavy and light chain of the chimeric IgG2 isotype of H460-16-2 regulated by the cumate inducible promoter (CR5). In addition, this plasmid contains the resistance for hygromycin for selection of stable clones (FIG. 42). This plasmid was produced through several PCR and subcloning steps that are described below.

A) Chimerization of the Light Chain (Construction of pMPGCR5VkH460)

A DNA fragment (PCR B) encoding the variable region of the light chain of H460-16-2 was isolated by PCR using plasmid pVkH460-16-2#1-1 (SEQ ID NO:1) and primers ARvarlc (SEQ ID NO:26) and jctvar-k#3 (SEQ ID NO:27) (FIG. 43). A DNA fragment (PCR A) encoding the constant region of the human kappa light chain of IgG was isolated by PCR using plasmid pMPGB43k and primers ARkappa (SEQ ID NO:28) and jctk-var#3 (SEQ ID NO:29) (FIG. 43). The variable region was assembled with the constant region by PCR using fragments PCR B and PCR A as a template and primers Arvar1c (SEQ ID NO:26) and ARkappa (SEQ ID NO:28). The resulting DNA fragment (PCR C) was digested with BamHI and ligated into pMPGCR5B43k (FIG. 38) previously digested with BamH1 to remove the B43 light chain. Before ligation, the linearized vector was dephosphorylated by treatment with calf intestinal phosphatase (CIP). The resulting vector was called pMPGCR5VkH460koz. The complete light chain was sent for sequencing. The expected nucleotide sequence was obtained except for a mutation within the Kosak sequence. This mutation was corrected by swapping the variable region of pMPGCR5VkH460koz with the variable region of pMPGCR5VkH460wrongjct (see below) by digesting both plasmids with KpnI and by ligating the proper DNA fragments together. The resulting plasmid was called pMPGCR5VkH460and the nucleotide sequence of the light chain was confirmed by sequencing.

B) Construction of pMPGCR5VkH460wrongjct

This plasmid contains a chimeric light chain of H460-16-2 with a different junction between the variable and the constant regions. To construct this plasmid, a DNA fragment (PCR B1) encoding the variable region of the light chain of H460-16-2 was isolated by PCR using plasmid pVkH460-16-2#1-1 (SEQ ID NO:1) and primers ARvarlc (SEQ ID NO:26) and ARjctvar-k (SEQ ID NO:30) (FIG. 43). A DNA fragment (PCR A1) encoding the constant region of the human kappa light chain of IgG was isolated by PCR using plasmid pMPGB43k and primers ARkappa (SEQ ID NO:28) and ARjctk-var (SEQ ID NO:31) (FIG. 43). The variable region was assembled with the constant region by PCR using fragments PCR B1 and PCR A1 as a template and primers Arvarlc (SEQ ID NO:26) and ARkappa (SEQ ID NO:28). The resulting DNA fragment (PCR C1) was then digested with BamHI and ligated into pMPGCR5B43k (FIG. 38) previously digested with BamH1 to remove the B43 light chain. Before ligation, the vector was dephosphorylated by treatment with CIP. The resulting vector was called pMPGCR5VkH460wrongjctkoz. The nucleotide sequence of the light chain was confirmed by sequencing.

C) Chimerization of the Heavy Chain (Construction of pKCR5IgG2VhH460).

A DNA fragment (PCR D) encoding the variable region of the heavy chain of H460-16-2 was isolated by PCR using plasmid pVhH460-16-2 #3 (SEQ ID NO:10) and primers ARigg2varlc (SEQ ID NO:32) and ARhvarswa (SEQ ID NO:33) (FIG. 43). The PCR product was digested with ApaI and ligated to a 4.6-kb DNA fragment encoding the constant region of human IgG2. This vector was obtained by digesting pkHc (BRI, NRC, Montreal Qc) with ApaI followed by treatment with CIP. The resulting plasmid was called pKIgG2-VhH460.

The complete heavy chain encoded by pKIgG2-VhH460was released by digestion with SwaI and cloned into pKCR5B43G3 (FIG. 39) previously digested with HindIII to remove the B43 heavy chain. Before ligation the plasmid was blunted by treatment with T4 DNA polymerase and dephosphorylated with CIP. The resulting plasmid was called pKCR5IgG2VhH460wrongjct and the nucleotide sequence of the complete heavy chain was confirmed by sequencing. The junction between the variable and the light chain of the chimeric IgG2 was unusual. For this reason, it was decided to modify it. A DNA fragment containing the proper junction was amplified by PCR of pKCR5IgG2VhH460wrongjct using primers ApaICR5 (SEQ ID NO:34) and IgG2TVSSASTK (SEQ ID NO:35) (FIG. 43). The PCR fragment was digested with ApaI and cloned into pKCR5IgG2VhH460wrongjct previously digested with ApaI. Before ligation the 4.6 kb fragment was dephosphorylated by treatment with CIP. The resulting plasmid was called pKCR5IgG2VhH460 and the nucleotide sequence of the chimeric IgG2 was confirmed by sequencing.

D) Final Assembly of the IgG2 Expression Vector

The heavy chain expression cassette (promoter, coding sequence, poly A signal) was excised from pKCR5IgG2VhH460 by digestion with AscI and inserted into the AscI site of pMPGCR5VkH460 which was dephosphorylated by treatment with CIP before ligation. The complete nucleotide sequence of the heavy and light chains were confirmed by sequencing. A map of the resulting construct (pMPGCR5VK+h460-IgG2) is presented in FIG. 42.

7.0 Production of Initial Clones

Figure 44:
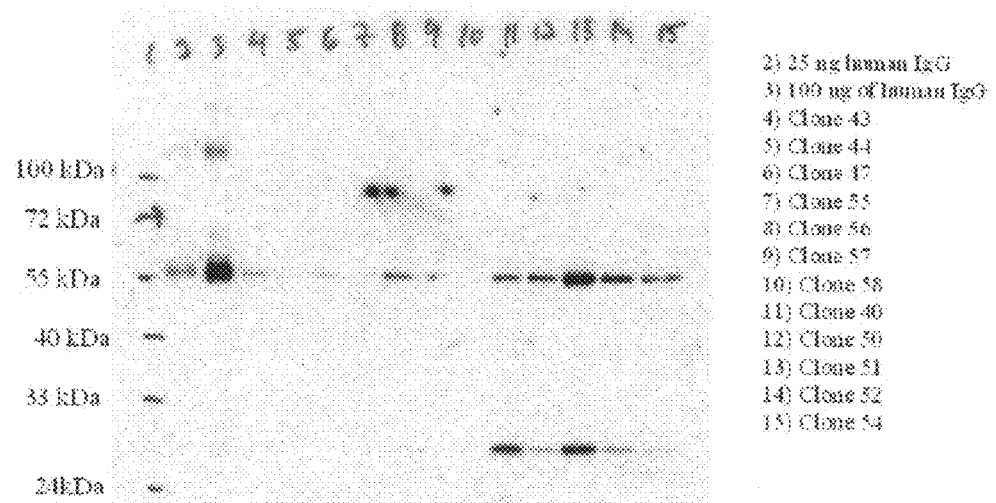
FIG. 44. Expression of the IgG2 isotype of H460-16-2 by western blot after the first round of cloning. 250 000 cells from the selected clones were resuspended into 500 microliters of medium. After 24 hours at 37° C., 10 microliters of supernatant were analyzed by western blot using an anti-human antibody conjugated to HRP.

CHO-cTA (Clone 10-9) cells growing in serum free chemically defined medium were transfected with the plasmid expressing the chimeric IgG2 antibody pMPGCR5VK+h460-IgG2 (FIG. 42) and stable clones were generated in the presence of hygromycin. 374 clones were analyzed by ELISA for expression of IgG2 antibody. 80 clones were positive for the expression of the antibody. The quantity of antibody secreted by the 58 most productive clones was analyzed by western blot or SDS-PAGE (FIG. 44). The most productive clones produced between 5 to 10 pg/cell/day at 37° C. The 6 clones were: Clone 40, 50, 51, 52, 54 and 56.

8.0 Selection of High Producing Clones

Figure 45:
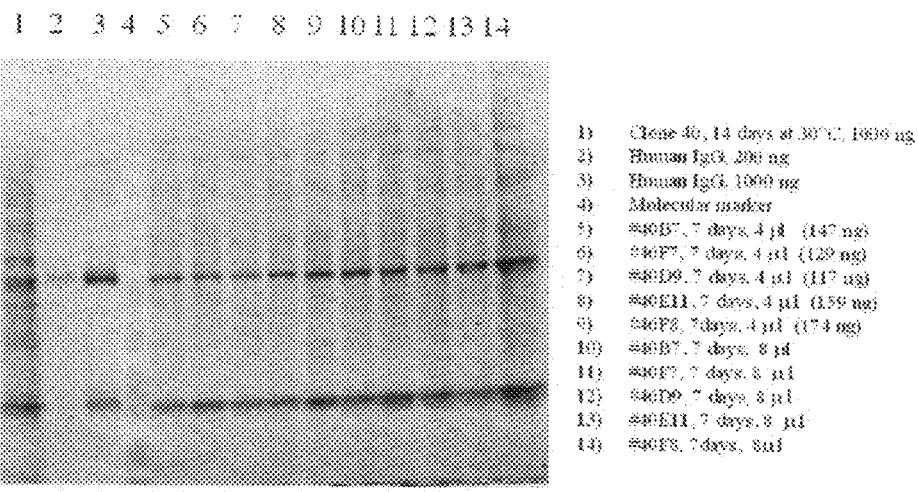
FIG. 45. Cells from different subclones were plated at 5.0×105 cells/mL at 37° C. When the cells density reached 1.5 to 2.0'106 cells/mL, they were transferred at 30° C. After 7 days at 30° C. the indicated amount of supernatant were analyzed by SDS-PAGE followed by staining with Coomassie Fluor-Orange. The amount (ng/microliter) of antibody produced is indicated.

Clones 40, 50, 51, 54 and 56 were subcloned using the micromanipulator (about 50 cells per clone) in the absence of selective pressure. The production level of 51 subclones were tested by Western blot analysis or by SDSPAGE followed by coomassie Fuo-Orange stainging (FIG. 45). The most productive subclones were the following with the amount of antibody produced at 37° C. indicated in brackets: 40F8 (11), 40B7 (7), 56B9 (7), 40F7 (7), 56E9 (5), 40E11 (5), 40D9 (6), 56B8 (6), 56F11 (4) and 54E10 (3).

9.0 Testing of Supernatants

The supernatant from each chimeric IgG1 and IgG2 clone was used as a Western blot probe to determine if IgGs were present that were able to detect the target antigen for the murine antibody H460-16-2 (CD44). A sample containing 300 micrograms of total membrane fraction of MDA-MB-231 human breast cancer cells was boiled and analyzed by SDS-PAGE (preparative gel, 10% acrylamide)/Western immunoblotting. The Western blots were probed with 1:2 dilution of the cell culture supernatants (with 10% skim milk in TBST) following standard procedure for Western blotting.

Figure 46:
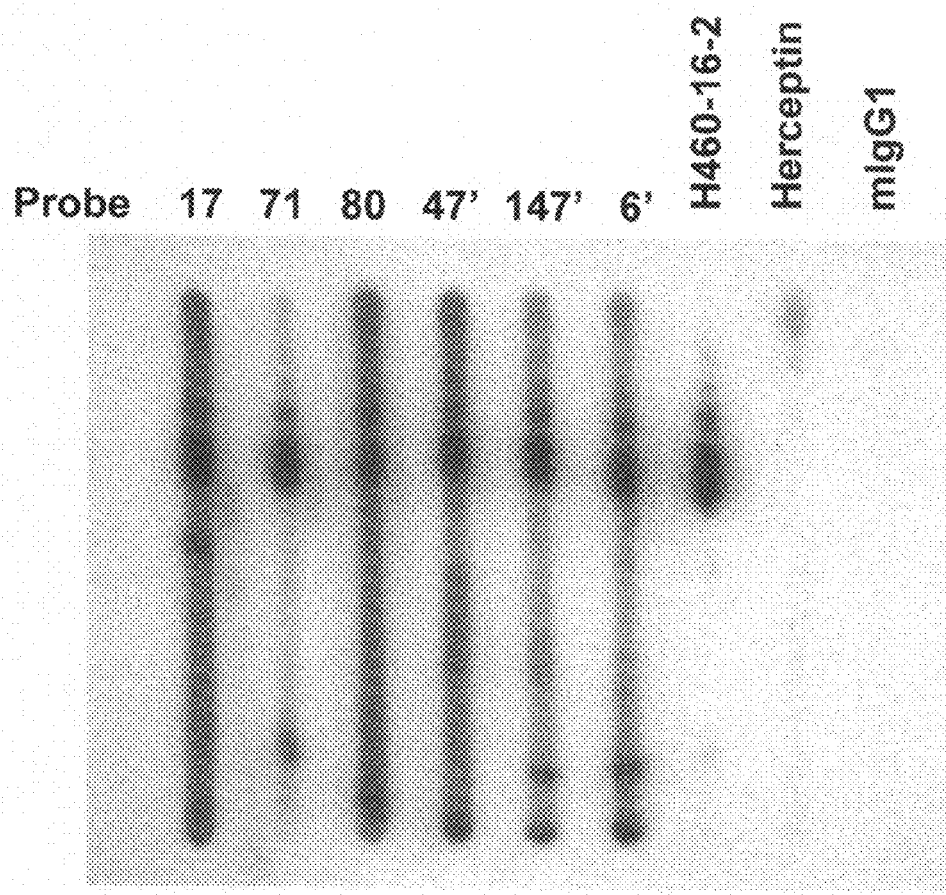
FIG. 46. Characterization of the chimeric (ch)ARH460-16-2-IgG1 clones by Western blotting on total membrane fractions of MDA-MB-231 cells.
Figure 47:
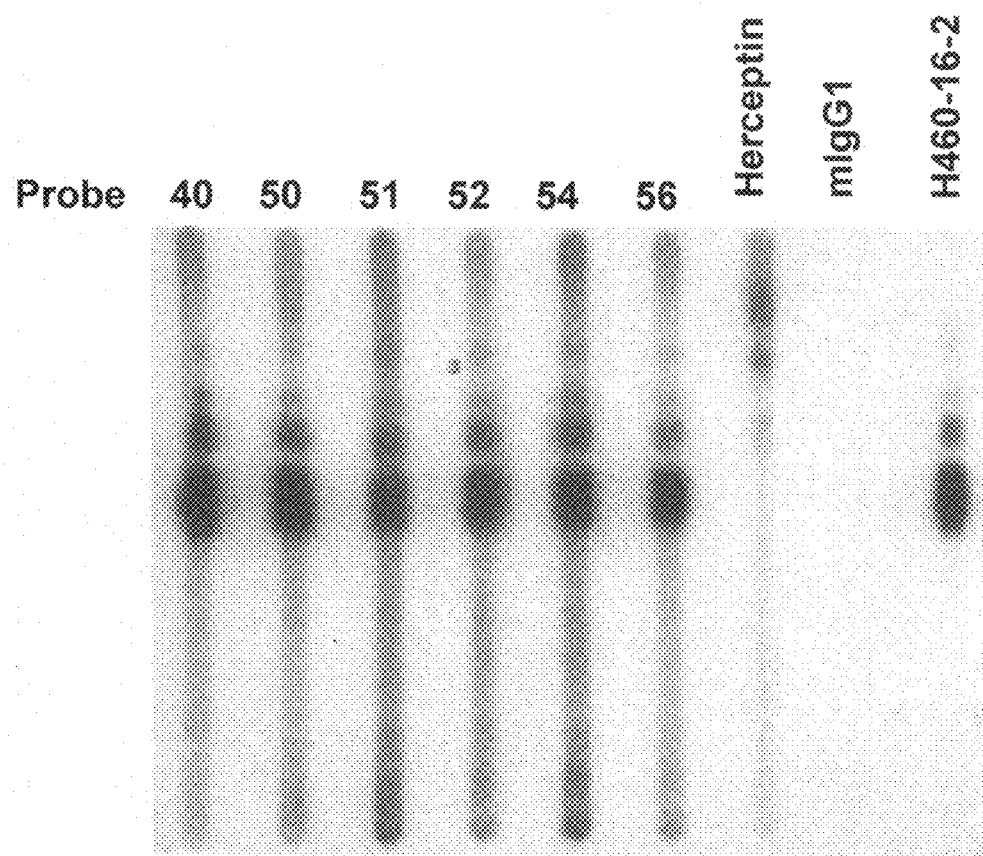
FIG. 47. Characterization of the chimeric (ch)ARH460-16-2-IgG2 clones by Western blotting on total membrane fractions of MDA-MB-231 cells.

The results indicate that all the supernatants (from chimeric IgG1 and chimeric IgG2-secreting clones) were able to detect CD44, with a signal that was similar to that obtained with the murine parental MAb, at similar (calculated) concentrations (5 micrograms/mL; FIGS. 46 and 47).

10.0 Production in Bioreactors of the Selected Clone

Chimeric IgG1 clone 6' appeared to be the highest secreting clone based on SDS-PAGE analysis and bound in a similar fashion as murine H460-16-2 on membrane preparations of MDA-MB-231 cells in a Western blot. Therefore, clone 6' was used to produce the antibody in batch culture in shaker flasks at 30° C. The antibody concentration in the batches was evaluated by SDS-PAGE followed by Coomassie Fluo-Orange staining (FIG. 48). The volume of the different batches and the antibody concentration were the following: batch super22Nov: 1.6 L, 150mg/L; batch N3: 0.65 L, 200 mg/L; batch N4: 0.65 L, 100 mg/L and batches N5 and N6: 0.8 L, 200 mg/L. Clone 6' was used for all future chimeric IgG1 studies and is referred to as (ch)ARH460-16-2-IgG1.

Figure 49:
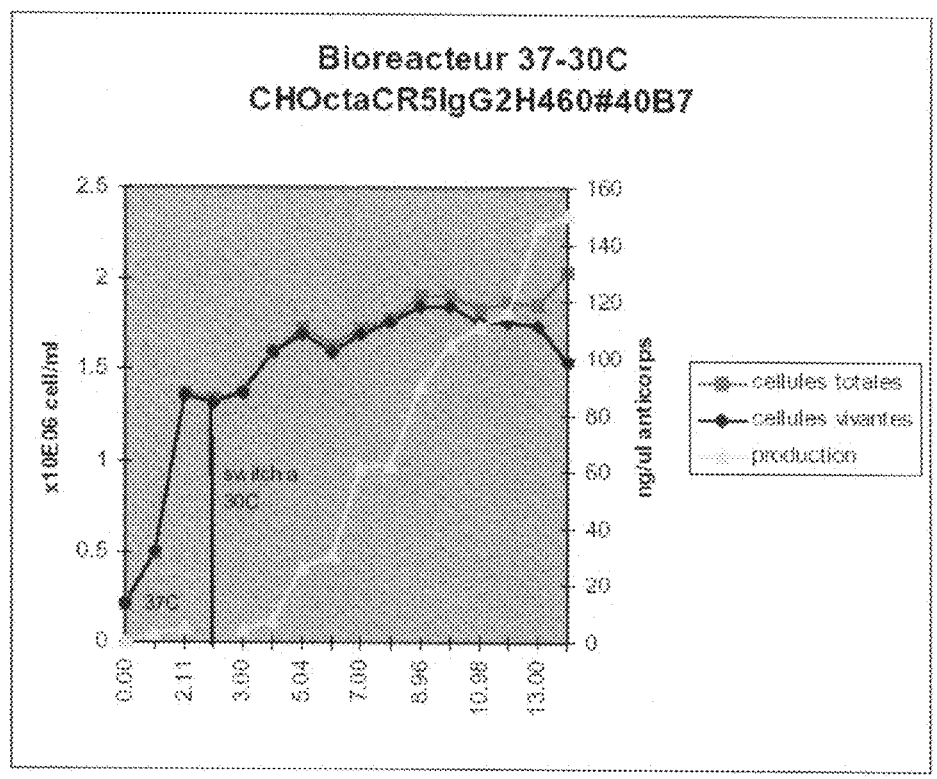
FIG. 49. Analysis of the antibody concentration, by SDS-PAGE followed by staining with Coomassie Fluo-Orange staining, of the antibody produced by the clone 40B7.

Chimeric IgG2 clone 40B7 appeared to be the highest secreting clone based on SDS-PAGE analysis and bound in a similar fashion as murine H460-16-2 on membrane preparations of MDA-MB-231 cells in a Western blot. Therefore, clone 40B7 was produced in greater quantities (FIG. 49). 20 liter of medium containing about 140 mg/liter of antibody was produced. The concentration of antibody in the medium was determined by SDS-PAGE followed by staining using coomassie FluOrange. Clone 40B7 was used for all future chimeric IgG2 studies and is referred to as (ch)ARH460-16-2-IgG2.

EXAMPLE 10

In vivo Tumor Experiments with MDA-MB-231 Cells

With reference to FIGS. 50 and 51, 4 to 6 week old female SCID mice were implanted with 5 million human breast cancer cells (MDA-MB-231) in 100 microliters saline injected subcutaneously in the scruff of the neck. Tumor growth was measured with calipers every week. When the majority of the cohort reached an average tumor volume of 91 $mm^3$ (range 55-143 $mm^3$) at 35 days post-implantation, mice were divided into blocks based on tumor size. Mice from the blocks were randomly assigned to the 4 treatment groups (10 per group) so that the mean tumor volume in each group was not significantly different from the others. H460-16-2, (ch)ARH460-16-2-IgG1, (ch)ARH460-16-2-IgG2 test antibodies or buffer control were administered intraperitoneally to each cohort, with dosing at 15 mg/kg of antibodies in a volume of 300 microliters after dilution from the stock concentration with a diluent that contained 2.7 mM KCl, 1 mM $KH_2PO_4$, 137 mM NaCl and 20 mM $Na_2HPO_4$. The antibodies were then administered 3 times per week for a total of 10 doses in the same fashion until day 57 post-implantation. Tumor growth was measured about every seventh day with calipers until day 62 post-implantation or until individual animals reached the CCAC end-points. Body weights of the animals were recorded once per week for the duration of the study. At the end of the study all animals were euthanised according to CCAC guidelines.

Figure 50:
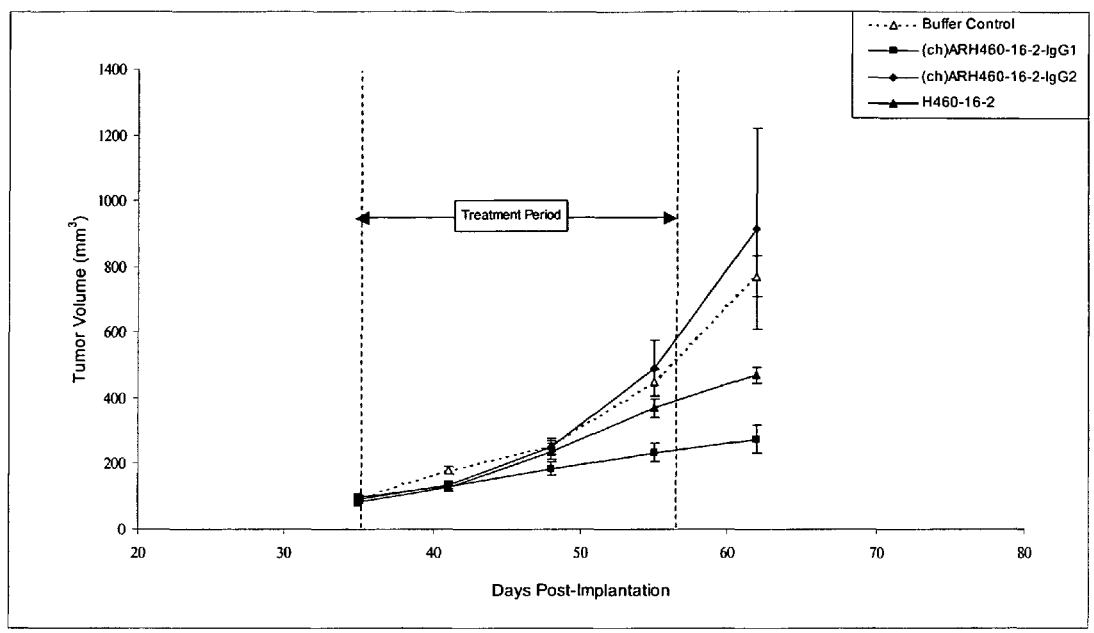
FIG. 50 demonstrates the effect of treatment with H460-16-2, (ch)ARH460-16-2-IgG1, and (ch)ARH460-16-2-IgG2 on tumor growth in a mouse model of human breast cancer. Tumor volume is presented as the group mean±SEM. Vertical dashed lines indicate the first and last day of dosing.

As demonstrated in FIG. 50, both murine H460-16-2 and (ch)ARH460-16-2-IgG1 reduced tumor growth in an established MDA-MB-231 in vivo model of human breast cancer. At day. 62, 5 days after the last dose was administered, treatment with H460-16-2 resulted in a tumor growth inhibition of 39% (Mean T/C=57%). This reduction in tumor growth was significantly different from the control (p=0.0037). The chimeric antibody (ch)ARH460-16-2-IgG1 resulted in an enhanced tumor growth inhibition of 64% (Mean T/C=26.9%; p<0.0001). By contrast, the IgG2 version of the chimeric antibody, (ch)ARH460-16-2-IgG2 showed no inhibition in tumor growth when compared with the buffer control (TGI=0%; Mean T/C=122%; p=0.7264).

Figure 51:
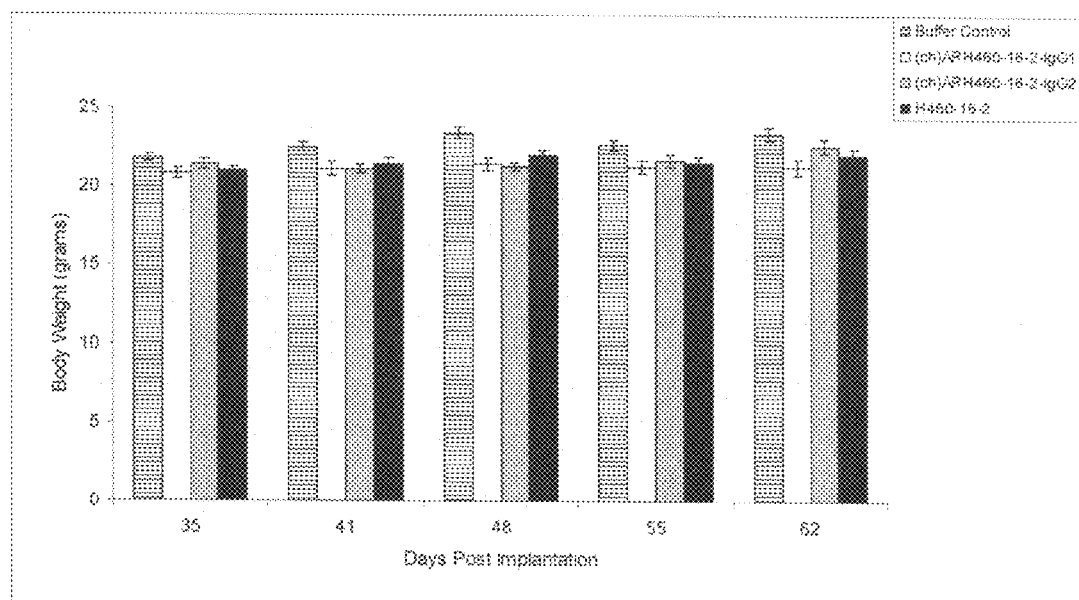
FIG. 51 demonstrates the effect of treatment with monoclonal antibodies on body weight over the duration of the study. Body weight is presented as the group mean±SEM.

There were no clinical signs of toxicity throughout the study. Body weight measured at weekly intervals was a surrogate for well-being and failure to thrive. FIG. 51 presents the results of the body weight of each of the treated groups over the course of the study. There were no significant changes in body weight in mice from either the H460-16-2 or the (ch)ARH460-16-2-IgG2 treated groups when compared to the buffer control group. However there was a significant decrease in body weight (p=0.0005) between the buffer control-treated group and the (ch)ARH460-16-2-IgG1 treated groups.

In summary, (ch)ARH460-16-2-IgG1 demonstrates the same or greater efficacy compared to the murine antibody in the MDA-MB-231 breast cancer model. By contrast, the (ch) ARH460-16-2-IgG2 chimeric antibody did not reduce tumor growth in this model of human MDA-MB-231 breast cancer.

EXAMPLE 11

Annexin-V Staining of MDA-MB231 Cells that were Treated with H460-16-2, (ch)ARH460-16-2-IgG1 and (ch)ARH460-16-2IgG2

Annexin-V staining was performed to determine whether the chimeric versions of H460-16-2 were able to induce apoptosis in the same manner as the murine counterpart on the MDA-MB-231 human breast cancer cell line. MDA-MB-231 cells were treated for 24 hours with H460-16-2, (ch) ARH460-16-2-IgG1 or (ch)ARH460-16-2-IgG2 at 0.25, 2.5 and 20 micrograms/mL. Each antibody was tested in triplicate along with the appropriate isotype control (1B7. 11, anti-TNP, murine IgG1, kappa, produced in-house; human myeloma IgG1, k, Sigma, Oakville, ON; human myeloma IgG2, k, Sigma, Oakville, ON) tested at the identical concentration. An untreated sample was included as the negative control and camptothecin (Biovision; Exton, Pa.) was included as the positive control. The FACS instrument was compensated for optical spillover of the fluorescent conjugates using fluorometric beads (BD Bioscience, Oakville, ON). The cells were then stained with Annexin-V and 7AAD and acquired on a FACSArray within 1 hour.

In two independent experiments both the murine and the two chimeric H460-16-2 antibodies were compared to each other and to their appropriate isotype control antibodies (FIG. 52). FIG. 52 also shows the average of the 2 experiments. Spontaneous apoptotic effects of cells treated with isotype control were found to be similar to cells treated with vehicle only. The murine and human chimeric IgG1 and IgG2 H460-16-2 antibodies were all found to induce apoptosis in the breast cancer cell line in a dose dependent manner in each experiment, with greater apoptotic effect seen with both the (ch)ARH460-16-2 IgG1 and IgG2 antibodies. Results indicate that in vitro the (ch)ARH460-16-2-IgG2 antibody has the greatest apoptotic effect when compared to the chimeric IgG1 antibody.

All 3 antibodies showed an increase in the percentage necrotic and necrotic/apoptotic populations over their prospective isotype controls. The largest increase in the percentage necrotic and necrotic/apoptotic populations was seen with (ch)ARH460-16-2-IgG2, then (ch)ARH460-16-2-IgG1 and then H460-16-2.

The preponderance of evidence shows that H460-16-2, (ch)ARH460-16-2-IgG2, (ch)ARH460-16-2-IgG1 and AR37A335.8 mediate anti-cancer effects through ligation of epitopes present on CD44. It has been shown, in Example 5, that the H460-16-2 and AR37A335.8 antibody can be used to immunoprecipitate the cognate antigen from expressing cells such as MDA-MB-231 cells. Further it could be shown that the H460-16-2, (ch)ARH460-16-2-IgG2, (ch)ARH460-16-2-IgG1 and AR37A335.8 antibody could be used in detection of cells and/or tissues which express a CD44 antigenic moiety which specifically binds thereto, utilizing techniques illustrated by, but not limited to FACS, cell ELISA or IHC.

Thus, it could be shown that the immunoprecipitated H460-16-2, (ch)ARH460-16-2-IgG2, (ch)ARH460-16-2-IgG1 and AR37A335.8 antigen can inhibit the binding of either antibody to such cells or tissues using FACS, cell ELISA or IHC assays. Further, as with the H460-16-2, (ch) ARH460-16-2-IgG2, (ch)ARH460-16-2-IgG1 and AR37A335.8 antibody, other anti-CD44 antibodies could be used to immunoprecipitate and isolate other forms of the CD44 antigen, and the antigen can also be used to inhibit the binding of those antibodies to the cells or tissues that express the antigen using the same types of assays.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objects and obtain the ends and advantages mentioned, as well as those inherent therein. Any oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. The isolated monoclonal antibody produced by the hybridoma deposited with the IDAC as accession number 280104-06, or an antigen binding fragment produced from said isolated monoclonal antibody.

2. A humanized form of the isolated monoclonal antibody of claim 1, or an antigen binding fragment produced from said humanized form of said isolated monoclonal antibody, wherein said humanized form of the isolated monoclonal antibody or an antigen binding fragment thereof, binds to CD 44.

3. A chimeric form of the isolated monoclonal antibody of claim 1, or an antigen binding fragment produced from said chimeric form of said isolated monoclonal antibody, wherein said chimeric form of the isolated monoclonal antibody or an antigen binding fragment thereof, binds to CD 44.

4. The hybridoma deposited with the IDAC as accession number 280104-06.

5. The isolated antibody or antigen binding fragment of any one of claims 1, 2, or 3 conjugated with a member selected from the group consisting of toxins, enzymes, radioactive compounds, and hematogenous cells.

* * * * *

UNITED STATES PATENT AND TRADEMARK OFFICE
CERTIFICATE OF CORRECTION

| | | |
|---|---|---|
| PATENT NO. | : 7,947,496 B2 | Page 1 of 1 |
| APPLICATION NO. | : 11/364013 | |
| DATED | : May 24, 2011 | |
| INVENTOR(S) | : Young et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 180 days.

Signed and Sealed this
Thirteenth Day of September, 2011

David J. Kappos
*Director of the United States Patent and Trademark Office*

SEQUENCE LISTING

<160> NUMBER OF SEQ ID NOS: 36

<210> SEQ ID NO 1
<211> LENGTH: 810
<212> TYPE: DNA
<213> ORGANISM: Artificial
<220> FEATURE:
<223> OTHER INFORMATION: commercial vector having insert ARH460-16-2 V
      kappa (M) 1-1

<400> SEQUENCE: 1

| | | | | | |
|---|---|---|---|---|---|
| gaattgtaat | acgactcact | atagggcgaa | ttgggccctc | tagatgcatg | ctcgagcggc | 60 |
| cgccagtgtg | atggatatct | gcagaattcg | cccttgatat | ggtatcctca | cctcagttcc | 120 |
| ttggtctcct | gttgctctgt | tttcaaggta | ccagatgtga | tatccagatg | acacagacta | 180 |
| catcctccct | gtctgtctct | ctgggagaca | gagtcaccat | caattgcagg | gcaagtcagg | 240 |
| acattaacaa | ttatttaaac | tggtatcagc | agaaaccaga | tggaactgtt | aaactcctga | 300 |
| tctactacac | atcaagatta | cactcaggag | tcccatcaag | gttcagtggc | agtgggtctg | 360 |
| gaacagattt | ttctctcacc | attagcaacc | tggagaaaga | agatgttgcc | acttactttt | 420 |
| gccaacaggg | tagtacgctt | ccattcacgt | tcggctcggg | gacaaagttg | gaaataaaac | 480 |
| gggctgatgc | tgcaccaact | gtatccatct | tcccaccatc | cagtaagctt | gggaagggcg | 540 |
| aattccagca | cactggcggc | cgttactagt | ggatccgagc | tcggtaccaa | gcttggcgta | 600 |
| atcatggtca | tagctgtttc | ctgtgtgaaa | ttgttatccg | ctcacaattc | cacacaacat | 660 |
| acgagccgga | agcataaagt | gtaaagcctg | gggtgcctaa | tgagtgagct | aactcacatt | 720 |
| aattgcgttg | cgctcactgg | ccgctttcca | gtcgggaaac | ctgtcgtgcc | agctgcatta | 780 |
| atgaatcggc | caacgcgcgg | ggagaggcgg | | | | 810 |

<210> SEQ ID NO 2
<211> LENGTH: 820
<212> TYPE: DNA
<213> ORGANISM: Artificial
<220> FEATURE:
<223> OTHER INFORMATION: commercial vector having insert ARH460-16-2 V
      kappa (M)1-2

<400> SEQUENCE: 2

| | | | | | |
|---|---|---|---|---|---|
| gcaattgtaa | tacgactcac | tatagggcga | attgggccct | ctagatgcat | gctcgagcgg | 60 |
| ccgccagtgt | gatggatatc | tgcagaattc | gcccttccca | agctactgga | tgtgggaag | 120 |
| atggatacag | ttggtgcagc | atcagcccgt | tttatttcca | actttgtccc | cgagccgaac | 180 |
| gtgaatggaa | gcgtactacc | ctgttggcaa | aagtaagtgg | caacatcttc | tttctccagg | 240 |
| ttgctaatgg | tgagagaaaa | atctgttcca | gacccactgc | cactgaacct | gatgggact | 300 |
| cctgagtgta | atcttgatgt | gtagtagatc | aggagtttaa | cagttccatc | tggtttctgc | 360 |
| tgataccagt | ttaaataatt | gttaatgtcc | tgacttgccc | tgcaattgat | ggtgactctg | 420 |
| tctcccagag | agacagacag | ggaggatgta | gtctgtgtca | tctggatatc | acatctggta | 480 |
| ccttgaaaac | agagcaacag | gagaccaagg | aactgagctg | tggataccat | gtcgactagt | 540 |
| aagggcgaat | tccagcacac | tggcggccgt | tactagtgga | tccgagctcg | gtaccaagct | 600 |
| tggcgtaatc | atggtcatag | ctgtttcctg | tgtgaaattg | ttatccgctc | acaattccac | 660 |
| acaacatacg | agccggaagc | ataaagtgta | aagcctgggg | tgcctaatga | gtgagctaac | 720 |
| tcacattaat | tgcgttgcgc | tcactgcccg | ctttccagtc | gggaaacctg | tcgtgccagc | 780 |

```
tgcattaatg aatcggccac gcgcggggag aggcgggttt              820
```

<210> SEQ ID NO 3
<211> LENGTH: 860
<212> TYPE: DNA
<213> ORGANISM: Artificial
<220> FEATURE:
<223> OTHER INFORMATION: commercial vector having insert ARH460-16-2 V
      kappa (M) 1-3

<400> SEQUENCE: 3

```
gaattgtaat acgactcact atagggcgaa ttgggccctc tagatgcatg ctcgagcggc     60
cgccagtgtg atgggatatc tgcagaattc gcccttggta cctcagctc  agttccttgg   120
tctcctgttg ctctgttttc aaggtaccag atgtgtatc  cagatgacac agactacatc   180
ctccctgtct gtctctctgg agacagagt  caccatcaat tgcagggcaa gtcaggacat   240
taacaattat ttaaactggt atcagcagaa accagatgga actgttaaac tcctgatcta   300
ctacacatca gattacact  caggagtccc atcaaggttc agtggcagtg gtctgggaac   360
agatttttct ctcaccatta gcaacctgga gaagaagat  gttgccactt acttttgcca   420
acagggtagt acgcttccat tcacgttcgg ctcggggaca agttggaaa  taaaacgggc   480
tgatgctgca ccaactgtat ccatcttccc accatccagt aagcttggga agggcgaatt   540
ccagcacact ggcggccgtt actagtggat ccgagctcgg taccaagctt ggcgtaatca   600
tggtcatagc tgtttcctgt gtgaaattgt tatccgctca caattccaca caacatacga   660
gccgaaagca taaagtgtaa agcctggggt gcctaatgag tgagctaact cacattaatt   720
gcgttgcgct cactgcccgc tttccagtcg ggaaacctg  tcgtgccagc tgcattaatg   780
aatcggccaa cgcgcgggga gaggcggttt gcgtattggg cgctcttccg cttcctcgct   840
cactgactcg ctgcgctcgg                                                860
```

<210> SEQ ID NO 4
<211> LENGTH: 830
<212> TYPE: DNA
<213> ORGANISM: Artificial
<220> FEATURE:
<223> OTHER INFORMATION: commercial vector having insert ARH460-16-2 V
      kappa (M)2-1

<400> SEQUENCE: 4

```
gtaatacgac tcactatagg gcgaattggg ccctctagat gcatgctcga gcggccgcca     60
gtgtgatgga tatctgcaga attcgccctt gacatggagt cagacacact cctgctatgg   120
gtactgctgc tctgggttcc aggttccact ggtgacattg tgctgacaca gtctcctgct   180
tccttagctg tatctctggg gcagagggcc accatctcat acaggccag  caaaagtgtc   240
agtacatctg ctatagtta  tatgcactgg aaccaacaga aaccaggaca gccacccaga   300
ctcctcatct atcttgtatc caacctagaa tctggggtcc ctgccaggtt cagtggcagt   360
gggtctggga cagacttcac cctcaacatc catcctgtgg aggaggagga tgctgcaacc   420
tattactgtc agcacattag ggagcttaca cgttcggagg ggggaccaag ctggaaataa   480
aacgggctga tgctgcacca actgtatcca tcttcccacc atccagtaag cttgggaagg   540
gcgaattcca gcacactggc ggccgttact agtggatccg agctcggtac caagcttggc   600
gtaatcatgg tcatagctgt ttcctgtgtg aaattgttat ccgctcacaa ttccacacaa   660
catacgagcc ggaagcataa agtgtaaagc ctggggtgcc taatgagtga gctaactcac   720
attaattgcg ttgcgctcac tgcccgcttt ccagtcggga aacctgtcgt gccagctgca   780
```
ttaatgaatc ggccaacgcg cggggggagag gcggtttgcg tattgggcgc 830

<210> SEQ ID NO 5
<211> LENGTH: 850
<212> TYPE: DNA
<213> ORGANISM: Artificial
<220> FEATURE:
<223> OTHER INFORMATION: commercial vector having insert ARH460-16-2 V kappa (M)2-2

<400> SEQUENCE: 5

```
gtaatacgac tcactatagg gcgaattggg ccctctagat gcatgctcga gcggccgcca   60
gtgtgatgga tatctgcaga attcgcccett gtcgacatgg agacagacac actgctgtta  120
tgggtactgc tgctctgggt tccaggttcc actggtgaca ttgtgctgac acagtctcct  180
gcttccttag ctgtatctct ggggcagagg gccaccatct catacagggc cagcaaaagt  240
gtcagtacat ctggctatag ttatatgcac tggaaccaac agaaaccagg acagccaccc  300
agactcctca tctatcttgt atccaaccta gaatctgggg tccctgccag gttcagtggc  360
agtgggtctg gacagactt caccctcaac atccatcctg tggaggagga ggatgctgca  420
acctattact gtcagcacat tagggagctt acacgttcgg aggggggacc aagctggaaa  480
taaaacgggc tgatgctgca ccaactgtat ccatcttccc accatccagt aagcttggga  540
agggcgaatt ccagcacact ggcggccgtt actagtggat ccgagctcgg taccaagctt  600
ggcgtaatca tggtcatagc tgtttcctgt gtgaaattgt tatccgctca caattccaca  660
caacatacga gccggaagca taaagtgtaa agcctgggt gcctaatgag tgagctaact  720
cacattaatt gcgttgcgct cactgcccgc tttccagtcg ggaaacctgt cgtgccaact  780
gcattaatga atcggccaac gcgcggggag aggcggtttg cgtattgggc gcttcttccg  840
cttcctcgct                                                         850
```

<210> SEQ ID NO 6
<211> LENGTH: 487
<212> TYPE: DNA
<213> ORGANISM: Artificial
<220> FEATURE:
<223> OTHER INFORMATION: commercial vector having insert H460-16-2 V heavy #1

<400> SEQUENCE: 6

```
cccaagcttc caggggccag gggatagaca ggtgggggtg tcgttttggc tgaggaattg   60
gtgactgagg ttccttgacc ccagtagtcc atagcatagt agtggtacct actaccgtag  120
taattaggcc ttgtacagta ataaagggct gtgtcttcag agctcacttt gctcatttgc  180
aggtccagcg tattttttggc gttgtctctg gagatgatga attgatcctt tagagatggc  240
gtatagttta tcgaagtgct atctggatta acttctccaa tccattctag ccctttccct  300
ggagcctgcc ggacccaact catccagtat ctactaaaat cgaatcctga ggttgcacag  360
gagagtttca gggatcctcc aggctgcacc aggccacctc cagactcgag aagcttcacc  420
tcacactgga ccccttttaa aagagcaaca ataaaaaaaa tcagcccaaa atccatgtca  480
actagta                                                           487
```

<210> SEQ ID NO 7
<211> LENGTH: 477
<212> TYPE: DNA
<213> ORGANISM: Artificial
<220> FEATURE:
<223> OTHER INFORMATION: commercial vector having insert H460-16-2 V heavy #4

<400> SEQUENCE: 7

```
atggattttg ggctgatttt ttttattgtt gctcttttaa aaggggtcca gtgtgaggtg      60
aagcttctcg agtctggagg tggcctggtg cagcctggag atccctgaa  actctcctgt     120
gcaacctcag gattcgattt tagtagatac tggatgagtt gggtccggca ggctccaggg     180
aaagagctag aatggattgg agaagttaat ccagatagca cttcgataaa ctatacgcca     240
tctctaaagg atcaattcat catctccaga gacaacgcca aaaatacgct ggacctgcaa     300
atgagcaaag tgagctctga agacacagcc ctttattact gtacaaggcc taattactac     360
ggtagtaggt accactacta tgctatggac tactggggtc aaggaacctc agtcaccgtt     420
tcctcagcca aaacgacacc cccatccgtt tatccattgg cccctggaag cttggga       477
```

<210> SEQ ID NO 8
<211> LENGTH: 487
<212> TYPE: DNA
<213> ORGANISM: Artificial
<220> FEATURE:
<223> OTHER INFORMATION: commercial vector having insert H460-16-2 V heavy #5

<400> SEQUENCE: 8

```
cccaagcttc caggggccaa gggataaacg ggtgggggtg tcgttttggc tgaggaaacg      60
gtgactgagg ttccttgacc ccagtagtcc atagcatagt agtggtacct actaccgtag     120
taattaggcc ttgtacagta ataaagggct gtgtcttcag agctcacttt gctcatttgc     180
aggtccagcg tattttttggc gttgtctctg agatgatga  attgatcctt tagagatggc    240
gtatagttta tcgaagtgct atctggatta acttctccaa tccattctag ccctttccct     300
ggagcctgcc ggacccaact catccagtat ctactaaaat cgaatcctga ggttgcacag     360
gagagtttca gggatcctcc aggctgcacc aggccacctc cagactcgag aagcttcact     420
tcacactgga ccccttttaa aagagcaaca ataaaaaaaa tcagcccaaa atccatgtcg     480
actagta                                                               487
```

<210> SEQ ID NO 9
<211> LENGTH: 634
<212> TYPE: DNA
<213> ORGANISM: Artificial
<220> FEATURE:
<223> OTHER INFORMATION: commercial vector having insert ARH460-16-2 V heavy #1

<400> SEQUENCE: 9

```
atcgtaatac gactcactat agggcgaatt gggcccctcta gatgcatgct cgagcggccg      60
ccagtgtgat ggatatctgc agaattcgcc cttgggaatt catgaagttg gggctcagct     120
gggtttcatg tcgactagtc acaaaagaat cagcactctc atgtcgaagg gcgaattcca     180
gcacactggc ggccgttact agtggatccg agctcggtac caagcttggc gtaatcatgg     240
tcatagctgt ttcctgtgtg aaattgttat ccgctcacaa ttccacacaa catacgagcc     300
ggaagcataa agtgtaaagc ctggggtgcc taatgagtga gctaactcac attaattgcg     360
ttgcgctcac tgcccgcttt ccagtcggga aacctgtcgt gccagctgca ttaatgaatc     420
ggccaacgcg cggggagagg cggtttgcgt attgggcgct cttccgcttc ctcgctcact     480
gactcgctgc gctcggtcgt tcggctgcgg cgagcggtat cagctcactc aaaggcggta     540
atacggttat ccacagaatc aggggataac gcaggaaaga acatgtgagc aaaaggccag     600
caaaaggcca ggaaccgtaa aaaggccgcg tttt                                  634
```

<210> SEQ ID NO 10
<211> LENGTH: 757
<212> TYPE: DNA
<213> ORGANISM: Artificial
<220> FEATURE:
<223> OTHER INFORMATION: commercial vector having insert ARH460-16-2 V
heavy #3

<400> SEQUENCE: 10

```
gaattgtaat acgactcact agggcgaa ttgggccctc tagatgcatg ctcgagcggc      60
cgccagtgtg gatggatatc tgcagaattc gcccttccca agcttccagg ggccaaggga     120
tagacgggtg ggggtgtcgt tttggctgag gaaacggtga ctgaggttcc ttgaccccag    180
tagtccatag catagtagtg gtacctacta ccgtagtaat taggccttgt acagtaataa    240
agggctgtgt cttcagagct cactttgctc atttgcaggt ccagcgtatt tttggcgttg    300
tctctggaga tgatgaattg atcctttaga gatggcgtat agtttatcga agtgctatct    360
ggattaactt ctccaatcca ttctagccct ttccctggag cctgccggac ccaactcatc    420
cagtatctac taaaatcgaa tcctgaggtt gcacagggag agtttcaggg atcctccagg    480
ctgcaccagg ccacctccag actcgagaag cttcacctca cactggaccc cttttaaaag    540
agcaacaata aaaaaaatca gcccaaaatc catgtcgact agtaagggcg aattccagca    600
cactggcggc cgttactagt ggatccgagc tcggtaccaa gcttggcgta atcatggtca    660
tagctgtttc ctgtgtgaaa ttgttatccg ctcacaattc cacacaacat acgagccgga    720
agcataaagt gtaaagcctg gggtgcctaa tgagtga                              757
```

<210> SEQ ID NO 11
<211> LENGTH: 718
<212> TYPE: DNA
<213> ORGANISM: Artificial
<220> FEATURE:
<223> OTHER INFORMATION: commercial vector having insert ARH460-16-2 V
heavy #17

<400> SEQUENCE: 11

```
gattgaatac gactcactat agggcgaatt gggccctcta gatgcatgct cgagcggccg     60
ccagtgtgat ggatatctgc agaattcgcc cttcccaagc ttccagggac caggggataa    120
acggatgggg gtgtcgtttt ggctgaggaa acggtgactg aggttccttg accccagtag    180
tccatagcat agtagtggta cctactaccg tagtaattag ccttgtaca gtaataaagg     240
gctgtgtctt cagagctcac tttgctcatt tgcaggtcca gcgtattttt ggcgttgtct    300
ctggagatga tgaattgatc ctttagagat ggcgtatagt ttatcgaagt gctatctgga    360
ttaacttctc caatccattc tagccctttc cctggagcct gccgaccca actcatccag     420
tatctactaa aatcgaatcc tgaggttgca caggagagtt tcaggatcc tccaggctgc    480
accaggccac ctccagactc gagaagcttc acctcacact ggacccctt taaaagagca    540
acaataaaaa aaatcagccc aaaatccatg taagggcgaa ttccagcaca ctggcggccg    600
ttactagtgg atccgagctc ggtaccaagc ttggcgtaat catggtcata gctgtttcct    660
gtgtgaaatt gttatccgct cacaattcca cacaatac gagccggaag cataaagt       718
```

<210> SEQ ID NO 12
<211> LENGTH: 40
<212> TYPE: DNA
<213> ORGANISM: Artificial
<220> FEATURE:
<223> OTHER INFORMATION: primer sequence for PCR

```
<400> SEQUENCE: 12
cgtggaagct tcgtacggcc catcggtctt cccctggca                              40

<210> SEQ ID NO 13
<211> LENGTH: 18
<212> TYPE: DNA
<213> ORGANISM: Artificial
<220> FEATURE:
<223> OTHER INFORMATION: primer sequence for PCR

<400> SEQUENCE: 13
tagaaggcac agtcgagg                                                      18

<210> SEQ ID NO 14
<211> LENGTH: 27
<212> TYPE: DNA
<213> ORGANISM: Artificial
<220> FEATURE:
<223> OTHER INFORMATION: primer sequence for PCR

<400> SEQUENCE: 14
gcgccaagat ctgatatcca gatgaca                                            27

<210> SEQ ID NO 15
<211> LENGTH: 30
<212> TYPE: DNA
<213> ORGANISM: Artificial
<220> FEATURE:
<223> OTHER INFORMATION: primer sequence for PCR

<400> SEQUENCE: 15
ggaggttgcg gccgcagtcc gttatatttc                                         30

<210> SEQ ID NO 16
<211> LENGTH: 40
<212> TYPE: DNA
<213> ORGANISM: Artificial
<220> FEATURE:
<223> OTHER INFORMATION: primer sequence for PCR

<400> SEQUENCE: 16
gcggaggcta gcggggatat ccaccatgga ttttgggctg                              40

<210> SEQ ID NO 17
<211> LENGTH: 34
<212> TYPE: DNA
<213> ORGANISM: Artificial
<220> FEATURE:
<223> OTHER INFORMATION: primer sequence for PCR

<400> SEQUENCE: 17
gagtgccgta cgtggaggct gaggaaacgg tgac                                    34

<210> SEQ ID NO 18
<211> LENGTH: 36
<212> TYPE: DNA
<213> ORGANISM: Artificial
<220> FEATURE:
<223> OTHER INFORMATION: primer sequence for PCR

<400> SEQUENCE: 18
gctggctagc acgcgttaaa catgaagttt ccttct                                  36

<210> SEQ ID NO 19
<211> LENGTH: 28
```

```
<212> TYPE: DNA
<213> ORGANISM: Artificial
<220> FEATURE:
<223> OTHER INFORMATION: primer sequence for PCR

<400> SEQUENCE: 19
cgcgaggcta gcacgcgtat ccaccatg                                              28

<210> SEQ ID NO 20
<211> LENGTH: 704
<212> TYPE: DNA
<213> ORGANISM: Artificial
<220> FEATURE:
<223> OTHER INFORMATION: commercial vector having insert ARH460-16-2 V
      kappa #1

<400> SEQUENCE: 20
atgaagtttc cttctcaact tctgctctta ctgctgtttg gaatcccagg catgagatct      60
gatatccaga tgacacagac tacatcctcc ctgtctgtct ctctgggaga cagagtcacc     120
atcaattgca gggcaagtca ggacattaac aattatttaa actggtatca gcagaaacca     180
gatggaactg ttaaactcct gatctactac acatcaagat tacactcagg agtcccatca     240
aggttcagtg gcagtgggtc tggaacagat ttttctctca ccattagcaa cctggagaaa     300
gaagatgttg ccacttactt tgccaacag gtagtacgc ttccattcac gttcggctcg      360
gggacaaagt tggaaataaa acggactgcg gccgcaccat ctgtcttcat cttcccgcca     420
tctgatgagc agttgaatct ggaactgcct ctgttgtgtg cctgctgaat aacttctatc     480
ccagagaggc caaagtacag tggaaggtgg ataacgccct ccaatcgggt aactcccagg     540
agagtgtcac agagcaggac agcaaggaca gcacctacag cctcagcagc accctgacgc     600
tgagcaaagc agactacgag aaacacaaag tctacgcctg cgaagtcacc catcagggcc     660
tgagctcgcc cgtcacaaag agcttcaaca ggggagagtg ttga                     704

<210> SEQ ID NO 21
<211> LENGTH: 704
<212> TYPE: DNA
<213> ORGANISM: Artificial
<220> FEATURE:
<223> OTHER INFORMATION: commercial vector having insert ARH460-16-2 V
      kappa #2

<400> SEQUENCE: 21
atgaagtttc cttctcaact tctgctctta ctgctgtttg gaatcccagg catgagatct      60
gatatccaga tgacacagac tacatcctcc ctgtctgtct ctctgggaga cagagtcacc     120
atcaattgca gggcaagtca ggacattaac aattatttaa actggtatca gcagaaacca     180
gatggaactg ttaaactcct gatctactac acatcaagat tacactcagg agtcccatca     240
aggttcagtg gcagtgggtc tggaacagat ttttctctca ccattagcaa cctggagaaa     300
gaagatgttg ccacttactt tgccaacag gtagtacgc ttccattcac gttcggctcg      360
gggacaaagt tggaaataaa acggactgcg gccgcaccat ctgtcttcat cttcccgcca     420
tctgatgagc agttgaatct ggaactgcct ctgttgtgtg cctgctgaat aacttctatc     480
ccagagaggc caaagtacag tggaaggtgg ataacgccct ccaatcgggt aactcccagg     540
agagtgtcac agagcaggac agcaaggaca gcacctacag cctcagcagc accctgacgc     600
tgagcaaagc agactacgag aaacacaaag tctacgcctg cgaagtcacc catcagggcc     660
tgagctcgcc cgtcacaaag agcttcaaca ggggagagtg ttga                     704
```

<210> SEQ ID NO 22
<211> LENGTH: 704
<212> TYPE: DNA
<213> ORGANISM: Artificial
<220> FEATURE:
<223> OTHER INFORMATION: commercial vector having insert ARH460-16-2 V
      kappa #4

<400> SEQUENCE: 22

| | | | | | |
|---|---|---|---|---|---|
| atgaagtttc | cttctcaact | tctgctctta | ctgctgtttg | gaatcccagg | catgagatct | 60 |
| gatatccaga | tgacacagac | tacatcctcc | ctgtctgtct | ctctgggaga | cagagtcacc | 120 |
| atcaattgca | gggcaagtca | ggacattaac | aattatttaa | actggtatca | gcagaaacca | 180 |
| gatggaactg | ttaaactcct | gatctactac | acatcaagat | tacactcagg | agtcccatca | 240 |
| aggttcagtg | gcagtgggtc | tggaacagat | tttctctcac | cattagcaac | ctggagaaag | 300 |
| aagatgttgc | cacttacttt | tgccaacagg | gtagtacgct | tccattcacg | ttcggctcgg | 360 |
| ggacaaagtt | ggaaataaaa | cggactgcgg | ccgcaccatc | tgtcttcatc | ttcccgccat | 420 |
| ctgatgagca | gttgaaatct | ggaactgcct | ctgttgtgtg | cctgctgaat | aacttctatc | 480 |
| ccagagaggc | caaagtacag | tggaaggtgg | ataacgccct | ccaatcgggt | aactcccagg | 540 |
| agagtgtcac | agagcaggac | agcaaggaca | gcacctacag | cctcagcagc | accctgacgc | 600 |
| tgagcaaagc | agactacgag | aaacacaaag | tctacgcctg | cgaagtcacc | catcagggcc | 660 |
| tgagctcgcc | cgtcacaaag | agcttcaaca | ggggagagtg | ttga | | 704 |

<210> SEQ ID NO 23
<211> LENGTH: 1055
<212> TYPE: DNA
<213> ORGANISM: Artificial
<220> FEATURE:
<223> OTHER INFORMATION: commercial vector having insert ARH460-16-2 V
      heavy #1

<400> SEQUENCE: 23

| | | | | | |
|---|---|---|---|---|---|
| ccatttggtg | tccggcgacg | gtagccaggc | cagcctggcc | atggaagtaa | ttcttggaat | 60 |
| ttgcccattt | tgagtttgga | gcgaagctga | ttgacaaagc | tgcttagccg | ttcaaaggta | 120 |
| ttcttcgaac | ttttttttta | aggtgttgtg | aaaaccaagc | ttctcgagcg | tacgtattaa | 180 |
| ttaactcacg | cgtatccacc | atggattttg | ggctgatttt | ttttattgtt | gctcttttaa | 240 |
| aagggggtcca | gtgtgaggtg | aagcttctcg | agtctggagg | tggcctggtg | cagcctggag | 300 |
| gatccctgaa | actctcctgt | gcaacctcag | gattcgattt | tagtagatac | tggatgagtt | 360 |
| gggtccggca | ggctccaggg | aaagggctag | aatggattgg | agaagttaat | ccagatagca | 420 |
| cttcgataaa | ctatacgcca | tctctaaagg | atcaattcat | catctccaga | gacaacgcca | 480 |
| aaaatacgct | ggacctgcaa | atgagcaaag | tgagctctga | agacacagcc | ctttattact | 540 |
| gtacaaggcc | taattactac | ggtagtaggt | accactacta | tgctatggac | tactgggtc | 600 |
| aaggaacctc | agtcaccgtt | tcctcagcct | ccacgtacgg | cccatcggtc | ttccccctgg | 660 |
| caccctcctc | caagagcacc | tctggggca | cagcggccct | gggctgcctg | gtcaaggact | 720 |
| acttccccga | accggtgacg | gtgtcgtgga | actcaggcgc | cctgaccagc | ggcgtgcaca | 780 |
| ccttcccggc | tgtcctacag | tcctcaggac | tctactccct | cagcagcgtg | gtgaccgtgc | 840 |
| cctccagcag | cttgggcacc | cagacctaca | tctgcaacgt | gaatcacaag | cccagcaaca | 900 |
| ccaaggtgga | caagaaagtt | gagcccaaat | cttgtgacaa | aactcacaca | tgcccaccgt | 960 |
| gcccagcacc | tgaactcctg | ggggaccgt | cagtcttcct | cttccccca | aaacccagga | 1020 |
| caccctcatg | atctcccgga | cccctgaggg | cacat | | | 1055 |

<210> SEQ ID NO 24
<211> LENGTH: 1670
<212> TYPE: DNA
<213> ORGANISM: Artificial
<220> FEATURE:
<223> OTHER INFORMATION: commercial vector having insert ARH460-16-2 V heavy #2

<400> SEQUENCE: 24

```
atggattttg ggctgatttt ttttattgtt gctcttttaa aaggggtcca gtgtgaggtg      60
aagcttctcg agtctggagg tggcctggtg cagcctggag atccctgaa actctcctgt     120
gcaacctcag gattcgattt tagtagatac tggatgagtt gggtccggca ggctccaggg     180
aaagggctag aatggattgg agaagttaat ccagatagca cttcgataaa ctatacgcca     240
tctctaaagg atcaattcat catctccaga dacaacgcca aaaatacgct ggacctgcaa     300
atgagcaaag tgagctctga agacacagcc ctttattact gtacaaggcc taattactac     360
ggtagtaggt accactacta tgctatggac tactggggtc aaggaacctc agtcaccgtt     420
tcctcagcct ccacgtacgg cccatcggtc ttccccctgg cacccctcctc caagagcacc     480
tctgggggca gcgggccct gggctgcctg gtcaaggact acttccccga accggtgacg     540
gtgtcgtgga actcaggcgc cctgaccagc ggcgtgcaca ccttcccggc tgtcctacag     600
tcctcaggac tctactccct cagcagcgtg gtgaccgtgc cctccagcag cttgggcacc     660
cagacctaca tctgcaacgt gaatcacaag cccagcaaca ccaaggtgga caagaaagtt     720
gagcccaaat cttgtgacaa aactcacaca tgcccaccgt gcccagcacc tgaactcctg     780
gggggaccgt cagtcttcct cttccccca aaaactcaca catgcccacc gtgcccagca     840
cctgaactcc tggggggacc gtcagtcttc ctcttccccc caaaacccaa ggacaccctc     900
atgatctccc ggacccctga ggtcacatgc gtggtggtgg acgtgagcca cgaagaccct     960
gaggtcaagt tcaactggta cgtggacggc gtggaggtgc ataatgccaa gacaaagccg    1020
cgggaggagc agtacaacag cacgtaccgt gtggtcagcg tcctcaccgt cctgcaccag    1080
gactggctga atggcaagga gtacaagtgc aaggtctcca acaaagccct cccagccccc    1140
atcgagaaaa ccatctccaa agccaaaggg cagccccgag aaccacaggt gtacaccctg    1200
cccccatccc gggatgagct gaccaagaac caggtcagcc tgacctgcct ggtcaaaggc    1260
ttctatccca gcgacatcgc cgtggagtgg gagagcaatg ggcagccgga gaacaactac    1320
aagaccacgc ctcccgtgct ggactccgac ggctccttct tcctctacag caagctcacc    1380
gtggacaaga gcaggtggca gcaggggaac gtcttctcat gctccgtgat gcatgaggct    1440
ctgcacaacc actacacgca gaagagcctc tccctgtctc cgggtaaatg actcgagcat    1500
gcatctagaa tattacccct aacacctgcc acccagtctt aatcagtggt ggaagaacgg    1560
tctcagaact gtttgtctca attggccatt taagtttata gtgaagactg gttaatgata    1620
acaatgcatc ggaaaccttc aggaggaaag gagaatgttt gtggaacaat                1670
```

<210> SEQ ID NO 25
<211> LENGTH: 988
<212> TYPE: DNA
<213> ORGANISM: Artificial
<220> FEATURE:
<223> OTHER INFORMATION: commercial vector having insert ARH460-16-2 V heavy #6

<400> SEQUENCE: 25

```
cacatttggt gggctggaga ctgtagccag gccagcctgg ccatggaagt aattcttgga      60
```

-continued

| | |
|---|---|
| atttgcccat tttgagtttg gagcgaagct gattgacaaa gctgcttagc cgttcaaagg | 120 |
| tattcttcga acttttttt taaggtgttg tgaaaaccaa gcttctcgag cgtacgtatt | 180 |
| aattaactca cgcgtatcca ccatggattt tgggctgatt ttttttattg ttgctctttt | 240 |
| aaaaggggtc cagtgtgagg tgaagcttct cgagtctgga ggtggcctgg tgcagcctgg | 300 |
| aggatccctg aaactctcct gtgcaacctc aggattcgat tttagtagat actggatgag | 360 |
| ttgggtccgg caggctccag ggaaagggct agaatggatt ggagaagtta atccagatag | 420 |
| cacttcgata aactatacgc catctctaaa ggatcaattc atcatctcca gagacaacgc | 480 |
| caaaaatacg ctggacctgc aaatgagcaa agtgagctct gaagacacag ccctttatta | 540 |
| ctgtacaagg cctaattact acggtagtag gtaccactac tatgctatgg actactgggg | 600 |
| tcaaggaacc tcagtcaccg tttcctcagc ctccacgtac ggcccatcgg tcttccccct | 660 |
| ggcaccctcc tccaagagca cctctggggg cacagcggcc ctgggctgcc tggtcaagga | 720 |
| ctacttcccc gaaccggtga cggtgtcgtg gaactcaggc gccctgacca gcggcgtgca | 780 |
| caccttcccg gctgtcctac agtcctcagg actctactcc ctcagcagcg tggtgaccgt | 840 |
| gccctccagc agcttgggca cccagaccta catctgcaac gtgaatcaca agcccagcaa | 900 |
| caccaaggtg gacaagaagt tgagcccaaa tcttgtgaca aaactcacac atgcccaccg | 960 |
| tgccagcacc tgaactcctg ggggggac | 988 |

<210> SEQ ID NO 26
<211> LENGTH: 37
<212> TYPE: DNA
<213> ORGANISM: Artificial
<220> FEATURE:
<223> OTHER INFORMATION: primer sequence for PCR

<400> SEQUENCE: 26
cgggggatcc gccgccacca tggtatcctc acctcag         37

<210> SEQ ID NO 27
<211> LENGTH: 41
<212> TYPE: DNA
<213> ORGANISM: Artificial
<220> FEATURE:
<223> OTHER INFORMATION: primer sequence for PCR

<400> SEQUENCE: 27
gacagatggt gcagccacag tccgttttat ttccaacttt g      41

<210> SEQ ID NO 28
<211> LENGTH: 33
<212> TYPE: DNA
<213> ORGANISM: Artificial
<220> FEATURE:
<223> OTHER INFORMATION: primer sequence for PCR

<400> SEQUENCE: 28
cgggggatcc ctaacactct cccctgttga agc              33

<210> SEQ ID NO 29
<211> LENGTH: 41
<212> TYPE: DNA
<213> ORGANISM: Artificial
<220> FEATURE:
<223> OTHER INFORMATION: primer sequence for PCR

<400> SEQUENCE: 29
caaagttgga aataaaacgg actgtggctg caccatctgt c     41

<210> SEQ ID NO 30
<211> LENGTH: 41
<212> TYPE: DNA
<213> ORGANISM: Artificial
<220> FEATURE:
<223> OTHER INFORMATION: primer sequence for PCR

<400> SEQUENCE: 30
gacagatggt gcagccacag ttgcggccgc agtccgtttt a        41

<210> SEQ ID NO 31
<211> LENGTH: 41
<212> TYPE: DNA
<213> ORGANISM: Artificial
<220> FEATURE:
<223> OTHER INFORMATION: primer sequence for PCR

<400> SEQUENCE: 31
taaaacggac tgcggccgca actgtggctg caccatctgt c        41

<210> SEQ ID NO 32
<211> LENGTH: 37
<212> TYPE: DNA
<213> ORGANISM: Artificial
<220> FEATURE:
<223> OTHER INFORMATION: primer sequence for PCR

<400> SEQUENCE: 32
catgggggcc cttggtggag ccgtacgtgg aggctga        37

<210> SEQ ID NO 33
<211> LENGTH: 47
<212> TYPE: DNA
<213> ORGANISM: Artificial
<220> FEATURE:
<223> OTHER INFORMATION: primer sequence for PCR

<400> SEQUENCE: 33 ctaggggggcc catttaaatc gccgccacca tggattttgg gctgatt        47

<210> SEQ ID NO 34
<211> LENGTH: 37
<212> TYPE: DNA
<213> ORGANISM: Artificial
<220> FEATURE:
<223> OTHER INFORMATION: primer sequence for PCR

<400> SEQUENCE: 34
ggaacaaaag ctgggtaccg ggccccccct cgaggtc        37

<210> SEQ ID NO 35
<211> LENGTH: 37
<212> TYPE: DNA
<213> ORGANISM: Artificial
<220> FEATURE:
<223> OTHER INFORMATION: primer sequence for PCR

<400> SEQUENCE: 35
ccgatgggcc cttggtggaa gctgaggaaa cggtgac        37

<210> SEQ ID NO 36
<211> LENGTH: 438
<212> TYPE: DNA
<213> ORGANISM: Artificial
<220> FEATURE:
<223> OTHER INFORMATION: commercial vector having insert H460-16-2 V -continued

```
heavy correct

<400> SEQUENCE: 36
atggattttg ggctgatttt ttttattgtt gctctttaa aaggggtcca gtgtgaggtg      60
aagcttctcg agtctggagg tggcctggtg cagcctggag gatccctgaa actctcctgt    120
gcaacctcag gattcgattt tagtagatac tggatgagtt gggtccggca ggctccaggg    180
aaagggctag aatggattgg agaagttaat ccagatagca cttcgataaa ctatacgcca    240
tctctaaagg atcaattcat catctccaga gacaacgcca aaaatacgct ggacctgcaa    300
atgagcaaag tgagctctga agacacagcc ctttattact gtacaaggcc taattactac    360
ggtagtaggt accactacta tgctatggac tactggggtc aaggaacctc agtcaccgtt    420
tcctcagcca aaacgaca                                                  438
```